US006475762B1

(12) United States Patent
Stafford et al.

(10) Patent No.: US 6,475,762 B1
(45) Date of Patent: Nov. 5, 2002

(54) PHYTASE ENZYMES NUCLEIC ACIDS ENCODING PHYTASE ENZYMES AND VECTORS AND HOST CELLS INCORPORATING SAME

(75) Inventors: Christian F. Stafford, Didsbury Manchester (GB); Anthony P. J. Trinci, Bramhall Stockport Cheshire (GB); Jayne L. Brookman, Glossop Derbyshire (GB)

(73) Assignee: Genencor International, Inc., Palo Alto, CA (US)

( * ) Notice: Subject to any disclaimer, the term of this patent is extended or adjusted under 35 U.S.C. 154(b) by 28 days.

(21) Appl. No.: 09/636,499

(22) Filed: Aug. 11, 2000

Related U.S. Application Data

(60) Provisional application No. 60/148,960, filed on Aug. 13, 1999.

(51) Int. Cl.$^7$ .......................... C12N 9/16; C12N 15/55; C12N 1/15

(52) U.S. Cl. ..................... 435/196; 536/23.2; 536/23.1; 536/24.32; 435/320.1; 435/252.3; 435/254.3; 435/254.1

(58) Field of Search ............................... 536/23.1, 23.2, 536/24.32; 435/320.1, 195, 252.3, 254.3, 254.1, 196

(56) References Cited

U.S. PATENT DOCUMENTS 5,747,285 A 5/1998 Bovenberg et al. ........ 435/69.1

FOREIGN PATENT DOCUMENTS

| | | | |
|---|---|---|---|
| EP | 0 897 010 A2 | | 2/1999 |
| WO | 94/03612 | * | 2/1994 |
| WO | WO 98/28409 | | 7/1998 |
| WO | WO 98/30681 | | 7/1998 |

OTHER PUBLICATIONS

Copy of International Search Report for PCT/US 00/22001.

Mullaney et al., "Aspergillus niger myo–inistol hexaphosphate phosphohydrolase gene," *Database EMBL;'Online!*, ID:Anphytase, Jun. 4, 1992, (XP–OO2154692).

Pasamontes et al., "Aspergillus Fumigatus Phytase Gene," Database EMBL, *Online*!, ID:AFY58794M May 25, 1997 (Ex–002154691).

* cited by examiner

*Primary Examiner*—Rebecca E. Prouty
(74) *Attorney, Agent, or Firm*—Genencor International, Inc.

(57) ABSTRACT

A novel DNA is provided which encodes an enzyme having phytase activity isolated from Penicillium. Also provided for is a method of isolating DNA encoding an enzyme having phytase activity from organisms which possess such DNA, transformation of the DNA into a suitable host organism, expression of the transformed DNA and the use of the expressed phytase protein in feed as a supplement.

35 Claims, 20 Drawing Sheets

(SEQ ID NO:1)

GCTATGCATCAAGCTTGGTACCGAGCTCGGATCCACTAGTAACGGCCGCCAGTGTGCTGGAATTCGCCCTT
TCTGATATCTCGATATCCTTGCAGGTTCCACGTACTTGTCGTGATACCCTCTACTCATTCACTAGGTGCA
ATGGCAGCGTTCTCCAAAGAAAAGCATGGGGAGGAAGAGGGCCTACTTGGCGAGAGCCAAGATCAAGGCCG
GAAGCAGCAACGCCAGCGATCGGCCCAAAAATGGCGTACAATTACCCTAgtatccctgctgggcgctttcg
ccctgtttgtgtacttcgcgaaggggtcccagtgcaaccgccccccctcgcatgtcacaacccagcccgac
ctacctgtggcttttcccctgaacaagTCGAAGCGATCATCGCATCACGAACATGCCTGCAATACTGTTGA
TGGCGGTTATCAATGCAACTCCTCGCTCTCGCACAAGTGGGGCCAATATTCGCCCTATTTCTCTCTTTCTG
ACGAATCGGCCATCTCAGATGAGGTACCTCACGGTTGTCAGATCACTTTTGCTCAGGTGATCTCCCGTCAT
GGTGCTCGATTCCCGTCGGCGAAAAAGAGCAAGGCATATGCCGCGCTCGTTAAAAGCATCCAAGCGAACGC
GACTTCATACAAGGGCAACACGGAATTCATCCGCTCATACAACTACACCATGGGCGGTGATGATTTGGTAC
CCTTTGGAGTGAACCAGATGGTGAGCTCGGGAACCAAGTTCTACCAGCGCTATGCGGCGTTAGCTAAAAAG
GCCGTGCCTTTCATTCGCATATCTGACTCGGAGCGGGTTGTGGCTTCAGGAGTGAACTTCATCAAGGGCTT
TCAGAAGGAAAAGTTGAATGACAAGCATGCCAATCACCGTCAATCAAGCCCTAAGGTCAATGTCCTCATCT
CGGAAGAGTCTGGCACCAACAACACTCTGAACCACAGTGAGATCTGTGCCAAGTTCGAAGAAAGTGAACTA
GGCGACGAGGTCGAAGAAAAATACATGGCAATCTTTGTGCCGCCCATCCGAGCCCGTCTTGAGGCTAACCT
CCCTGGCATCAAACTTGAAGACATCGATGTGATCAATCTGATGGATATTTGCCCCTTCGAGACAGTGTCCC
TGACTAGCGATGGATCCAAGCTATCTCCATTCTGCAACCTCTTCACCCAGGCCGAATGGGACCAATACGAC
TACCTCCAGTCACTGAGCAAGTACTACGGTTATGGCGCAGGCAACCCGCTCGGCCCAACCCAGGGTGTCGG
TTTCGTGAACGAACTCATTGCCCGTCTCACTCACGCCCCAGTGGTCGACAACACAAGCACAAACCGTACAC
TCGATGCCCCCGGCGCTGCGACATTCCCCCTCAACTACACCATGTACGCAGACTTCACGCACGACAATGGA
ATGATTCCGTTCTTCTTTGCTTTGGGACTGTACAACGGCACTTCTCCACTCTCCCTCACCAAGGCCCAGTC
AACTAACGAAACGGACGGATTTTCAGCCGCCTGGACGGTGCCTTTCGGTGCTCGTGCTTATGTCGAGATGA
TGCAATGTCGCCGCGACCCGGAGCCGCTCGTGCGAGTCCTCGTTAACGACCGTGTTGTTCCGCTGCATGGT
TGCCCCGTCGATAAGCTTGGCCGTTGTCGCCGTCGCGATTTCGTCAAGGGACTCACTTTTGCGCGCTCTGG
CGGTGATTGGCCCCAGTGCTATGAATAGGAGATTTTGAAAATAATTGGTGCAGGGTTGGTCCTCTTCCAAC
GTACTTTTGTCTAGCGATACCCCAAAGATTGCATCCTTACATACATATCCTTCTTTCTTTTGGCCAATATT
AATGCACCGGTGCCGAAGGGCGAATTCTGCAGATATCCATCACACTGGCGGCCGTCGAGCATGCATCTAGA
GGCCCA

*FIG._1A*

(SEQ ID NO:4)

MAAFSKEKHGEEEGLLGESQDQGRKQQRQRSAQKWRTITLSKRSSHHEHACNTVDGGYQCNSSLSHKWGQY
SPYFSLSDESAISDEVPHGCQITFAQVISRHGARFPSAKKSKAYAALVKSIQANATSYKGNTEFIRSYNYT
MGGDDLVPFGVNQMVSSGTKFYQRYAALAKKAVPFIRISDSERVVASGVNFIKGFQKEKLNDKHANHRQSS
PKVNVLISEESGTNNTLNHSEICAKFEESELGDEVEEKYMAIFVPPIRARLEANLPGIKLEDIDVINLMDI
CPFETVSLTSDGSKLSPFCNLFTQAEWDQYDYLQSLSKYYGYGAGNPLGPTQGVGFVNELIARLTHAPVVD
NTSTNRTLDAPGAATFPLNYTMYADFTHDNGMIPFFFALGLYNGTSPLSLTKAQSTNETDGFSAAWTVPFG
ARAYVEMMQCRRDPEPLVRVLVNDRVVPLHGCPVDKLGRCRRRDFVKGLTFARSGGDWPQCYE

*FIG._2*

(SEQ ID NO:2)

GCAGCGTTCTCCAAAGAAAAGCATGGGGAGGAAGAGGGCCTACTTGGCGAGAGCCAAGATCAAGGCCGGAAG
CAGCAACGCCAGCGATCGGCCCAAAAATGGCGTACAATTACCCTAgtatccctgctgggcgctttcgccctg
tttgtgtacttcgcgaaggggtcccagtgcaaccgccccccctcgcatgtcacaacccagcccgacctacct
gtggcttttcccctgaacaagTCGAAGCGATCATCGCATCACGAACATGCCTGCAATACTGTTGATGGCGGT
TATCAATGCAACTCCTCGCTCTCGCACAAGTGGGGCCAATATTCGCCCTATTTCTCTCTTTCTGACGAATCG
GCCATCTCAGATGAGGTACCTCACGGTTGTCAGATCACTTTTGCTCAGGTGATCTCCCGTCATGGTGCTCGA
TTCCCGTCGGCGAAAAAGAGCAAGGCATATGCCGCGCTCGTTAAAAGCATCCAAGCGAACGCGACTTCATAC
AAGGGCAACACGGAATTCATCCGCTCATACAACTACACCATGGGCGGTGATGATTTGGTACCCTTTGGAGTG
AACCAGATGGTGAGCTCGGGAACCAAGTTCTACCAGCGCTATGCGGCGTTAGCTAAAAAGGCCGTGCCTTTC
ATTCGCATATCTGACTCGGAGCGGGTTGTGGCTTCAGGAGTGAACTTCATCAAGGGCTTTCAGAAGGAAAAG
TTGAATGACAAGCATGCCAATCACCGTCAATCAAGCCCTAAGGTCAATGTCCTCATCTCGGAAGAGTCTGGC
ACCAACAACACTCTGAACCACAGTGAGATCTGTGCCAAGTTCGAAGAAAGTGAACTAGGCGACGAGGTCGAA
GAAAAATACATGGCAATCTTTGTGCCGCCCATCCGAGCCCGTCTTGAGGCTAACCTCCCTGGCATCAAACTT
GAAGACATCGATGTGATCAATCTGATGGATATTTGCCCCTTCGAGACAGTGTCCCTGACTAGCGATGGATCC
AAGCTATCTCCATTCTGCAACCTCTTCACCCAGGCCGAATGGGACCAATACGACTACCTCCAGTCACTGAGC
AAGTACTACGGTTATGGCGCAGGCAACCCGCTCGGCCCAACCCAGGGTGTCGGTTTCGTGAACGAACTCATT
GCCCGTCTCACTCACGCCCCAGTGGTCGACAACACAAGCACAAACCGTACACTCGATGCCCCCGGCGCTGCG
ACATTCCCCCTCAACTACACCATGTACGCAGACTTCACGCACGACAATGGAATGATTCCGTTCTTCTTTGCT
TTGGGACTGTACAACGGCACTTCTCCACTCTCCCTCACCAAGGCCCAGTCAACTAACGAAACGGACGGATTT
TCAGCCGCCTGGACGGTGCCTTTCGGTGCTCGTGCTTATGTCGAGATGATGCAATGTCGCCGCGACCCGGAG
CCGCTCGTGCGAGTCCTCGTTAACGACCGTGTTGTTCCGCTGCATGGTTGCCCCGTCGATAAGCTTGGCCGT
TGTCGCCGTCGCGATTTCGTCAAGGGACTCACTTTTGCGCGCTCTGGCGGTGATTGGCCCCAGTGCTATGAA

FIG._1B

(SEQ ID NO:3)

GCAGCGTTCTCCAAAGAAAAGCATGGGGAGGAAGAGGGCCTACTTGGCGAGAGCCAAGATCAAGGCCGGAAG
CAGCAACGCCAGCGATCGGCCCAAAAATGGCGTACAATTACCCTATCGAAGCGATCATCGCATCACGAACAT
GCCTGCAATACTGTTGATGGCGGTTATCAATGCAACTCCTCGCTCTCGCACAAGTGGGGCCAATATTCGCCC
TATTTCTCTCTTTCTGACGAATCGGCCATCTCAGATGAGGTACCTCACGGTTGTCAGATCACTTTTGCTCAG
GTGATCTCCCGTCATGGTGCTCGATTCCCGTCGGCGAAAAAGAGCAAGGCATATGCCGCGCTCGTTAAAAGC
ATCCAAGCGAACGCGACTTCATACAAGGGCAACACGGAATTCATCCGCTCATACAACTACACCATGGGCGGT
GATGATTTGGTACCCTTTGGAGTGAACCAGATGGTGAGCTCGGGAACCAAGTTCTACCAGCGCTATGCGGCG
TTAGCTAAAAAGGCCGTGCCTTTCATTCGCATATCTGACTCGGAGCGGGTTGTGGCTTCAGGAGTGAACTTC
ATCAAGGGCTTTCAGAAGGAAAAGTTGAATGACAAGCATGCCAATCACCGTCAATCAAGCCCTAAGGTCAAT
GTCCTCATCTCGGAAGAGTCTGGCACCAACAACACTCTGAACCACAGTGAGATCTGTGCCAAGTTCGAAGAA
AGTGAACTAGGCGACGAGGTCGAAGAAAAATACATGGCAATCTTTGTGCCGCCCATCCGAGCCCGTCTTGAG
GCTAACCTCCCTGGCATCAAACTTGAAGACATCGATGTGATCAATCTGATGGATATTTGCCCCTTCGAGACA
GTGTCCCTGACTAGCGATGGATCCAAGCTATCTCCATTCTGCAACCTCTTCACCCAGGCCGAATGGGACCAA
TACGACTACCTCCAGTCACTGAGCAAGTACTACGGTTATGGCGCAGGCAACCCGCTCGGCCCAACCCAGGGT
GTCGGTTTCGTGAACGAACTCATTGCCCGTCTCACTCACGCCCCAGTGGTCGACAACACAAGCACAAACCGT
ACACTCGATGCCCCCGGCGCTGCGACATTCCCCCTCAACTACACCATGTACGCAGACTTCACGCACGACAAT
GGAATGATTCCGTTCTTCTTTGCTTTGGGACTGTACAACGGCACTTCTCCACTCTCCCTCACCAAGGCCCAG
TCAACTAACGAAACGGACGGATTTTCAGCCGCCTGGACGGTGCCTTTCGGTGCTCGTGCTTATGTCGAGATG
ATGCAATGTCGCCGCGACCCGGAGCCGCTCGTGCGAGTCCTCGTTAACGACCGTGTTGTTCCGCTGCATGGT
TGCCCCGTCGATAAGCTTGGCCGTTGTCGCCGTCGCGATTTCGTCAAGGGACTCACTTTTGCGCGCTCTGGC
GGTGATTGGCCCCAGTGCTATGAA

FIG._1C

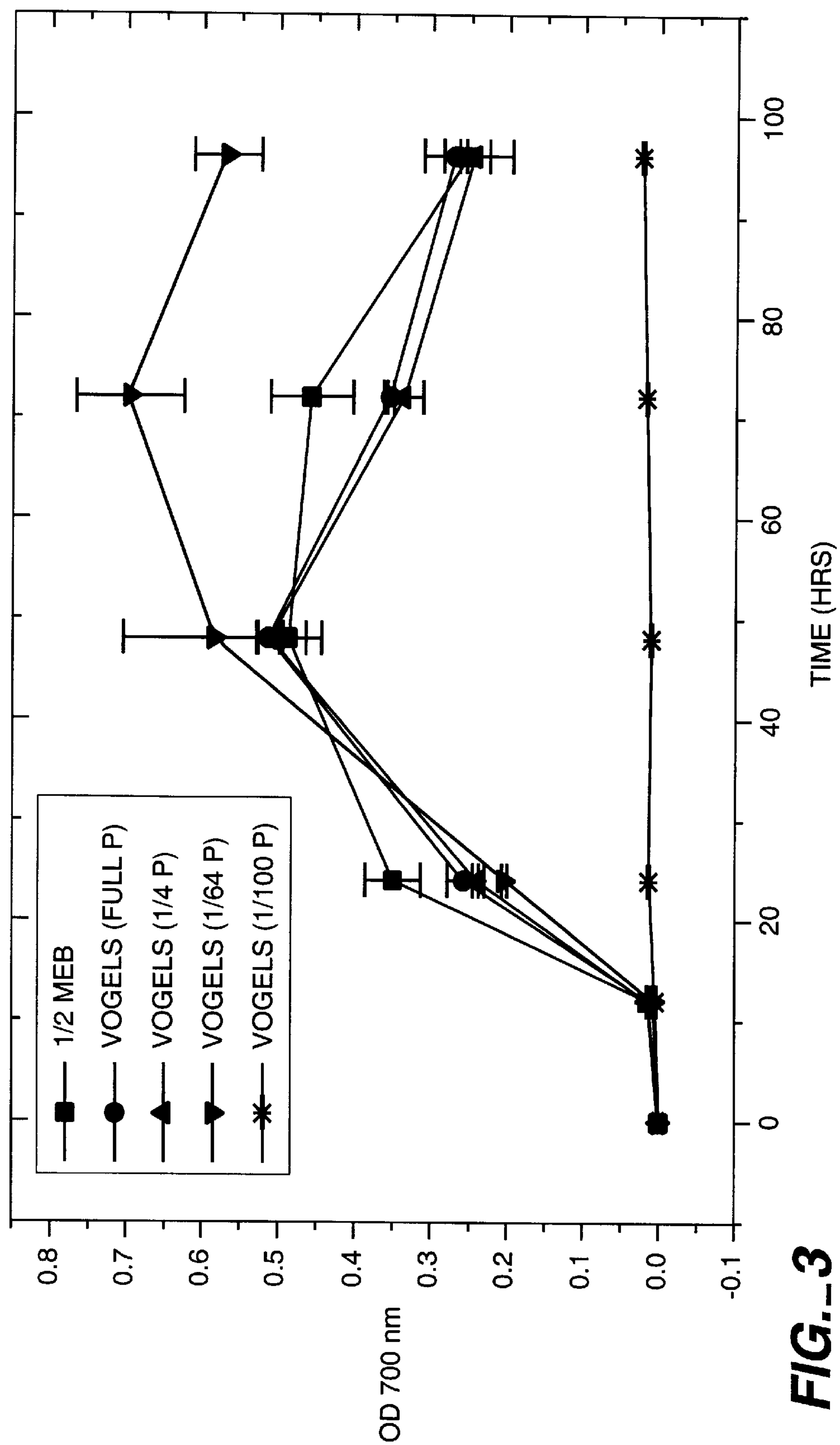
FIG._3

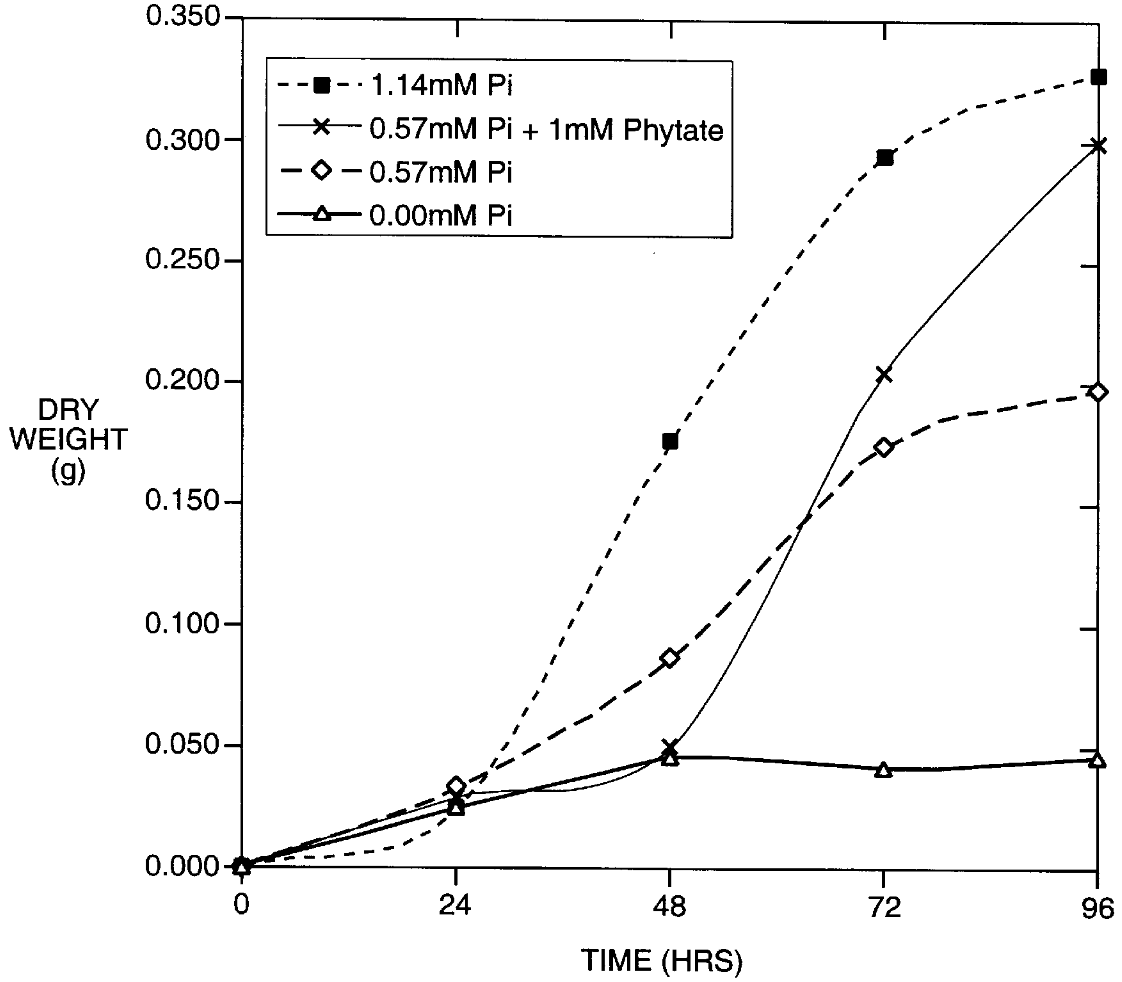
FIG._4

```
                1          11         21         31         41         51         61         71
AnigphyA        MGVSAVLLPL ----YLLSVT SGLAVPAS-R NQSS-CDTVD QGYQCFSETS HLWGQYAPFFS LANE----- ----------
(SEQ ID NO:5)
AfumphyA        MV-TLTFLLS AA--YLLSGR V-SAAPSSAG SKS--CDTVD LGYQCSPATS HLWGQYSPFFS LEDE----- ----------
(SEQ ID NO:6)
A.terreus       MGFLAI-VLS VALLFR-S-T SGT--PLGPR GKHSDCNSVD HGYQCFPELS HKWGLYAPYFS LQDE----- ----------
(SEQ ID NO:7)
M.thermo        MTGLGVMVVM VG--FLAIA- SL--QSES-R P----CDTPD LGFQCGTAIS HFWGQYSPYFS VPSE----- ----------
(SEQ ID NO:8)

                81         91         101        111        121        131        141        151
AnigphyA        ---------- SVIS--PEVP AGCRVTFAQV LSRHGARYPT DSKGKKYSAL IEEIQQNATT FDGKYAFLKT YNYSLGADDL
AfumphyA        --------L- SVSSKLPK-- -DCRITLVQV LSRHGARYPT SSKSKKYKKL VTAIQANATD FKGKFAFLKT YNYTLGADDL
A.terreus       ---------- SPFPLDVP-- EDCHITFVQV LARHGARSPT HSKTKAYAAT IAAIQKSATA FPGKYAFLQS YNYSLDSEEL
M.thermo        --------LD --AS-IP--- DDCEVTFAQV LSRHGARAPT LKRAASYVDL IDRIHHGAIS YGPGYEFLRT YDYTLGADEL

                161        171        181        191        201        211        221        231
AnigphyA        TPFGEQELVN SGIKFYQRYES LTRNIVPFI RSSGSSRVIA SGKKFIEGFQ STKLKDPRAQ PGQSSPKIDV VISEASSSNN
AfumphyA        TPFGEQQLVN SGIKFYQRYKA LARSVVPFI RASGSDRVIA SGEKFIEGFQ QAKLADPGAT NR-AAPAISV IIPESETFNN
A.terreus       TPFGRNQLRD LGAQFYERYNA LTRHINPFV RATDASRVHE SAEKFVEGFQ TARQDDHHAN PHQPSPRVDV AIPEGSAYNN
M.thermo        TRTGQQQMVN SGIKFYRRYRA LARKSIPFV RTAGQDRVVH SAENFTQGFH SALLADRGST VRPTLPYDMV VIPETAGANN

                241        251        261        271        281        291        301        311
AnigphyA        TLDPGT-CTV FED---SELA DTVEANFTAT FVPSIRQRLE NDLSGVTLT- DTE-VTYLMD MCSFDTI--S TSTVD-TK--
AfumphyA        TLDHGV-CTK FEA---SQLG DEVAANFTAL FAPDIRARAE KHLPGVTLT- DED-VVSLMD MCSFDTVART S---DAS-Q-
A.terreus       TLEH-SLCTA FE---SSTVG DDAVANFTAV FAPAIAQRLE ADLPGVQLST DD--VVNLMA MCPFETV--S LT--DDAHT-
M.thermo        TL-HNDLCTA FEEGPYSTIG DDAQDTYLST FAGPITARVN ANLPGANLT- DADTVA-LMD LCPFETVA-S SSS-DPA-TA

                321        331        341        351        361        371        381        391
AnigphyA        ---------L SPFCDLFTHD EWINYDYLQS LKKYYGHGAG NPLGPTQGVG YANELIARLT HSPVHDDTSS NHTLDSSP-A
AfumphyA        ---------L SPFCQLFTHN EWKKYNYLQS LGKYYGYGAG NPLGPAQGIG FTNELIARLT RSPVQDHTST NSTLVSNP-A
A.terreus       ---------L SPFCDLFTAT EWTQYNYLLS LDKYYGYGGG NPLGPVQGVG WANELMARLT RAPVHDHTCV NNTLDASP-A
M.thermo        DAGGGNGRPL SPFCRLFSES EWRAYDYLQS VGKWYGYGPG NPLGPTQGVG FVNELLARLA GVPVRDGTST NRTLDGDP-R

                401        411        421        431        441        451        461        471
AnigphyA        TFPLNSTLYA DFSHDNGIIS ILFALGLYNG TKPLSTTTVE NITQTDGFSS AWTVPFASRL YVEMMQC--- ---------Q
AfumphyA        TFPLNATMYV DFSHDNSMVS IFFALGLYNG TEPLSRTSVE SAKELDGYSA SWVVPFGARA YFETMQC--- ---------K
A.terreus       TFPLNATLYA DFSHDSNLVS IFWALGLYNG TAPLSQTSVE SVSQTDGYAA AWTVPFAARA YVEMMQC--- ---------R
M.thermo        TFPLGRPLYA DFSHDNDMMG VLGALGAYDG VPPLDKTARR DPEELGGYAA SWAVPFAARI YVEKMRCSGG GGGGGGGEGR

                481        491        501        511        521        531
AnigphyA        AEQ-EPLVRV LVNDRVVPLH GCPVD-ALGR CTRDSFVRGL SFARSGGDWA E-CFA
AfumphyA        SEK-EPLVRA LINDRVVPLH GCDVD-KLGR CKLNDFVKGL SWARSGGNWG E-CFS
A.terreus       AEK-EPLVRV LVNDRVMPLH GCPTD-KLGR CKRDAFVAGL SFAQAGGNWA D-CF-
M.thermo        QEKDEEMVRV LVNDRVMTLK GCGADER-GM CTLERFIESM AFARGNGKW- DLCFA
```

FIG._5A

```
              1
P.piceum      ________________________________________________________________
(SEQ. ID NO:9)
P.hordei      MAAFSKEKHGEEEGLLGESQDQGRKQQRQRSAQKWRTITL----------------------------------------
(SEQ. ID NO:10)
AnigphyA      ____________________________________________________MGVSAVLLPL_YL
(SEQ. ID NO:5)
AfumphyA      ____________________________________________________MVTLTFLLSAAYL
(SEQ. ID NO:6)
Aterr9A-1     ____________________________________________________MGFLAIVLSVA_L
(SEQ. ID NO:7)
M.thermo      __________________________________________________________MTGLGV
(SEQ. ID NO:8)
              81
P.piceum      ______________________________________________________RHGARYPTSY
P.hordei      SKRSSHHEHACNTVDGGYQCNSS___________LSHKWGQYSPYFSLSDESAISDEVPHGCQITFAQVISRHGARFPSAK
AnigphyA      LSGVTSGLAVPA__SRNQSSCDTVDQGYQCFSETSHLWGQYAPFFSLANESVISPEVPAGCRVTFAQVLSRHGARYPTDS
AfumphyA      LSGRVS__AAP__SSAGSKSCDTVDLGYQCSPATSHLWGQYSPFFSLEDELSVSSKLPKDCRITLVQVLSRHGARYPTSS
Aterr9A-1     LFRSTSGT__PLGPRGKHSDCNSVDHGYQCFPELSHKWGLYAPYFSLQDESPFPLDVPEDCHITFVQVLARHGARSPTHS
M.thermo      MVVMVGFLAIASLQSE_SRPCDTPDLGFQCGTAISHFWGQYSPYFSVPSELDAS__IPDDCEVTFAQVLSRHGARAPTLK
              161
P.piceum      KDEKYAELVDNIHKTATAYMG__DFSVLKDYKYQLGANNLTELGQQQLIVSGMRFYERYRSLARDNVPFVRSAGSTRVVA
P.hordei      KSKAYAALVKSIQANATSYKGNTEFIRSYNYT__MGGDDLVPFGVNQMVSSGTKFYQRYAALAKKAVPFIRISDSERVVA
AnigphyA      KGKKYSALIEEIQQNATTFDGKYAFLKTYNYS__LGADDLTPFGEQELVNSGIKFYQRYESLTRNIVPFIRSSGSSRVIA
AfumphyA      KSKKYKKLVTAIQANATDFKGKFAFLKTYNYT__LGADDLTPFGEQQLVNSGIKFYQRYKALARSVVPFIRASGSDRVIA
Aterr9A-1     KTKAYAATIAAIQKSATAFPGKYAFLQSYNYS__LDSEELTPFGRNQLRDLGAQFYERYNALTRHINPFVRATDASRVHE
M.thermo      RAASYVDLIDRIHHGAISYGPGYEFLRTYDYT__LGADELTRTGQQQMVNSGIKFYRRYRALARKSIPFVRTAGQDRVVH
              241
P.piceum      SGDFFNQGFQAAKDRDPVSNKTQQPPVINVIIPEGSQWNNTLDVTT_CPSFQNDTSADTAQ__EKFLNVFAPSILQKITA
P.hordei      SGVNFIKGFQKEKLNDKHANHRQSSPKVNVLISEESGTNNTLNHSEICAKF__EE___SELGDEVEEKYMAIFVPP_IRA
AnigphyA      SGKKFIEGFQSTKLKDPRAQPGQSSPKIDVVISEASSSNNTLDPGT_CTVF__ED___SELADTVEANFTATFVPS_IRQ
AfumphyA      SGEKFIEGFQQAKLADPGATNR_AAPAISVIIPESETFNNTLDHGV_CTKF__EA___SQLGDEVAANFTALFAPD_IRA
Aterr9A-1     SAEKFVEGFQTARQDDHHANPHQPSPRVDVAIPEGSAYNNTLEHSL_CTAF__ES___STVGDDAVANFTAVFAPA_IAQ
M.thermo      SAENFTQGFHSALLADRGSTVRPTLPYDMVVIPETAGANNTLHNDL_CTAF__EEGPYSTIGDDAQDTYLSTFAGP_ITA
```

FIG._5B-1

```
          321
P.piceum  GLPGTQL__KV__EDVPLIMDLCPFETVANPNTS___________TQLSPLCDLFTLSEWQSYDYYNTLGKYYGHGQGNP
P.hordei  RLEANLPGIKLEDIDVINLMDICPFETVSLT___________SDGSKLSPFCNLFTQAEWDQYDYLQSLSKYYGYGAGNP
AnigphyA  RLENDLSGVTLTDTEVTYLMDMCSFDTISTS___________TVDTKLSPFCDLFTHDEWINYDYLQSLKKYYGHGAGNP
AfumphyA  RAEKHLPGVTLTDEDVVSLMDMCSFDTVART___________SDASQLSPFCQLFTHNEWKKYNYLQSLGKYYGYGAGNP
Aterr9A-1 RLEADLPGVQLSTDDVVNLMAMCPFETVSLT___________DDAHTLSPFCDLFTATEWTQYNYLLSLDKYYGYGGGNP
M.thermo  RVNANLPGANLTDADTVALMDLCPFETVASSSSDPATADAGGGNGRPLSPFCRLFSESEWRAYDYLQSVGKWYGYGPGNP

          401
P.piceum  LGPTQGVGFVNEVIARMTQSPVKDHTSVNNTLDS__DATTFPLGPALYADFPHDN-------------------------
P.hordei  LGPTQGVGFVNELIARLTHAPVVDNTSTNRTLDA_PGAATFPLNYTMYADFTHDNGMIPFFFALGLYNGTSPLSLTKAQS
AnigphyA  LGPTQGVGYANELIARLTHSPVHDDTSSNHTLDSSP__ATFPLNSTLYADFSHDNGIISILFALGLYNGTKPLSTTTVEN
AfumphyA  LGPAQGIGFTNELIARLTRSPVQDHTSTNSTLVSNP__ATFPLNATMYVDFSHDNSMVSIFFALGLYNGTEPLSRTSVES
Aterr9A-1 LGPVQGVGWANELMARLTRAPVHDHTCVNNTLDASP__ATFPLNATLYADFSHDSNLVSIFWALGLYNGTAPLSQTSVES
M.thermo  LGPTQGVGFVNELLARLAGVPVRDGTSTNRTLDGDP__RTFPLGRPLYADFSHDNDMMGVLGALGAYDGVPPLDKTARRD

          481
P.piceum  --------------------------------------------------------------------------------
P.hordei  TNETDGFSAAWTVPFGARAYVEMMQC_____________RRDPEPLVRVLVNDRVVPLHGCPVDKLGRCRRRDFVKGLTF
AnigphyA  ITQTDGFSSAWTVPFASRLYVEMMQC_____________QAEQEPLVRVLVNDRVVPLHGCPVDALGRCTRDSFVRGLSF
AfumphyA  AKELDGYSASWVVPFGARAYFETMQC_____________KSEKEPLVRALINDRVVPLHGCDVDKLGRCKLNDFVKGLSW
Aterr9A-1 VSQTDGYAAAWTVPFAARAYVEMMQC_____________RAEKEPLVRVLVNDRVMPLHGCPTDKLGRCKRDAFVAGLSF
M.thermo  PEELGGYAASWAVPFAARIYVEKMRCSGGGGGGGGEGRQEKDEEMVRVLVNDRVMTLKGCGADERGMCTLERFIESMAF

          561
P.piceum  ------------
P.hordei  ARSGGDWPQCYE
AnigphyA  ARSGGDWAECFA
AfumphyA  ARSGGNWGECFS
Aterr9A-1 AQAGGNWADCF-
M.thermo  ARGNGKWDLCFA
```

FIG._5B-2

Phy $a^1$ MGVSAVLLPLYLLAGVTSGLAVPASRNQSTCDTVDQGY-QCFSETSHLWGQYA---PFFS
(SEQ ID NO:11)
Phy $a^2$ MGVSAVLLPLYLLSGVTSGLAVPASRNQSSCDTVDQGY-QCFSETSHLWGQYA---PFFS
(SEQ ID NO:12)
Phy $b^1$ M-PRTSLLTL--ACALATGASAFSYGAAIPQSTQEKQFSQEFRDGYSILKHYGGNGPYSE
(SEQ ID NO:13)
Phy $b^3$ M-PRTSLLTL--ACALATGASAFSYGAAIPQSTQEKQFSQEFRDGYSILKHYGGNGPYSE
(SEQ ID NO:14)

Phosphate binding domain PRIMER CS1

Phy a LANESAISPDVPAGCRVTFAQVLSRHGARYPTESKGKKY-SALIEEIQQNVTTFDGKYAF
Phy a LANESVISPEVPAGCRVTFAQVLSRHGARYPTDSKGKKY-SALIEEIQQNATTFDGKYAF
Phy b -RVSYGIARDPPTSCEVDQVIMVKRHGERYPSPSAGKDIEEALAKVYSINTTEYKGDLAF
Phy b -RVSYGIARDPPTGCEVDQVIMVKRHGERYPSPSAGKSIEEALAKVYSINTTEYKGDLAF

Phy a LK---TYNY------------------SLGADDLTPFGEQELVNSGIKFYQRYESLTRNI
Phy a LK---TYNY------------------SLGADDLTPFGEQELVNSGIKFYQRYESLTRNI
Phy b LND-WTY-YVPNE-------CYYNAETTSGP----YAGLLDAYNHGNDYKARYGHLWNGE
Phy b LND-WTY-YVPNE-------CYYNAETTSGP----YAGLLDAYNHGNDYKARYGHLWNGE

Phy a IPF-IRSSGSSRVIASGEKFIEGFQSTKLKDPRAQPGQSSPKIDVVISEASSSNNTLDP-
Phy a VPF-IRSSGSSRVIASGKKFIEGFQSTKLKDPRAQPGQSSPKIDVVISEASSSNNTLDP-
Phy b TVVPFFSSGYGRVIETARKFGEGFFGYNY--------STNAALNIISESEVMGADSLTP-
Phy b TVVPFFSSGYGRVIETARKFGEGFFGYNY--------STNAALNIISESEVMGADSLTP-

Phy a GTCTVFEDSELADTVEAN----FTATFAPSIRQRLEN--DLS-GV-TLTDTEVTYLMDMC
Phy a GTCTVFEDSELADTVEAN----FTATFVPSIRQRLEN--DLS-GV-TLTDTEVTYLMDMC
Phy b -TCDTDNDQ-----TTCDNLT-YQLPQFKVAAARLNS--Q-NPGM-NLTASDVYNLMVMA
Phy b -TCDTDNDQ-----TTCDNLT-YQLPQFKVAAARLNS--Q-NPGM-NLTASDVYNLIVMA

Central phytase-specific domain PRIMER CS2

Phy a SFDTISTSTVDTKLSPFCDLFTHDEWIHYDYLQSLK--------KYYGHGAGNPLGPTQG
Phy a SFDTISTSTVDTKLSPFCDLFTHDEWINYDYLQSLK--------KYYGHGAGNPLGPTQG
Phy b SFELNARPFSN-----WINAFTQDEWVSFGYVEDLN--------YYYCAGPGDKNMAAVG
Phy b SFELNARPFSN-----WINAFTQDEWVSFGYVEDLN--------YYYCAGPGDKNMAAVG

Phy a VGYANELIARLTHSPVHDDTSSNHTLDSNPATFPLNSTLYADFSHDNGIISILFALGLYN
Phy a VGYANELIARLTHSPVHDDTSSNHTLDSSPATFPLNSTLYADFSHDNGIISILFALGLYN
Phy b AVYANASLTLLNQGPKE--AGS----------------LFFNFAHDTNITPILAALGVLI
Phy b AVYANASLTLLNQGPKE--AGP----------------LFFNFAHDTNITPILAALGVLI

Phy a GTKPLSTTTVENIT-QTDGFSSAWTVPFASRLYVEMMQCQA----EQEPLVRVLVNDRVV
Phy a GTKPLSTTTVENIT-QTDGFSSAWTVPFASRLYVEMMQCQA----EQEPLVRVLVNDRVV
Phy b P---NEDLPLDRVAF-GNPYSIGNIVPMGGHLTIERLSCQATALSDEGTYVRLVLNEAVL
Phy b P---NEDLPLDRVAF-GNPYSIGNIVPMGGHLTIERLSCQATALSDKGTYVRLVLNEAVL

Phy a PLHGCPIDAL----GRCTRDSFVRGLSFARSGGD-------------------------W
Phy a PLHGCPVDAL----GRCTRDSFVRGLSFARSGGD-------------------------W
Phy b PFNDCTSGPGYS----CPLANYTSILNKNLP-------DYTTTC-NVSA-SYPQYLSFWW
Phy b PFNDCTSGPGYS----CPLANYTSILNKNLP-------DYTTTC-NVSA-SYPQYLSFWW

*FIG._6*

```
             1          11         21         31         41         51
P hordei     __________ __________ __________ __________ __________ __________
(SEQ ID NO:15)
P.hordei3D   __________ __________ __________ __________ __________ __________
(SEQ ID NO:16)
AnigphyA     MGVSAVLLPL YLLSVTSGLA VPASRNQSSC DT__VDQGYQ CFSETSHLWG QYAPFFSLAN
(SEQ ID NO:5)
AfumphyA     MVTLTFLLSA AYLLSGRVSA APSSAGSKSC DT__VDLGYQ CSPATSHLWG QYSPFFSLED
(SEQ ID NO:6)
Aterr9A-1    MGFLAIVLSV ALLFRSTSGT PLGPRGKHS_ DCNSVDHGYQ CFPELSHKWG LYAPYFSLQD
(SEQ ID NO:7)
M.thermo     MTGLGVMVVM VGFLAIASLQ SESRPCDTP_ _____DLGFQ CGTAISHFWG QYSPYFSVPS
(SEQ ID NO:8)
             61         71         81         91         101        111
P hordei     __________ __________ __________ __________ __________ ______FIRS
P.hordei3D   __________ __________ __RHGARYPS AKKSKAYAAL VKSIQANATS YKGNTEFIRS
AnigphyA     E_SVISPEVP AGCRVTFAQV LSRHGARYPT DSKGKKYSAL IEEIQQNATT FDGKYAFLKT
AfumphyA     ELSVSSKLPK D_CRITLVQV LSRHGARYPT SSKSKKYKKL VTAIQANATD FKGKFAFLKT
Aterr9A-1    ESPFPLDVPE D_CHITFVQV LARHGARSPT HSKTKAYAAT IAAIQKSATA FPGKYAFLQS
M.thermo     ELDASIPDDC E___VTFAQV LSRHGARAPT LKRAASYVDL IDRIHHGAIS YGPGYEFLRT

             121        131        141        151        161        171
P hordei     YNYTMGGDDL VPFGVNQMVS SGTKFYQRYA ALAKKAVPFI RISDSERVVA SGVNFIKGFQ
P.hordei3D   YNYTMGGDDL VPFGVNQMVS SGTKFYQRYA ALAKKAVPFI RISDSERVVA SGVNFIKGFQ
AnigphyA     YNYSLGADDL TPFGEQELVN SGIKFYQRYE SLTRNIVPFI RSSGSSRVIA SGKKFIEGFQ
AfumphyA     YNYTLGADDL TPFGEQQLVN SGIKFYQRYK ALARSVVPFI RASGSDRVIA SGEKFIEGFQ
Aterr9A-1    YNYSLDSEEL TPFGRNQLRD LGAQFYERYN ALTRHINPFV RATDASRVHE SAEKFVEGFQ
M.thermo     YDYTLGADEL TRTGQQQMVN SGIKFYRRYR ALARKSIPFV RTAGQDRVVH SAENFTQGFH

             181        191        201        211        221        231
P hordei     KEKLNDKHAN HRQSSPKVNV LISEESGTNN TLNHSEICAK FEE___SELG DEVEEKYMAI
P.hordei3D   KEKLNDKHAN HRQSSPKVNV LISEESGTNN TLNHSEICAK FEE___SELG DEVEEKYMAI
AnigphyA     STKLKDPRAQ PGQSSPKIDV VISEASSSNN TLDPGT_CTV FED___SELA DTVEANFTAT
AfumphyA     QAKLADPGAT NR_AAPAISV IIPESETFNN TLDHGV_CTK FEA___SQLG DEVAANFTAL
Aterr9A-1    TARQDDHHAN PHQPSPRVDV AIPEGSAYNN TLEHSL_CTA FES___STVG DDAVANFTAV
M.thermo     SALLADRGST VRPTLPYDMV VIPETAGANN TLHNDL_CTA FEEGPYSTIG DDAQDTYLST
```

FIG._7A

```
             241        251        261        271        281        291
P hordei     FVPPIRARLE ANLPGIKLED IDVINLMDIC PFETVSLT__ _________S DGSKLSPFCN
P.hordei3D   FVPPIRARLE ANLPGIKLED IDVINLMDIC PFETVSLT__ _________S DGSKLSPFCN
AnigphyA     FVPSIRQRLE NDLSGVTLTD TEVTYLMDMC SFDTISTS__ _________T VDTKLSPFCD
AfumphyA     FAPDIRARAE KHLPGVTLTD EDVVSLMDMC SFDTVART__ _________S DASQLSPFCQ
Aterr9A-1    FAPAIAQRLE ADLPGVQLST DDVVNLMAMC PFETVSLT__ _________D DAHTLSPFCD
M.thermo     FAGPITARVN ANLPGANLTD ADTVALMDLC PFETVASSSS DPATADAGGG NGRPLSPFCR

             301        311        321        331        341        351
P hordei     LFTQAEWDQY DYLQSLSKYY GYGAGNPLGP TQGVGFVNEL IARLTHAPVV DNTSTNRTLD
P.hordei3D   LFTHDEWV-- ---------- ---------- ---------- ---------- ----------
AnigphyA     LFTHDEWINY DYLQSLKKYY GHGAGNPLGP TQGVGYANEL IARLTHSPVH DDTSSNHTLD
AfumphyA     LFTHNEWKKY NYLQSLGKYY GYGAGNPLGP AQGIGFTNEL IARLTRSPVQ DHTSTNSTLV
Aterr9A-1    LFTATEWTQY NYLLSLDKYY GYGGGNPLGP VQGVGWANEL MARLTRAPVH DHTCVNNTLD
M.thermo     LFSESEWRAY DYLQSVGKWY GYGPGNPLGP TQGVGFVNEL LARLAGVPVR DGTSTNRTLD

             361        371        381        391        401        411
P hordei     A_PGAATFPL NYTMYADFTH DNGMIPFFFA LGLYNGTSPL SLTKAQSTNE TDGFSAAWTV
P.hordei3D   ---------- ---------- ---------- ---------- ---------- ----------
AnigphyA     SSP__ATFPL NSTLYADFSH DNGIISILFA LGLYNGTKPL STTTVENITQ TDGFSSAWTV
AfumphyA     SNP__ATFPL NATMYVDFSH DNSMVSIFFA LGLYNGTEPL SRTSVESAKE LDGYSASWVV
Aterr9A-1    ASP__ATFPL NATLYADFSH DSNLVSIFWA LGLYNGTAPL SQTSVESVSQ TDGYAAAWTV
M.thermo     GDP__RTFPL GRPLYADFSH DNDMMGVLGA LGAYDGVPPL DKTARRDPEE LGGYAASWAV

             421        431        441        451        461        471
P hordei     PFGARAYVEM MQC_______ _______RRDP EPLVRVLVND RVVPLHGCPV DKLGRCRRRD
P.hordei3D   ---------- ---------- ---------- ---------- ---------- ----------
AnigphyA     PFASRLYVEM MQC_______ _______QAEQ EPLVRVLVND RVVPLHGCPV DALGRCTRDS
AfumphyA     PFGARAYFET MQC_______ _______KSEK EPLVRALIND RVVPLHGCDV DKLGRCKLND
Aterr9A-1    PFAARAYVEM MQC_______ _______RAEK EPLVRVLVND RVMPLHGCPT DKLGRCKRDA
M.thermo     PFAARIYVEK MRCSGGGGGG GGGEGRQEKD EEMVRVLVND RVMTLKGCGA DERGMCTLER

             481        491
P hordei     FVKGLTFARS GGDWPQCYE*
P.hordei3D   ---------- ----------
AnigphyA     FVRGLSFARS GGDWAECFA-
AfumphyA     FVKGLSWARS GGNWGECFS-
Aterr9A-1    FVAGLSFAQA GGNWADCF--
M.thermo     FIESMAFARG NGKWDLCFA-
```

FIG._7B

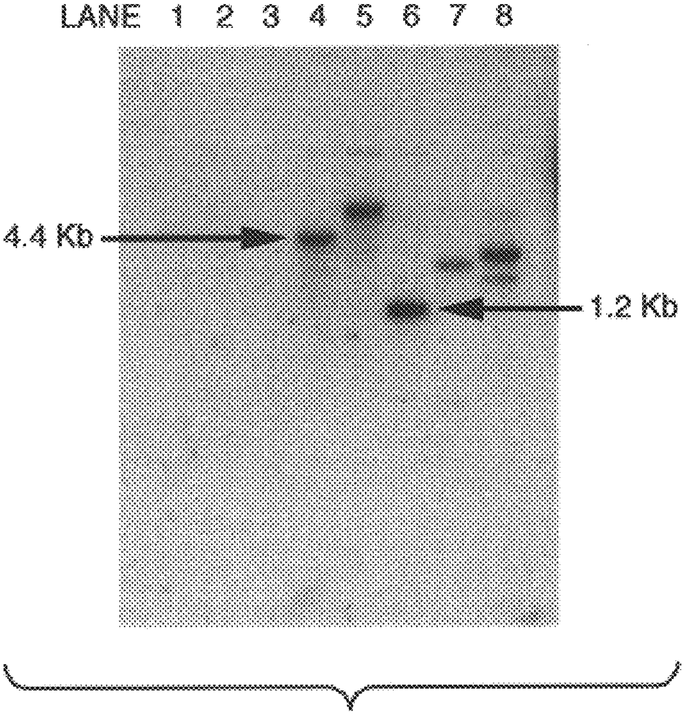
FIG._8
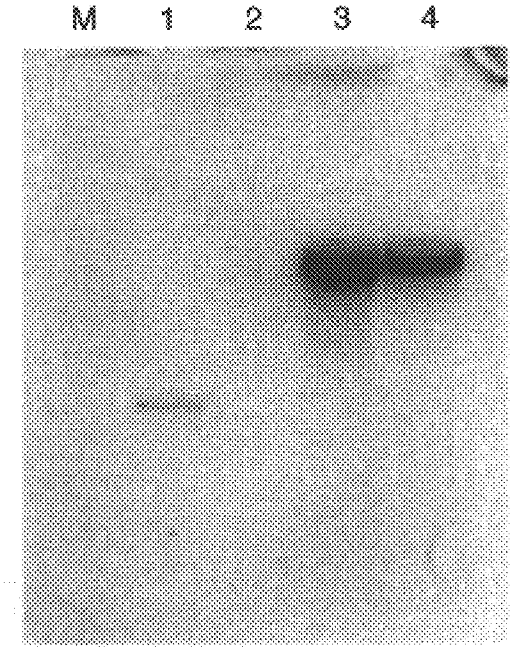
All genomic DNA was digested with *EcoRV* and the Southern was probed with a 650 by phytase probe from *P. hordei*
Marker lane - Amresco E261 Standards
Lane 1 Positive control probe DNA
Lane 2 *Aspergillus nidulans* untransformed
Lane 3 Transformant CS213-2
Lane 4 Transformant CS213-4
FIG._14

(SEQ ID NO: 17)

```
   1  GAATTCATCC GCTCATACAA CTACACCATG GGCGGTGATG ATTTGGTACC
  51  CTTTGGAGTG AACCAGATGG TGAGCTCGGG AACCAAGTTC TACCAGCGCT
 101  ATGCGGCGTT AGCTAAAAAG GCCGTGCCTT TCATTCGCAT ATCTGACTCG
 151  GAGCGGGTTG TGGCTTCAGG AGTGAACTTC ATCAAGGGCT TTCAGAAGGA
 201  AAAGTTGAAT GACAAGCATG CCAATCACCG TCAATCAAGC CCTAAGGTCA
 251  ATGTCCTCAT CTCGGAAGAG TCTGGCACCA ACAACACTCT GAACCACAGT
 301  GAGATCTGTG CCAAGTTCGA AGAAAGTGAA CTAGGCGACG AGGTCGAAGA
 351  AAAATACATG GCAATCTTTG TGCCGCCCAT CCGAGCCCGT CTTGAGGCTA
 401  ACCTCCCTGG CATCAAACTT GAAGACATCG ATGTGATCAA TCTGATGGAT
 451  ATTTGCCCCT TCGAGACAGT GTCCCTGACT AGCGATGGAT CCAAGCTATC
 501  TCCATTCTGC AACCTCTTCA CCCAGGCCGA ATGGGACCAA TACGACTACC
 551  TCCAGTCACT GAGCAAGTAC TACGGTTATG GCGCAGGCAA CCCGCTCGGC
 601  CCAACCCAGG GTGTCGGTTT CGTGAACGAA CTCATTGCCC GTCTCACTCA
 651  CGCCCCAGTG GTCGACAACA CAAGCACAAA CCGTACACTC GATGCCCCCG
 701  GCGCTGCGAC ATTCCCCCTC AACTACACCA TGTACGCAGA CTTCACGCAC
 751  GACAATGGAA TGATTCCGTT CTTCTTTGCT TTGGGACTGT ACAACGGCAC
 801  TTCTCCACTC TCCCTCACCA AGGCCCAGTC AACTAACGAA ACGGACGGAT
 851  TTTCAGCCGC CTGGACGGTG CCTTTCGGTG CTCGTGCTTA TGTCGAGATG
 901  ATGCAATGTC GCCGCGACCC GGAGCCGCTC GTGCGAGTCC TCGTTAACGA
 951  CCGTGTTGTT CCGCTGCATG GTTGCCCCGT CGATAAGCTT GGCCGTTGTC
1001  GCCGTCGCGA TTTCGTCAAG GGACTCACTT TTGCGCGCTC TGGCGGTGAT
1051  TGGCCCCAGT GCTATGAATA GGAGATTTTG AAAATAATTG GTGCAGGGTT
1101  GGTCCTCTTC CAACGTACTT TTGTCTAGCG ATACCCCAAA GATTGCATCC
1151  TTACATACAT ATCCTTCTTT CTTTTGGCCA ATATTAATGC ACTACACGTT
1201  ATTACGAAAT CTGCTTGAAA ACAATATAAT TGCATCCAAA TATATAATCA
1251  AAAGGCTCTA ACACATGCAA GTCATCAAAA AGGTAATCCA AACAGCCCCC
1301  AACTCCAAAC AAAGAAAAGT CCAAATAATA ATCAGCACGT TTTAGGCATC
1351  TCTCTACCTC TCTCACTTTT ACATACTCCA ATGTGGCTGA CCATTCCTTT
1401  TCACTTGATG CGGGGCAGAA ATAACCCACG CCTCCCAAAG AGGCATTTGC
1451  TCATGCAAGA CATGTACACC ATCATCCCCC AAGTCCTCAC TAGACAAAGC
1501  ACGCAGTTTT TCAAGCGAAG TCCGCCTCAA CGGCAATCGC CTTCCCCCTA
1551  ATAAAGCAGG GAGTCCATCA GATGCGAGCG GGGCAGCAGT CGGCGACTGA
1601  ACAGCCGAGG ACGTACCAGT CGCAACAGTA AAAGAAGATG GCACAGGGCC
1651  AGTAGGGTAA TTATCGAACA CCTCAACACC GTTTGAGACA GCAACCGAAT
1701  CAAAGTGTGC AGCGTAACCA ATATCCTTCA GAACCAACCG CTCCAGCTGC
1751  TCCATTTCCT CGCGCAGGAC AACCAACACA TCGCGCCACT GCCCGCCAGG
1801  TCGGAGGTAG ATGCCGAGTA AGCGGAAATC ACGCAATTGA GGACTGTGAC
1851  GACGTGCGAG TGCGATGATC TCGTCTGCGC TCAGACGCCA GCCTTGGATG
1901  CTGAGTTTGC GGAGGGTTTT CCAGCGGATG TGGTGGAAGA GTAGCTCGAG
1951  GTCAAGGTCT AAGGGTGTTT TGCTGAGGAA GCCGATGTGG ATGGCGATGA
2001  GGTTCTTGGC TGCGACGAAG AACCGGTGGA AGACTTCTGA GAGATCGGCC
2051  ATTGTTGCGG TGATGTCGGT TGTTGAGTGG AAGTTTATGT CGAGGCTTGT
2101  GAGGCGTCCG CCCATGGCGG CGAGAGTTGT TGATGGAGCG CGGAGGAGCT
2151  GGAGGGTTGC TTCGGGGCTG ATTTGGGGCC CTGTGAAACG GATGGAGCTG
2201  CATTTTGAGT CGAGGAGGGC GATGCTGAGG CTTGTTACGG CGCGCGAACA
2251  GGCGGTTTCC CAGTCGAAGC GGACGCTTGT TGCGGTCCTG CCGGTTCCTA
2301  GTGAGCGGTC GCGTATAAAG TCGATGAGGT GCTCGTCTGC TTCGTCTTGC
2351  AGTCTTAGGA GTTTTATTTC CTGTAGAGCC GAGAACGATG AGATTGCACG
2401  GCGGAGGCGG GTTTGGTCGT TGTTGGTTTC AGTTAGATTG GTTTGTTCAC
2451  GTAGTCGGCG ACTGTGTAGT TGGGATATTT CGGGATTTTC TGACCCCAAA
2501  GTTCGTAGTG TCCGGGCCCA TCCTGTATTT TGCTATTAGT TTAATTTGCT
2551  CGGTTGTGCA TGAGAGATTG AAGAGCTGGT ACCGCTTCCT TGATAAAAGG
```

*FIG._9A*

```
2601  GTCGCACCAT GTATGTGATG GTTTTCACAT AATAGGCCAA CTGCATGTCT
2651  ACCAGCTCAT CTAATCGCCG GAAGCCATGA TCAGAAAAGC GTAGAGTGAA
2701  TCGACTGAAC TTGTAAGGGG TGCCGATTCG CATGAAGCGC TTGCAGACGA
2751  GCCGAAAGTG ATCAAGATCG GACACTTCAT GTTCGTGGTT GCTAGGCCTG
2801  GAAGTATGTC CATTTCCATT GAATCTGCCA TTTAGGGCTC GAGGTGCGGG
2851  TTCGAGAAGA AATGACAAGA TCTCGCTCAG TAGCTCGTCA GCAAGATCAT
2901  AAATGTGACG TGGCTGGGCC ATGATCGGCG CGCGCAGCCG AAGCATCGGC
2951  TGCTTGTTGA AGTAGCAGCA ACATGGAAAT ATGGAGGAAT TGAGGGAAAA
3001  TCGATGTTCT TAACCTGTCC CCAAGACCGG AGAGACAAAT CACGGAGGGA
3051  ATTGGGGAAA GGGGGAGAGA ATAAGAAATA AAAATAAAAT AAAACAAAAA
3101  AACCATGTCG AATACTCGAC TCGTCGTTCT CCTGCAGACA CTAGTAGGAC
3151  AGTTGACTTG TCTCACYATG CATAACGAGA GCTCTCGCCC TAACGATTGA
3201  TTTCGCGACC GGGGATGATC GTCAAGTGCC TGATTTAGCG CCCTCTGCAC
3251  TGACAAGCCG GGCTCTCTGA CACGATCCGC TTAATTTCAT TGGTGACGCT
3301  GCCACACCAG AATCACATGA TTGATTGACT CTGCGGCCAG CCAGCGCGCG
3351  AACCTGCAGG AAAGGCCATT GAATGAGAGC GAGTAGTGTT GGAGGGGCCA
3401  ATGTCGACCC CGCCGGGAAG TCGTCACATC ATGCAGAGTG ATGGACCATG
3451  CGTGTGGATT ATGTGTCTGC CCAAGAGGTA GGCAACTATT GATTGGGGGT
3501  TAATGGCCGA AACCAAGATG AACTAATGTA TGTACAAGTG TTTGAGAGAT
3551  TATCTACTAG CTGTTGGATC TTCCATATCA TTACGTGCCG TGTGTACCTA
3601  TCAGACCTTC GCGAGAXGGA CTCGGCGCCG TCTGATATCT GTGCTGCTGA
3651  TCTTGGACTC GAAGCCTTCA AGATCAGTGG CCGTGGCTGC TTCTCCAGAT
3701  TGGAGTACAT CCACCTCGAA TACAGCAAGG CCGTTCCATC CCTTCTTCAA
3751  CCGCTCTTCG TTGACGGCCG CCCCTCCGGA GTGTGTCTCC TTTGAAACAA
3801  CAATTGCTCC AAGGTTCTCC TCGGTAATCG TAGGCCCAAA AGGATCGGAG
3851  ATCTCCACAA ATTCAAAAGC CAAGTTGGGT TGGATCCTTA CAAGGACAGT
3901  CTTCCCATTG GGTCCTGGCG CAAAAACACG CTCGATCTGC GGTGATTTCT
3951  TTTCAGGAGA GAAATCCATA ATGGCCGTCA GAAAATCTGC AGTACTCTGC
4001  CAACGTTCCT CCCAACTCTC AAGAAATTCG GCATATTTTT TATTGACCAA
4051  CAGCGCATCC CCGGTCACTC CGATGGTCAG GCGGCCCTCC TGCTCCCGGT
4101  CCAGCGGTTC CAGGACCAAT GCAACTGCCG TGAGCAAGAG CTTGTGACCA
4151  ACATGAAGGT GATCAAATGT GCCACCAACG ACCACGGAAT AGTATGGAGT
4201  GGATGGATGT TGGTCGTCAG GAATTAACAG GCGGTCAGAG ATCTCCCAGT
4251  CAGGCTGGCT GGTAATGGCT TGCATGCTTG CCGCCGTGCC GTCCCGAGTC
4301  TGACTGCTAA CACTGTTGGT GAAGGAATTA GCCAAATTTT GGCCATTTGT
4351  GTTGGACATA TAGAAAACAT GATCCCAACG GCGCCTTGAA TTTGCTAGTG
4401  ATTGGATGTC CAGAATGGGC CCAAAGCGAG GACTATCAGA AGCCTGGATG
4451  GTCGAGGTGC TCTCACTTGC ATTGATAAAT ACCACCCGGG TATCAATGCC
4501  ACCCGGAGAA TCCAATTCAA TGTTCTGTGT TGCACAGACA ACACCAACCA
4551  GGGTGTAGAC GCTGCTCAGA TAATGTTGGA GTTGTGCAAA CACTCTGGCC
4601  CGAGGTTGGC AGGCTGGGGA AAGAAGATCT GGAATGGCCA AAGCAATATC
4651  CAGCATAGCC GTACGGTTGG ATCCAATCAA GGCATTTGAG AGCTTAGTGT
4701  AGACATCCAC CAAGGATGGC TGGAAGGCAT CTTTGACTTG GACAAAAGAA
4751  AAGGCTGGAG GCGGGGGAAG TAGTAGTAAA GCCGTGGGTG AATTGGTATG
4801  ATCGGAAGCC ATGGTGTTAA GAATATATAA CTACAGTAAC AATCACTGGG
4851  GTTCACGGAT ATCAAGCCAA CAAAGAATTC CTGCAGCCCG GGGGATCC.
```

FIG._9B

(SEQ ID NO: 18)

TAGGGCGAGTTGGAGCTCCACCGCGGTGGCGGCCGCTCTAGAACTAGTGG
ATCCCCCGGGCTGCAGGAATTCGATT
CGGCACCGGTGGAAGAGGACCAAC
CCTGCACCAATTATTTTCAAAATCTCCTATTCATAGCACTGGGGCCAATC
ACCGCCAGAGCGCGCAAAAGTGAGTCCCTAGACGAAATCGCGACGGCGAC
AACGGCCAAGCTTATCGACGGGGCAACCATGCAGCGGAACAACACGGTCG
TTAACGAGGACTCGCACGAGCGGCTCCGGGTCGCGGCGACATTGCATCAT
CTTGACATAAGCACGAGCACCGAAAGGCACCGTCCAGGCGGCTGAAAATC
CGTCCGTTTCGTTAGTTGACTGGGCCTTGGTGAGGGAGAGTGGAGAAGTG
CCGTTGTACAGTCCCAAAGCAAAGAAGAACGGAATCATTCCATTGTCGTG
CGTGAAGTCTGCGTACATGGTGTAGTTGAGGGGGAATGTCGCAGCGCCGG
GGGCATCGAGTGTACGGTTTGTGCTTGTGTTGTCGACCACTGGGGCGTGA
GTGAGACGGGCAATGAGTTCGTTCACGAAACCGACACCCTGGGTTGGGCC
GAGCGGGTTGCCTGCGCCATAACCGTAGTACTTGCTCAGTGACTGGAGGT
AGTCGTATTGGTCCCATTCGGCCTGGGTGAAGAGGTTGCAGAATGGAGAT
AGCTTGGATCCATCGCTAGTCAGGGACACTGTCTCGAAGGGGCAAATATC
CATCAGATTGATCACATCGATGTCTTCAAGTTTGATGCCAGGGAGGTTAG
CCTCAAGACGGGACTCGGATGGGCGGCACAAAGATTGCCATGTATTTTTT
CTTCGACCTC

(SEQ ID NO: 19)

GRRKNTWQSLCRPSESRLEANLPGIKLEDIDVINLMDICPFETVSLTSDG
SKLSPFCNLFTQAEWDQYDYLQSLSKYYGYGAGNPLGPTQGVGFVNELIA
RLTHAPVVDNTSTNRTLDAPGAATFPLNYTMYADFTHDNGMIPFFFALGL
YNGTSPLSLTKAQSTNETDGFSAAWTVPFGARAYVKMMQCRRDPEPLVRV
**LVNDRVVPLHGCPVDKLGRCRRRDFV*GLTFARSGGDWPQCYE***EILKII
GAGLVLFHRCRIEFLQPGGSTSSRAAATAVELQLAL

Phytase sequence highlighted in bold, including stop, at the end of the protein.

FIG._10A

(SEQ ID NO: 20)

CCCATCACTSAAGGGAAAAAAAGCTGGGTACCGGGCCCCCCCTCGAGGTC
GACGGTATCGAT
AAGCTTGATTCGGCACCGGTGGAAGAGGACCAACCAGC
GGGATCAAAACACTCACGAGCACAACCTCCGCAAGGGGTTAACCCAAATG
CTTTAGAGCCAGGTCGAAATTTAAAAATGNACTGATTTCCCCCTCTTCGC
ATTCGATATCCTTGCAGGTTCCACGTACTTGTCGTGATACCCTCTACTCA
TTCACTAGGTGCAATGGCAGCGTTCTCCAAAGAAAAGCATGGGGAGGAAG
AGGGCCTACTTGGCGAGAGCCAAGATCAAGGCCGGAAGCAGCAACGCCAG
CGATCGGCCCAAAAATGGCGTACAATTACCCTAGTATCCCTGCTGGGCGC
TTTCGCCCTGTTTGTGTACTTCGCGAAGGGGTCCCAGTGCAACCGCCCCC
CCTCGCATGTCACAACCCAGCCCGACCTACCTGTGGCTTTTCCCCTGAAC
AAGTCGAAGCGATCATCGCATCACGAACATGCCTGCAATACTGTTGATGG
CGGTTATCAATGCAACTCCTCGCTCTCACACAAGTGGGGCCAATATTCGC
CCTATTTCTCTCTTTCTGACGAATCGGCCATCTCAGATGAGGTACCTCAC
GGTTGTCAGATCACTTTTGCTCAGGTGATCTCCCGTCATGGTGCTCGATT
CCCGTCGGCGAAAAAGAGCAAGGCATATGCCGCGCTCGTTAAAAGCATCC
AAGCGAACGCGACTTCATACAAGGGCAACACGGAATTCATCCGCTCATAC
AACTACACCATGGGCGGTGATGATTTGGTACCTTTGGAGTGAACCAGATG
GTGAGCTCGGGAACAAGTTCTACCAGCGCTATGCGGCGTTASSTAAAAAG
GCCGTGCTTTCATTCGCATATCTGACTCGGAGCGGGTTGTGGCTTCAGGA

(SEQ ID NO: 21)

HHXREKKLGTGPPLEVDGIDKLDSAPVEEDQPAGSKHSRAQPPQGVNPNA
LEPGRNLKMX*FPPLRIRYPCRFHVLVVIPSTHSLGAMAAFSKEKHGEEE
GLLGESQDQGRKQQRQRSAQKWRTITLVSLLGAFALFVYFAKGSQCNRPP
SHVTTQPDLPVAFPLNKSKRSSHHEHACNTVDGGYQCNSSLSHKWGQYSP
YFSLSDESAISDEVPHGCQITFAQVISRHGARFPSAKKSKAYAALVKSIQ
**ANATSYKGNTEFIRSYNYTMGGDDLVPLE*TRW*AREQVLPALCGVX*KG**
RAFIRISDSERVVASG

*FIG._10B*

*Aspergillus awamori* glaA Promoter: (Spe1-Bgl II Fragment):
Bases 1-1134
Multiple Cloning site: Bases 1135-1227 (Bgl II to Xba1)
*Aspergillus niger* glaA Terminator (Xba1-EcoRV Fragment):
Bases 1227-1485 and 3079-3100
*A. nidulans* pryG PCR gene (Forward direction): Bases 1486-3078

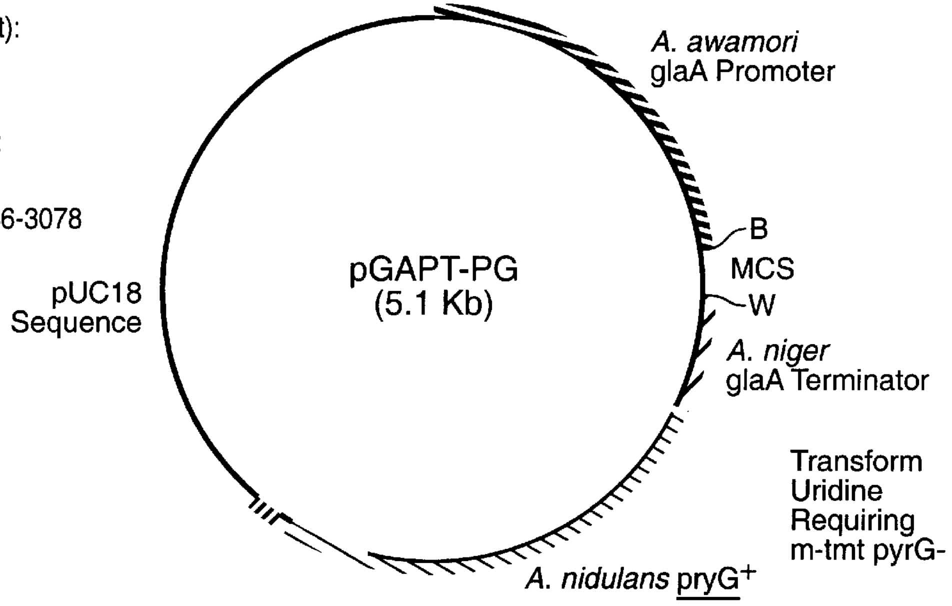

(SEQ ID NO: 22)

Multiple Cloning Sites (Unique Restriction Sites):

Bgl II, BssH II, EcoRV, Nco I

AGATCTTCGAATGCATCGCGCGCACCGTACGTCTCGAGGAATTCCTGCAGGATATCTGGATCCACGAAGCTTCCC

TCTAGAAGCTTACGTAGCGCGCGTGGCATGCAGAGCTCCTTAAGGACGTCCTATAGACCTAGGTGCTTCGAAGGG

Aat II, Age I, Xba I

TGGTGACGTCACCGGTTCTAG

ACCACTGCAGTGGCCAAGATC

FIG._11

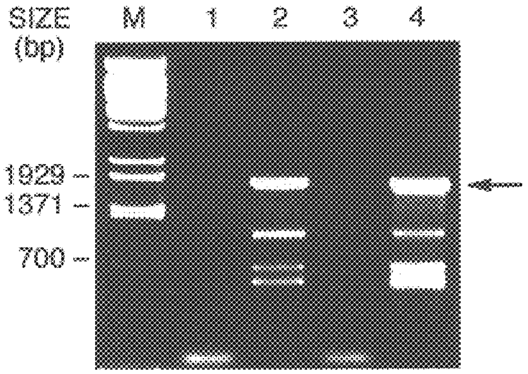
FIG._12
Marker lane - Amresco E261 Standards
Lane 1 Primers CS202/203, 54°C
Lane 2 Primers CS201/203, 54°C
Lane 3 Primers CS202/203, 52°C
Lane 4 Primers CS201/203, 52°C
Note band at expected size 1.7 kb with primers CS201/203.
Also note presence of multiple bands.
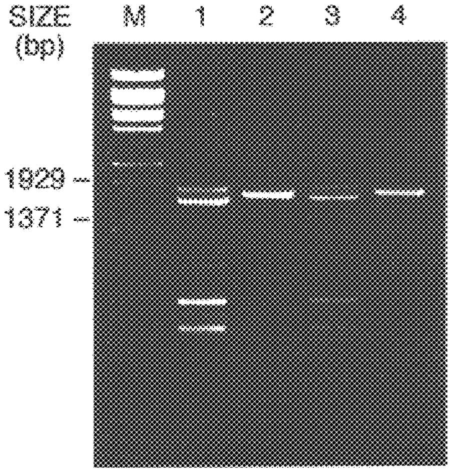
FIG._13
Marker lane - Amresco E261 Marker
Lane 1 Primers CS22/CS203, 56°C
Lane 2 Primers CS22/CS204, 56°C
Lane 3 Primers CS23/CS203, 56°C
Lane 4 Primers CS23/CS204, 56°C

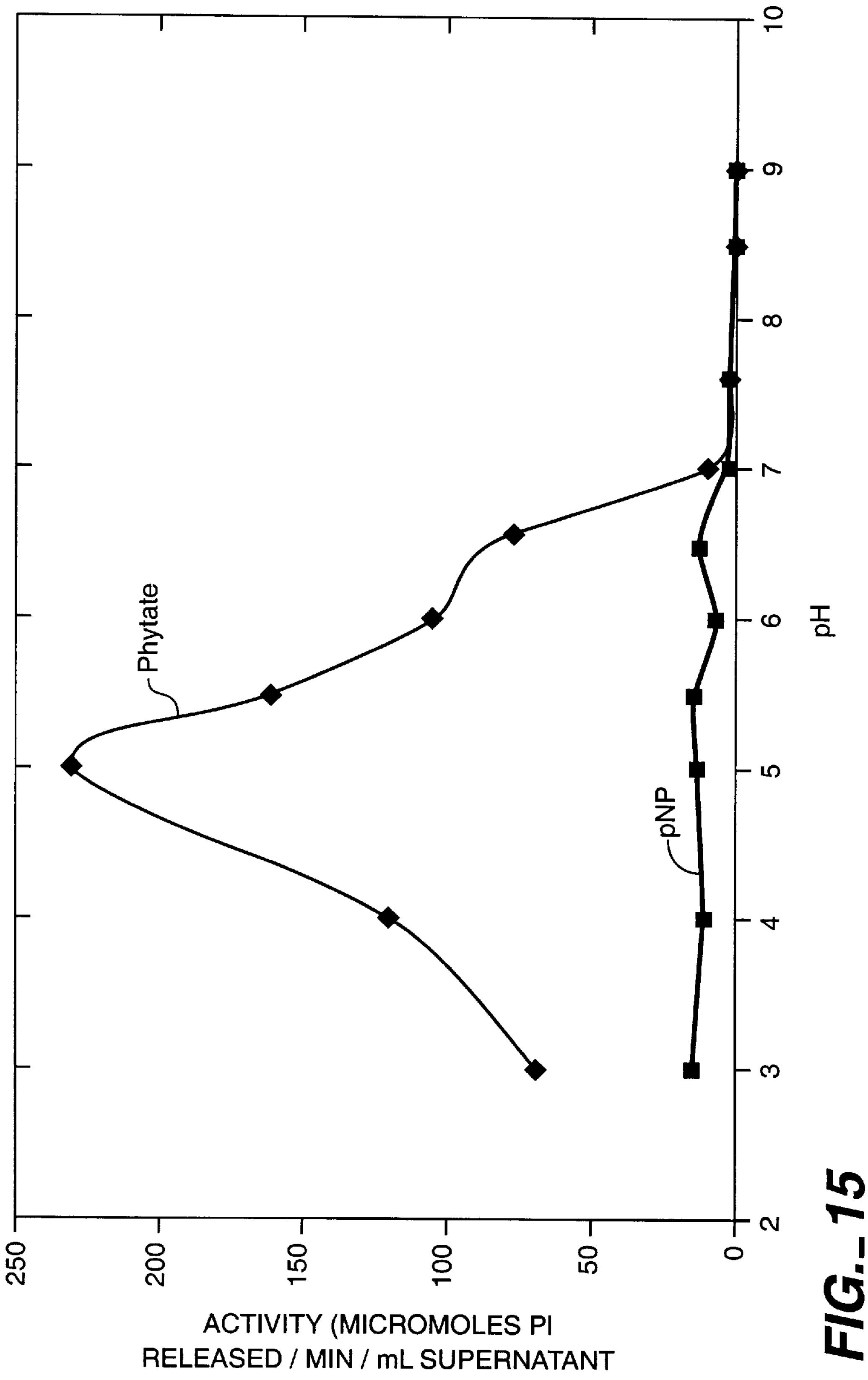
FIG._15

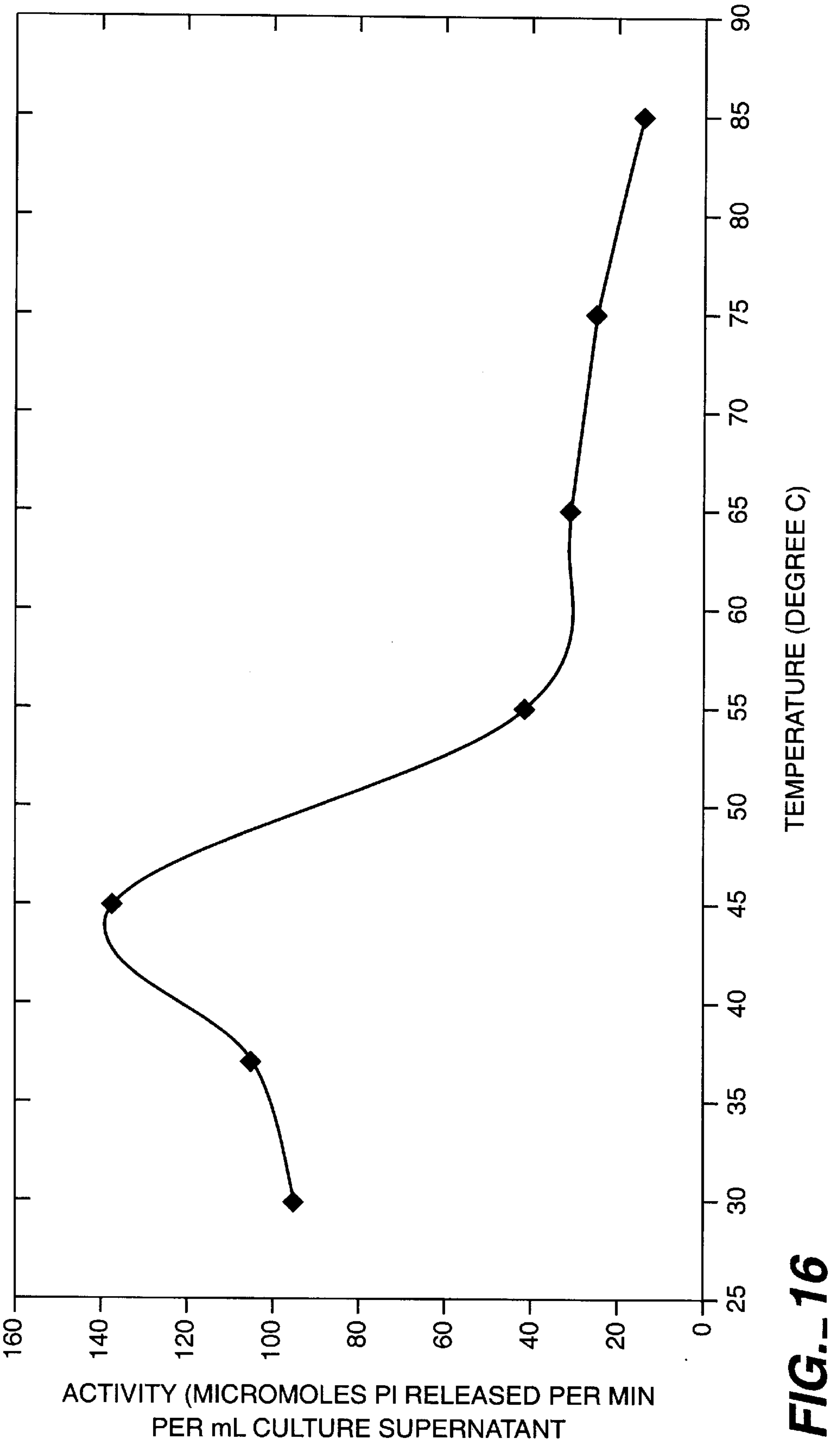
FIG._16

(SEQ ID NO: 23)

ATTCGGCATG
GCGCGCGGTATCCGACTTCGTACAAGGATGAGAAATATGCAGAACTTGTT
GATAACATCCACAAGACTGCAACAGCGTATATGGGCGACTTTTCTGTTTT
GAAGGACTACAAGTACCAACTAGGAGCCAATAACCTGACGGAGCTCGGCC
AACAGCAGTTAATTGTCTCTGGAATGAGGTTCTATGAGCGATACAGGAGC
CTTGCTCGCGATAACGTGCCATTTGTTCGTTCCGCGGGCTCCACCCGGGT
TGTTGCGTCTGGCGACTTTTTCAATCAGGGATTTCAAGCTGCAAAGGATC
GTGATCCAGTATCGAATAAGACTCAACAGCCACCGGTTATCAACGTTATC
ATACCAGAGGGTAGCCAGTGGAATAATACGCTGGACGTCACTACTTGTCC
GTCTTTTCAAAATGACACATCGGCAGACACAGCACAAGAGAAGTTTCTCA
ATGTTTTCGCTCCTTCAATCCTCCAGAAAATCACGGCTGGTCTTCCCGGT
ACACAACTGAAGGTTGAAGATGTCCCTCTGATCATGGATCTGTGTCCATT
TGAAACCGTGGCGAATCCCAATACCAGCACCCAGTTGTCTCCCCTGTGCG
ACTTATTCACACTGTCCGAATGGCAATCGTACGATTACTACAACACTCTC
GGGAAATATTACGGACATGGTCAGGGTAACCCTTTGGGTCCGACACAGGG
AGTCGGATTTGTGAATGAAGTGATTGCTCGCATGACCCAGTCCCCAGTCA
AGGACCACACCAGTGTCAACAACACACTCGATTCCGATGCGACAACTTTC
CCTCTGGGGCCAGCGCTATACGCAGATTTCCCACATGACAACA

(SEQ ID NO: 24)

RHGARYPTSYKDEKYAELVDNIHKTATAYMGDFSVLKDYKYQLGANNLTELGQQQLIVSGMRFYERYRSLA
RDNVPFVRSAGSTRVVASGDFFNQGFQAAKDRDPVSNKTQQPPVINVIIPEGSQWNNTLDVTTCPSFQNDT
SADTAQEKFLNVFAPSILQKITAGLPGTQLKVEDVPLIMDLCPFETVANPNTSTQLSPLCDLFTLSEWQSY
DYYNTLGKYYGHGQGNPLGPTQGVGFVNEVIARMTQSPVKDHTSVNNTLDSDATTFPLGPALYADFPHDN

Motifs critical for phytase structure and function and Cys residues important for structure within this sequence are in bold.

*FIG._17*

PHYTASE ENZYMES NUCLEIC ACIDS ENCODING PHYTASE ENZYMES AND VECTORS AND HOST CELLS INCORPORATING SAME

RELATED APPLICATIONS

The present application claims priority to U.S. Provisional Patent Application No. 60/148,960 filed Aug. 13, 1999, which is hereby incorporated by reference in its entirety.

FIELD OF THE INVENTION

The present invention relates to phytase, nucleic acids encoding phytase, as well as the production of phytase and its use.

REFERENCES

Altschul, S. F., Gish, W., Miller, W., Myers, E. W. & Lipman, D. J. (1990) "Basic local alignment search tool." J. Mol. Biol. 215:403–410.

Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402.

Ausubel et al. (eds.), Current Protocols In Molecular Biology, Vol. 1, John Wiley & Sons, Inc. 1987.

Benton, W. and Davis, R., 1977, *Science* 196:180.

Berger and Kimmel, 1987, Guide to Molecular Cloning Techniques, Methods in Enzymology, Vol. 152, Academic Press, San Diego Calif.

Bimboim, H. C. and Doly, J. (1979). *Nucleic Acids Research* 7: 1513–23.

Botstein, D. and Shortle, D., 1985, Science 229:1193–1201.

Brisson et al (1984) Nature 310:511–514.

Broglie et al (1984) Science 224:838–843).

Cadwell, R. C. and Joyce, G. F., 1992, PCR Methods Applic. 2: 28–33.

Coruzzi et al (1984) EMBO J 3:1671–1680.

Cromwell, G. L. T., T. S. Stahly, R. D. Coffey, H. J. Monegue, and J. H. Randolph. 1993. Efficacy of phytase in improving bioavailability of phosphorus in soybean and corn-soybean meal diets for pigs. J. Anim. Sci. 71:1831.

Dayhoff, M. O., Schwartz, R. M. & Orcutt, B. C. (1978) "A model of evolutionary change in proteins." In "Atlas of Protein Sequence and Structure, vol. 5, suppl. 3." M. O. Dayhoff (ed.), pp. 345–352, Natl. Biomed. Res. Found., Washington, D.C.

Deutscher, *Methods in Enzymology*, 182 (1990).

Dieffenbach C W and Dveksler G S, 1995, PCR Primer, a Laboratory Manual, Cold Spring Harbor Press, Plainview N.Y.

Eckert, K. A. and Kunkel, T. A., 1991, PCR Methods Applic. 1: 17–24.

Ehrlich, K. C., Montalbano, B. G., Mullaney, E. J., Dischinger Jnr., H. C. & Ullah, A. H. J. (1993). Identification and cloning of a second phytase gene (phy B) from *Aspergillus niger* (*ficuum*). *Biochemical and Biophysical Research Communications* 195, 53–57.

Elander, R. P., Microbial screening, Selection and Strain Improvement, in Basic Biotechnology, J. Bullock and B. Kristiansen Eds., Academic Press, New York, 1987, 217.

Finkelstein, D B 1992 Transformation. In Biotechnology of Filamentous Fungi. Technology and Products (eds by Finkelstein & Bill) 113–156.

Fiske, C. H. and SubbaRow, Y. (1925). *Journal of Biological Chemistry* 66:375–392.

Fungaro et al. (1995) Transformation of *Aspergillus nidulans* by microprojection bombardment on intact conidia, FEMS Microbiology Letters 125 293–298.

Gish, W. & States, D. J. (1993) "Identification of protein coding regions by database similarity search." Nature Genet. 3:266–272.

Glover, D M and Hames, B D (Eds.), DNA Cloning: A Practical Approach, Vols 1 and 2, Second Edition.

Groot et al. (1998) Agrobacterium tumefaciens-mediated transformation of filamentous fungi, Nature Biotechnology 16 839–842.

Grunstein, M. and Hogness, D., 1975, *Proc. Natl. Acad. Sci. USA* 72:3961.

Hale & Marham, *THE HARPER COLLINS DICTIONARY OF BIOLOGY*, Harper Perennial, N.Y. (1991).

Henikoff & Henikoff, *Proc. Natl. Acad. Sci. USA* 89:10915 (1989).

Higgins D. G., Bleasby A. J., Fuchs R. (1992) CLUSTAL V: improved software for multiple sequence alignment. Comput. Appl. Biosci. 8:189–191.

Hobbs S or Murry L E (1992) in McGraw Hill Yearbook of Science and Technology, McGraw Hill, New York, N.Y., pp 191–196.

Karlin & Altschul, *Proc. Nat'l. Acad. Sci. USA* 90:5873–5787 (1993).

Kerovuo, J., Lauraeus, M., Nurminen, P., Kalkkinen, N., Apajalahti, J. (1988) Isolation, characterization and molecular gene cloning, and sequencing of a novel phytase from *Bacillus subtilis*. Appl. Environ. Micro., 64, 6, 2079–2085.

Kornegay, E. T., D. M. Denbow, Z. Yi., and V. Ravindran. 1996. Response of broilers to graded levels of Natuphosa phytase added to corn-soybean meal-based diets containing three levels of nonphytate phosphorus. Br. J. Nutr.

Leung, D. W., Chen, E., and Goeddel, D. V., 1989, Technique 1: 11–15.

Madden, T. L., Tatusov, R. L. & Zhang, J. (1996) "Applications of network BLAST server" Meth. Enzymol. 266:131–141.

Myers, R. M., Lerman, L. S., and Maniatis, T., 1985, Science 229: 242–247.

Mitchell, D. B., Vogel, K., Weimann, B. J., Pasamontes, L. and van Loon, A. P., The phytase subfamily of histidine acid phosphatases: isolation of genes for two novel phytases from the fungi *Aspergillus terreus* and *Myceliophthora thermophila*, Microbiology 143 (Pt 1), 245–252 (1997)).

Mullis, Kary B., U.S. Pat. No. 4,683,202 (1990).

Needleman & Wunsch, *J. Mol. Biol.* 48:443 (1970).

Pasamontes, L., Haiker, M., Henriquez-Huecas, M., Mitchell, D. B. and van Loon, A. P., Cloning of the phytases from *Emericella nidulans* and the thermophilic fungus *Talaromyces thermophilus*, Biochim. Biophys. Acta 1353 (3), 217–223 (1997).

Pasamontes, L., Haiker, M., Wyss, M., Tessier, M. and van Loon, A. P., Gene cloning, purification, and characterization of a heat-stable phytase from the fungus *Aspergillus fumigatus*, Appl. Environ. Microbiol. 63 (5), 1696–1700 (1997).

Pearson & Lipman, *Proc. Nat'l. Acad. Sci. USA* 85:2444 (1988).

Piddington, C. S., Houston, C. S., Paloheimo, M., Cantrell, M., Miettinen-Oinonen, A., Nevalainen, H. &

Rambosek, J. (1993). The cloning and sequencing of the genes encoding phytase (phy) and pH 2.5-optimum acid phosphatase (aph) from *Aspergillus niger* var. awamori. *Gene* 133, 55–62.

Powar, V. K. and Jagannathan V., (1982) J. Bacteriology, 151 (3), 1102–1108.

Sambrook, J., Fritsch, E. F. and Maniatis, T. (1989). *Molecular Cloning—A Laboratory Manual*, $2^{nd}$ Ed. Cold Spring Harbour Press.

Sanchez, O. and J. Aguirre. 1996. Efficient transformation of *Aspergillus nidulans* by electroporation of germinated conidia. Fungal Genetics Newsletter 43: 48–51.

Sanger, F., Nilken, S. and Coulson, A. R. (1977). *Proceedings of the National Academy of Science USA*, 74: 5463–5467.

Schwartz, R. M. & Dayhoff, M. O. (1978) "Matrices for detecting distant relationships." In "Atlas of Protein Sequence and Structure, vol. 5, suppl. 3." M. O. Dayhoff (ed.), pp. 353–358, Natl. Biomed. Res. Found., Washington, D.C.

Scopes, Protein Purification: Principles and Practice, Springer-Verlag, New York (1982).

Shimizu, M., (1992) Biosci. Biotech. Biochem., 56 (8), 1266–1269.

Shimizu, M., Japanese Patent Application 6-38745 (1994).

Singleton, et al., *DICTIONARY OF MICROBIOLOGY AND MOLECULAR BIOLOGY*, 2D ED., John Wiley and Sons, New York (1994).

Smith & Waterman, *Adv. Appl. Math.* 2:482 (1981).

Takamatsu et al (1987) EMBO J 6:307–311.

Ullah, H. J. and Gibson, D. M., Preparative Biochemistry, 17 (1) (1987), 63–91.

van Gorcom, Robert Franciscus Maria; van Hartingsveldt, Willem; van Paridon, Peter Andreas; Veenstra, Annemarie Eveline; Luiten, Rudolf Gijsbertus Marie; Selten, Gerardus Cornelis Maria; EP 420 358 (1991).

van Hartingsveldt, W., van Zeijl, C. M. J., Harteveld, G. M., Gouka, R. J., Suykerbuyk, M. E. G., Luiten, R. G. M., van Paridon, P. A., Selten, C. G. M., Veenstra, A. E., van Gorcom, R. F. M. & van den Hondel, C. A. J. J. (1993). Cloning, characterisation and overexpression of the phytase-encoding gene (phyA) of *Aspergillus niger*. Gene 127:87–94.

Van Loon, A. and Mitchell, D.; EP 684 313 (1995).

Weidner, G., d'Enfert, C., Koch, A., Mol, P., and Brakhage, A. A. (1998) Development of a homologous transformation system for the human pathogenic fungus *Aspergillus fumigatus* based on the pyrG gene encoding orotidine monophosphate decarboxylase. Current Genet. 33: 378–385.

Weissbach and Weissbach (1988) Methods for Plant Molecular Biology, Academic Press, New York, N.Y., pp 421–463.

Winter J and Sinibaldi R M (1991) Results Probl Cell Differ 17:85–105.

Yamada et al., Agr. Biol. Chem., 32 (10) (1968), 1275–1282.

BACKGROUND OF THE INVENTION

Phosphorous (P) is an essential element for growth. A substantial amount of the phosphorous found in conventional livestock feed, e.g., cereal grains, oil seed meal, and by products that originate from seeds, is in the form of phosphate which is covalently bound in a molecule know as phytate (myo-inositol hexakisphosphate). The bioavailability of phosphorus in this form is generally quite low for non-ruminants, such as poultry and swine, because they lack digestive enzymes for separating phosphorus from the phytate molecule.

Several important consequences of the inability of non-ruminants to utilize phytate may be noted. For example, expense is incurred when inorganic phosphorus (e.g., dicalcium phosphate, defluorinated phosphate) or animal products (e.g., meat and bone meal, fish meal) are added to meet the animals' nutritional requirements for phosphorus. Additonally, phytate can bind or chelate a number of minerals (e.g., calcium, zinc, iron, magnesium, copper) in the gastrointestinal tract, thereby rendering them unavailable for absorption. Still further, most of the phytate present in feed passes through the gastrointestinal tract, elevating the amount of phorphorous in the manure. This leads to an increased ecological phosphorous burden on the environment.

Ruminants, such as cattle, in contrast, readily utilize phytate thanks to an enzyme produced by rumen microorganisms known as phytase. Phytase catalyzes the hydrolysis of phytate to (1) myo-inositol and/or (2) mono-, di-, tri-, tetra- and/or penta-phosphates thereof and (3) inorganic phosphate. Two different types of phytases are known: (1) a so-called 3-phytase (myo-inositol hexaphosphate 3-phosphohydrolase, EC 3.1.3.8) and (2) a so-called 6-phytase (myo-inositol hexaphosphate 6-phosphohydrolase, EC 3.1.3.26). The 3-phytase hydrolyses first the ester bond at the 3-position, whereas the 6-phytase hydrolyzes first the ester bond at the 6-position.

Microbial phytase, as a feed additive, has been found to improve the bioavailability of phytate phosphorous in typical non-ruminant diets (See, e.g., Cromwell, et al, 1993). The result is a decreased need to add inorganic phosphorous to animal feeds, as well as lower phosphorous levels in the excreted manure (See, e.g., Kornegay, et al, 1996).

Despite such advantages, few of the known phytases have gained widespread acceptance in the feed industry. The reasons for this vary from enzyme to enzyme. Typical concerns relate to high manufacture costs, and/or poor stability/activity of the enzyme in the environment of the desired application (e.g., the pH/temperature encountered in the processing of feedstuffs, or in the digestive tracts of animals).

It is, thus, generally desirable to discover and develop novel enzymes having good stability and phytase activity for use in connection with animal feed, and to apply advancements in fermentation technology to the production of such enzymes in order to make them commercially viable. It is also desirable to ascertain nucleotide sequences which can be used to produce more efficient genetically engineered organisms capable of expressing such phytases in quantities suitable for industrial production. It is still further desirable to develop a phytase expression system via genetic engineering which will enable the purification and utilization of working quantities of relatively pure enzyme.

SUMMARY OF THE INVENTION

The present invention provides for a purified enzyme having phytase activity which is derived from a microbial source, and preferably from a fungal source, such as a Penicillium species, e.g., *P. hordei* (formerly *P. hirsutum*; ATCC No. 22053), *P. piceum* (ATCC No. 10519), or *P. brevi-compactum* (ATCC No. 48944).

The present invention further provides a polynucleotide sequence coding for the enzyme comprising a DNA as shown in any one of FIGS. 1A–1C; a polynucleotide which encodes the amino acid sequence shown in FIG. 2; a polynucleotide which encodes a phytase which comprises an amino acid segment which differs from the sequence in FIG. 2, provided that the polynucleotide encodes a derivative of the phytase specifically described herein; and a polynucleotide which encodes a phytase that comprises an amino acid segment which differs from the sequence in FIG. 2, provided that the polynucleotide hybridizes under medium to high stringency conditions with a DNA comprising all or part of the DNA in any one of FIGS. 1A–1C (SEQ ID NOs 1–3).

The present invention also provides a polynucleotide encoding an enzyme having phytate hydrolyzing activity and including a nucleotide sequence as shown in FIG. 17 (SEQ ID NO:23); a polynucleotide which encodes the amino acid sequence shown in FIG. 17 (SEQ ID NO:24); a polynucleotide which encodes a phytase which comprises an amino acid segment which differs from the sequence in FIG. 17 (SEQ ID NO:23), provided that the polynucleotide encodes a derivative of the phytase specifically described herein; and a polynucleotide which encodes a phytase that comprises an amino acid segment which differs from the sequence in FIG. 17 (SEQ ID NO:24), provided that the polynucleotide hybridizes under medium to high stringency conditions with a nucleotide sequence as shown in FIG. 17 (SEQ ID NO:23).

Additionally, the present invention encompasses vectors which include the polynucleotide sequences described above, host cells which have been transformed with such polynucleotide or vectors, fermentation broths comprising such host cells and phytase proteins encoded by such polynucleotide which are expressed by the host cells. Preferably, the polynucleotide of the invention is in purified or isolated form and is used to prepare a transformed host cell capable of producing the encoded protein product thereof. Additionally, polypeptides which are the expression product of the polynucleotide sequences described above are within the scope of the present invention.

In one embodiment, the present invention provides an isolated or purified polynucleotide derived from a fungal source of the genus Penicillium, which polynucleotide comprises a nucleotide sequence encoding an enzyme having phytase activity. The fungal source can be selected, for example, from the group consisting of Penicillium piceum and Penicillium hordei.

According to one embodiment, the polynucleotide encodes an phytate-hydrolyzing enzyme including an amino acid sequence having at least 55%, at least 60%, at least 65%, at least 70%, at least 75%, at least 80%, at least 85%, at least 90%, at least 95%, and/or about 100% identity to an amino acid sequence as disclosed in SEQ ID NO: 4.

One embodiment of the present invention provides an isolated polynucleotide comprising a nucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in SEQ ID NO: 1, SEQ ID NO:2, or SEQ ID NO:3, or (ii) being capable of hybridizing to a probe derived from the nucleotide sequence disclosed in SEQ ID NO: 1, SEQ ID NO:2, or SEQ ID NO:3 under conditions of intermediate to high stringency, or (iii) being complementary to the nucleotide sequence disclosed in SEQ ID NO:1, SEQ ID NO:2, or SEQ ID NO:3.

Another aspect of the present invention provides an isolated polynucleotide encoding an enzyme having phytase activity, wherein the enzyme is derived from a Penicillium source. The source can be selected, for example, from the group consisting of *Penicillium piceum* and *Penicillium hordei.*

In one embodiment, the polynucleotide encodes a phytate-hydrolyzing enzyme that includes an amino acid sequence having at least 55%, at least 60%, at least 65%, at least 70%, at least 75%, at least 80%, at least 85%, at least 90%, at least 95%, and/or about 100% identity to an amino acid sequence as disclosed in SEQ ID NO: 4.

In another embodiment, the polynucleotide has at least 55%, at least 60%, at least 65%, at least 70%, at least 75%, at least 80%, at least 85%, at least 90%, at least 95%, and/or about 100% identity to a nucleotide sequence as disclosed in SEQ ID NO: 1, SEQ ID NO:2, or SEQ ID NO:3, or (ii) is capable of hybridizing to a probe derived from the nucleotide sequence disclosed in SEQ ID NO: 1, SEQ ID NO:2, or SEQ ID NO:3 under conditions of medium to high stringency, or (iii) is complementary to the nucleotide sequence disclosed in SEQ ID NO:1, SEQ ID NO:2, or SEQ ID NO:3.

Yet a further aspect of the present invention provides an expression construct including a polynucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in SEQ ID NO: 1, SEQ ID NO:2, or SEQ ID NO:3, or (ii) being capable of hybridizing to a probe derived from the nucleotide sequence disclosed in SEQ ID NO: 1, SEQ ID NO:2, or SEQ ID NO:3 under conditions of medium to high stringency, or (iii) being complementary to the nucleotide sequence disclosed in SEQ ID NO:1, SEQ ID NO:2, or SEQ ID NO:3. Also provided are a vector (e.g., a plasmid) including such expression construct, and a host cell (such as an Aspergillus, e.g., *Aspergillus niger* or *Aspergillus nidulans*) transformed with such a vector.

In another of its aspects, the present invention provides a probe for use in detecting nucleic acid sequences coding for an enzyme having phytase activity derived from a microbial source, comprising: a nucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in SEQ ID NO: 1, SEQ ID NO:2, or SEQ ID NO:3, or (ii) being capable of hybridizing to a polynucleotide including a sequence as disclosed in SEQ ID NO: 1, SEQ ID NO:2, or SEQ ID NO:3 under conditions of medium to high stringency, or (iii) being complementary to the nucleotide sequence disclosed in SEQ ID NO:1, SEQ ID NO:2, or SEQ ID NO:3.

In one embodiment, the microbial source is a fungal source, e.g., a Penicillium species, such as *Penicillium hordei* or *Penicillium piceum.*

The present invention additionally provides a food or animal feed including an enzyme having phytase activity, wherein the enzyme comprises an amino acid sequence having at least 55%, at least 60%, at least 65%, at least 70%, at least 75%, at least 80%, at least 85%, at least 90%, at least 95%, and/or about 100% identity to an amino acid sequence as disclosed in SEQ ID NO: 4.

The present invention provides food or animal feed including an enzyme having phytase activity, wherein the enzyme is derived from a fungal source selected from the group consisting of *Penicillium hordei* and *Penicillium piceum.*

One aspect of the present invention provides an isolated phytase enzyme wherein the enzyme is obtained from a fungus selected from the group consisting of *P. piceum* and *P. hordei*, and has the following physiochemical properties: (1) Molecular weight: between about 45–55 kDa (non-glycosylated); and (2) Specificity: phytate.

In one embodiment, the present invention provides an enzyme derived from a fungal species (e.g., a Penicillium, such as *P. piceum* and *P. hordei*), or encoded by a nucleotide sequence capable of hybridising to SEQ ID NO. 1, SEQ ID NO. 2, SEQ ID NO. 3, or the polynucleotide sequence of FIG. 17 (SEQ ID NO:23) under conditions of intermediate to high stringency, and having one or more of the following physiochemical properties:

(1) Molecular weight: between about 45–60 kDa (non-glycosylated) [based on a protein of 489 amino acids];

(2) An activity that is specific towards phytate, phytic acid or myo-inositol hexaphosphate, and/or lower phosphate derivatives thereof;

(3) A theoretical pI of between about 7 and 7.6; e.g., 7.3;

(4) A pH optimum within a range of about 4.5–5.5, e.g., about 5; and/or (5) An ambient temperature optimum of 40–45 degree C., e.g, 42–44 degree C.

Another aspect of the present invention provides a method of producing an enzyme having phytase activity, comprising:

(a) providing a host cell transformed with an expression vector comprising a polynucleotide as described herein;

(b) cultivating the transformed host cell under conditions suitable for the host cell to produce the phytase; and (c) recovering the phytase.

According to one embodiment, the host cell is an Aspergillus species, such as *A. niger* or *A. nidulans.*

In another of its aspects, the present invention provides a method of separating phosphorous from phytate, comprising the step of treating the phytate with an enzyme comprising an amino acid sequence having at least 55%, at least 60%, at least 65%, at least 70%, at least 75%, at least 80%, at least 85%, at least 90%, at least 95%, and/or about 100% identity to an amino acid sequence as disclosed in SEQ ID NO: 4.

The present invention further provides a method of separating phosphorous from phytate, comprising the step of treating the phytate with an enzyme as defined above.

Another aspect of the present invention provides a phytate-hydrolyzing enzyme that includes an amino acid sequence having at least 55%, at least 60%, at least 65%, at least 70%, at least 75%, at least 80%, at least 85%, at least 90%, at least 95%, and/or about 100% identity to an amino acid sequence as disclosed in FIG. 17.

A further aspect of the present invention provides an isolated polynucleotide including a nucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in FIG. 17, or (ii) being capable of hybridizing to a probe derived from the nucleotide sequence disclosed in FIG. 17 (SEQ ID NO:23) under conditions of intermediate to high stringency, or (iii) being complementary to the nucleotide sequence disclosed in FIG. 17 (SEQ ID NO:23).

In one embodiment, the isolated polynucleotide encodes a phytate-hydrolyzing enzyme derived from *Penicillium piceum* or *Penicillium hordei*. The enzyme includes, according to one embodiment, an amino acid sequence having at least 55%, at least 60%, at least 65%, at least 70%, at least 75%, at least 80%, at least 85%, at least 90%, at least 95%, and/or about 100% identity to an amino acid sequence as disclosed in FIG. 17.

In another embodiment, the polynucleotide includes a nucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in FIG. 17 (SEQ ID NO:23), or (ii) capable of hybridizing to a probe derived from the nucleotide sequence disclosed in FIG. 17 (SEQ ID NO:23) under conditions of medium to high stringency, or (iii) complementary to the nucleotide sequence disclosed in FIG. 17 (SEQ ID NO:23).

Another aspect of the present invention provides an expression construct comprising a polynucleotide including a nucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in FIG. 17 (SEQ ID NO:23), or (ii) being capable of hybridizing to a probe derived from the nucleotide sequence disclosed in FIG. 17 (SEQ ID NO:23) under conditions of medium to high stringency, or (iii) being complementary to the nucleotide sequence disclosed in FIG. 17 (SEQ ID NO:23). The present invention further provides a vector (e.g., plasmid) including such an expression construct, as well as a host cell (e.g., *Aspergillus niger* or *Aspergillus nigulans*) transformed with such a vector.

The present invention additionally provides a probe for use in detecting nucleic acid sequences coding for an enzyme having phytase activity derived from a microbial source, comprising: a nucleotide sequence (i) having at least 55%, at least 60%, at least 65%, at least 70%, at least 75%, at least 80%, at least 85%, at least 90%, at least 95%, and/or about 100% identity to a nucleotide sequence as disclosed in FIG. 17 (SEQ ID NO:23), or (ii) being capable of hybridizing to a polynucleotide including a sequence as disclosed in FIG. 17 (SEQ ID NO:23) under conditions of medium to high stringency, or (iii) being complementary to the nucleotide sequence disclosed in FIG. 17 (SEQ ID NO:23).

In one embodiment, the microbial source is a fungal source, e.g., a Penicillium species, such as *P. hordei* or *P. piceum.*

The present invention further provides a food or animal feed including an enzyme having phytase activity, wherein the enzyme includes an amino acid sequence having at least 55%, at least 60%, at least 65%, at least 70%, at least 75%, at least 80%, at least 85%, at least 90%, at least 95%, and/or about 100% identity to an amino acid sequence as disclosed in FIG. 17 (SEQ ID NO:24).

Still further, the present invention provides a method of separating phosphorous from phytate, comprising the step of treating the phytate with an enzyme (i) having phytate hydrolyzing activity and (ii) including an amino acid sequence having at least 55%, at least 60%, at least 65%, at least 70%, at least 75%, at least 80%, at least 85%, at least 90%, at least 95%, and/or about 100% identity to an amino acid sequence as disclosed in FIG. 17 (SEQ ID NO:24).

As will be appreciated, an advantage of the present invention is that a polynucleotide has been isolated which provides the capability of isolating further polynucleotides which encode proteins having phytase activity.

Another advantage of the present invention is that, by virtue of providing a polynucleotide encoding a protein having phytase activity, it is possible to produce through recombinant means a host cell which is capable of producing the protein having phytase activity in relatively large quantities.

Yet another advantage of the present invention is that commercial application of proteins having phytase activity is made practical. For example, the present invention provides animal feed incorporating the phytase described herein.

Still a further advantage of the present invention is that it provides an enzyme having phytate hydrolyzing activity, with such activity being optimum at temperatures from about 40 to about 45 degrees C, which make it very suitable to for use in animal feed (i.e., the enzyme has high activity at the point of action, in the gut of an animal).

Other objects and advantages of the present invention will become apparent from the following detailed specification.

BRIEF DESCRIPTION OF THE DRAWINGS

FIG. 1A illustrates a nucleic acid sequence (SEQ. ID NO:1) corresponding to a gene encoding a phytase hydrolyzing enzyme derived from *Penicillium hordei*, with the following features highlighted: an ATG start codon (bold) for Met of phytase; an intron (lower case); and a TAG stop codon (bold). Notably, two exons (120 bp and 1347 bp) are shown, separated by 5' intron 120 bp long.

FIG. 1B shows the contiguous region of the sequence of FIG. 1A between the start (ATG) and stop (TAG) codons (SEQ ID NO:2).

FIG. 1C shows, as a contiguous sequence, the region of the sequence of FIG. 1A between the start and stop codons, with the 120 bp intron removed (SEQ ID NO:3).

FIG. 2 illustrates the amino acid sequence (SEQ ID NO:4) encoded by the nucleic acid sequence of FIG. 1.

FIGS. 3 and 4 are growth curves for *P. piceum* and *P. hordei*, respectively, showing the effect of available P in the medium on growth over time.

FIG. 5A shows an alignment for four published fungal phytase amino acid sequences (SEQ ID NO:5–8), showing conserved regions (highlighted in black border) used to design degenerate primers for PCR.

FIGS. 5B-1 and 5B-2 show an alignment for the four published fungal phytase amino acid sequences of FIG. 5A (SEQ ID NO:5–8), along with the sequence of the *P.hordei* and *P.piceum* sequences of the present invention (SEQ ID NO. 9 and SEQ ID NO. 10, respectively).

FIG. 6 shows an alignment of published amino acid sequences for phyA and phyB phytases from *A.niger* (SEQ ID NO:11–14), from which degenerate primers CS1 and CS2 were designed. Conserved sequences used to design primers CS1, CS2 are shown.

FIGS. 7A and 7B show the amino acid sequences for four published fungal phytases (SEQ ID NO:5–8) aligned with (i) the translated amino acid sequence from the PCR product obtained using primers CS1 and CS2 (line 2, denoted as "*P.hordei*3D) (SEQ ID NO:16), and (ii) the translated amino acid sequence from approx. 80% of the *P. hordei* phytase gene (i.e., N-terminal portion missing) obtained from the first *P. hordei* genomic library (line 1, denoted has "*P hordei* (SEQ ID NO:15)").

FIG. 8 illustrates a Southern blot gel showing hybridization between a probe comprising the PCR product obtained using degenerate primers CS1 and CS2 and various digests of fungal genomic DNA; with: Lane 1—Size marker; Lane 2—*Aspergillus niger*—EcoRI; Lane 3—*Penicillium piceum*—EcoRI; Lane 4—*Penicillium hordei*—EcoRI; Lane 5—*Penicillium hordei*—BamHl; Lane 6—*Penicillium hordei*—Sall; Lane 7—*Penicillium hordei*—Kpnl; and, Lane 8—*Penicillium hordei*—Sacl.

FIGS. 9A and 9B illustrate the nucleic acid sequences of a clone, denoted as CS101, obtained upon generating and screening a *P. hordei* genomic library (SEQ ID NO 17). CS101 contains a 4.8 Kb fragment from *P.hordei* in the commercial cloning vector pSK II$^+$ Bluescript (Stratagene; La Jolla, Calif.). 1.7 Kb of this insert sequence is phyA phytase sequence from *P.hordei* and represents 80% of the coding region of the gene (including 3' end), and downstream regulatory regions.

FIGS. 10A and 10B illustrate a 5'/N-terminal nucleic acid sequence (SEQ ID NO. 20) and a 3'/C-terminal sequence (SEQ ID NO. 18) of a clone, denoted as CS158. The deduced amino sequence corresponding to each nucleic acid sequence is also shown (SEQ ID NO. 21and SEQ ID NO. 19, respectively). Clone CS158 was generated by PCR from combination of the primers CS201–204. A band of appropriate size was produced (FIG. 12), cloned and sequenced. The deduced amino sequence is outlined underneath. Preliminary deduced amino acid sequence for phytase is shown in bold. The sequencing of CS158 was incomplete in that there was an approximate gap of 70 amino acids representing the middle of the gene. Reamplification with redesigned primers (FIG. 13) generated full sequence, analysed to be phytase. The C-terminal end of CS158 was shown to be 100% homologous to that from CS101.

FIG. 11 provides an illustration of the vector in pGAPT-PG (SEQ ID NO:22), which can be used for the expression of *P. hordei* phytate hydrolyzing enzyme in Aspergillus.

FIG. 12 shows a PCR amplification of putative phytase gene using primers designed from sequence of genomic phytase clones isolated from *P. hordei.*

FIG. 13 shows a PCR amplification of putative phytase gene using primers designed from the phytase gene sequence of clone CS158.

FIG. 14 shows a Southern Blot analysis of *Aspergillus nidulans* transformed with *P. hordei* phytase gene.

FIG. 15 shows a pH profile of phytase enzyme from *P.hordei.*

FIG. 16 shows a temperature-activity profile of phytase enzyme from *P.hordei.*

FIG. 17 shows the full sequence of an 853 bp fragment (SEQ ID NO. 23) of phytase from *P.piceum* (5'–3'), from a clone denoted as CS142, as well as a deduced amino acid sequence (283 amino acids) (SEQ ID NO. 24). Motifs important for phytase structure and function and Cys residues important for structure within this sequence are in bold.

DETAILED DESCRIPTION OF THE INVENTION

I. Definitions

Unless defined otherwise herein, all technical and scientific terms used herein have the same meaning as commonly understood by one of ordinary skill in the art to which this invention belongs. Singleton, et al., *Dictionary of Microbiology and Molecular Biology*, 2D ED., John Wiley and Sons, New York (1994), and Hale & Marham, *The Harper Collins Dictionary of Biology*, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8, or EC number 3.1.3.26.

The term "identical" in the context of two nucleic acids or polypeptide sequences refers to the residues in the two sequences that are the same when aligned for maximum correspondence, as measured using one of the following sequence comparison or analysis algorithms.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment performed using the CLUSTAL-W program in MACVECTOR, operated in "slow" alignment mode using default parameters, including an open gap penalty of 10.0, an extend gap penalty of 0.1, and a BLOSUM30 similarity matrix. If a gap needs to be inserted into a first sequence to optimally align it with a second sequence, the percent identity is calculated using only the residues that are paired with a corresponding amino acid residue (i.e., the calculation does not consider residues in the second sequences that are in the "gap" of the first sequence).

Optimal alignment of sequences for comparison can also be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical.

Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed.,* 5 Suppl. 3:353–358, National biomedical Research Foundation, Washington, D.C., which adapts the local homology algorithm of Smith and Waterman (1981) Advances in Appl. Math. 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., *J. Mol. Biol.* 215:403–410 (1990). Software for performing BLAST analyses is publicly available through the National Center for Biotechnology Information (http://www.ncbi.nIm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a phytase nucleic acid of this invention if the smallest sum probability in a comparison of the test nucleic acid to a phytase nucleic acid is less than about 0.1, more preferably less than about 0.01, and most preferably less than about 0.001. Where the test nucleic acid encodes a phytase polypeptide, it is considered similar to a specified phytase nucleic acid if the comparison results in a smallest sum probability of less than about 0.5, and more preferably less than about 0.2.

The phrase "substantially identical" in the context of two nucleic acids or polypeptides thus typically means that a polynucleotide or polypeptide comprises a sequence that has at least 60% sequence identity, preferably at least 80%, more preferably at least 90% and most preferably at least 95%, compared to a reference sequence using the programs described above (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

"Hybridization" includes any process by which a strand of a nucleic acid joins with a complementary nucleic acid strand through base-pairing. Thus, strictly speaking, the term refers to the ability of the complement of the target sequence to bind to a test sequence, or vice-versa.

"Hybridization conditions" are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (50° below the Tm of the probe); "high stringency" at about 5–10° below the Tm; "intermediate stringency" at about 10–20° below the Tm of the probe; and "low stringency" at about 20–25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, one will typically desire to employ relatively stringent conditions to form the hybrids, e.g., one will select relatively low salt and/or high temperature conditions. Hybridization conditions, including moderate stringency and high stringency, are provided in Sambrook et al., incorporated herein by reference.

The term "isolated" or "purified" means that a material is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. A nucleic acid or protein is said to be purified, for example, if it gives rise to essentially one band in an electrophoretic gel.

As used herein in referring to phytate hydrolyzing enzymes (phytases), the term "derived from" is intended not only to indicate a phytase produced or producible by a strain of the organism in question, but also a phytase encoded by a DNA sequence isolated from such strain and produced in a host organism containing such DNA sequence. Additionally, the term is intended to indicate a phytase which is encoded by a DNA sequence of synthetic and/or cDNA origin and which has the identifying characteristics of the phytase in question. To exemplify, "phytases derived from Penicillium" refers to those enzymes having phytase activity which are naturally-produced by Penicillium, as well as to phytases like those produced by Penicillium sources but which through the use of genetic engineering techniques are produced by non-Penicillium organisms transformed with a nucleic acid encoding said phytases.

The present invention encompasses phytate hydrolyzing enzymes that are equivalent to those that are derived from the particular microbial strain mentioned. Being "equivalent," in this context, means that the phytate hydrolyzing enzymes are encoded by a polynucleotide capable of hybridizing to the polynucleotide having the sequence as shown in any one of FIGS. 1A–1C under conditions of medium to high stringency. Being equivalent means that the phytate hydrolyzing enzyme comprises at least 55%, at least 65%, at least 70%, at least 75%, at least 80%, at least 85%, at least 90%, or at least 95% identity to the phytate hydrolyzing enzyme having the amino acid sequence disclosed in FIG. 2 (SEQ ID NO:4).

The present invention also encompasses mutants, variants and derivatives of the phytate hydrolyzing enzymes of the present invention as long as the mutant, variant or derivative phytate hydrolyzing enzyme is able to retain at least one characteristic activity of the naturally occurring phytate hydrolyzing enzyme.

As used herein, the term "mutants and variants", when referring to phytate hydrolyzing enzymes, refers to phytate hydrolyzing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phytate hydrolyzing enzyme.

The term "derivative" or "functional derivative" as it relates to phytase is used herein to indicate a derivative of phytase which has the functional characteristics of phytase of the present invention. Functional derivatives of phytase encompass naturally occurring, synthetically or recombinantly produced peptides or peptide fragments, mutants or variants which may have one or more amino acid deletions, substitutions or additions which have the general characteristics of the phytase of the present invention.

The term "functional derivative" as it relates to nucleic acids encoding phytase is used throughout the specification to indicate a derivative of a nucleic acid which has the functional characteristics of a nucleic acid which encodes phytase. Functional derivatives of a nucleic acid which encode phytase of the present invention encompass naturally occurring, synthetically or recombinantly produced nucleic acids or fragments, mutants or variants thereof which may have one or more nucleic acid deletions, substitutions or additions and encode phytase characteristic of the present invention. Variants of nucleic acid encoding phytase according to the invention include alleles and variants based on the degeneracy of the genetic code known in the art. Mutants of nucleic acid encoding phytase according to the invention include mutants produced via site-directed mutagenesis techniques (see for example, Botstein, D. and Shortle, D., 1985, Science 229:1193–1201 and Myers, R. M., Lerman, L. S., and Maniatis, T., 1985, Science 229: 242–247), error-prone PCR (see for example, Leung, D. W., Chen, E., and Goeddel, D. V., 1989, Technique 1: 11–15; Eckert, K. A. and Kunkel, T. A., 1991, PCR Methods Applic. 1: 17–24; and Cadwell, R. C. and Joyce, G. F., 1992, PCR Methods Applic. 2: 28–33) and/or chemical-induced mutagenesis techniques known in the art (see for example, Elander, R. P., Microbial screening, Selection and Strain Improvement, in Basic Biotechnology, J. Bullock and B. Kristiansen Eds., Academic Press, New York, 1987, 217).

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control such transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter and a preferred promoter used in *Aspergillus niger* is glaA. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2 μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook et al., Molecular Cloning: A Laboratory Manual, Second Edition, Cold Spring Harbor Press (1989). Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70–76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. For example, host strains can be *Bacillus subtilis, Escherichia coli, Trichoderma longibrachiatum, Saccharomyces cerevisiae, Aspergillus niger*, and *Aspergillus nidulans*. Host cells are transformed or transfected with vectors constructed using recombinant DNA techniques. Such transformed host cells are capable of both replicating vectors encoding phytase and its variants (mutants) or expressing the desired peptide product.

Examples of appropriate expression hosts include: bacterial cells, such as *E. coli*, Streptomyces, *Salmonella typhimurium*; fungal cells, such as Aspergillus and Penicillium; insect cells such as Drosophila and Spodoptera Sf9; animal cells such as CHO, COS, HEK 293 or Bowes melanoma; plant cells, etc. The selection of an appropriate host is deemed to be within the scope of those skilled in the art from the teachings herein. It should be noted that the invention is not limited by the particular host cells employed.

II. Phytase Enzymes and Nucleic Acid Encoding Phytase Enzymes

One aspect of the present invention provides proteins or polypeptides which are capable of catalysing the hydrolysis of phytate and releasing inorganic phosphate; for example, enzymes having catalytic activity as defined in Enzyme Commission EC number 3.1.3.8, or in EC number 3.1.3.26. In one preferred embodiment, the invention provides a so-called 3-phytase. The present invention additionally encompasses polynucleotides (e.g., DNA) which encode such phytate hydrolyzing proteins or polypeptides.

Preferably, the phytase and/or polynucleotides encoding the phytase according to the present invention is derived from a fungus, more preferably from an anaerobic fungus and most preferably from Penicillium spp., e.g., *Penicillium hordei* or *Penicillium piceum*. Thus, it is contemplated that the phytase or the DNA encoding the phytase according to the invention can be derived from Absidia spp.; Acremonium spp.; Actinomycetes spp.; Agaricus spp.; Anaeromyces spp.; Aspergillus spp., including *A. auculeatus, A. awamori, A. flavus, A. foetidus, A. fumaricus, A. fumigatus, A. nidulans, A. niger, A. oryzae, A. terreus* and *A. versicolor*; Aeurobasidium spp.; Cephalosporum spp.; Chaetomium spp.; Coprinus spp.; Dactyllum spp.; Fusarium spp., including *F. conglomerans, F. decemcellulare, F. javanicum, F. lini, F. oxysporum* and *F. solani*; Gliocladium spp.; Humicola spp., including *H. insolens* and *H. lanuginosa*; Mucor spp.; Neurospora spp., including *N. crassa* and *N. sitophila*; Neocallimastix spp.; Orpinomyces spp.; Penicillium spp; Phanerochaete spp.; Phiebia spp.; Piromyces spp.; Pseudomonas spp.; Rhizopus spp.; Schizophyllum spp.; Streptomyces spp; Trametes spp.; and Trichoderma spp., including *T. reesei, T. iongibrachiatum* and *T. viride*; and Zygorhynchus spp. Similarly, it is envisioned that a phytase and/or DNA encoding a phytase as described herein may be derived from bacteria such as Streptomyces spp., including *S. olivochromogenes*; specifically fiber degrading ruminal bacteria such as *Fibrobacter succinogenes*; and in yeast including *Candida torresii; C. parapsilosis; C. sake; C. zeylanoides; Pichia minuta; Rhodotorula glutinis; R. mucilaginosa*; and *Sporobolomyces holsaticus*.

In one preferred embodiment, the phytase and/or polynucleotides encoding the phytase according to the present invention is/are derived from (i) a grain-spoilage fungus, such as *Penicillium hordei, Penicillium piceum*, or *Penicillium brevi-compactum*; or (ii) an ectomycorrhizal fungus associated with tree roots, e.g., *Laccaria laccata, Laccaria rufus, Paxillus involutus, Hebeloma crustuliniforme, Amanita rubescens*, or *Amanita muscaria*.

According to a preferred embodiment, the phytase and/or polynucleotide encoding the phytase of the present invention is in a purified form, i.e., present in a particular composition in a higher or lower concentration than exists in a naturally occurring or wild type organism or in combination with components not normally present upon expression from a naturally occurring or wild type organism.

The invention encompasses phytate hydrolyzing proteins and peptides comprising at least 65%, at least 70%, at least 75%, at least 80%, at least 85%, at least 90% or at least 95% identity to the phytate hydrolyzing enzyme having the amino acid sequence disclosed in FIG. 2 (SEQ ID NO:4).

The inventon further encompasses polynucleotides, e.g., DNA, which encode phytate hydrolyzing enzymes derived from fungal sources, such as Penicillium spp., which polynucleotides include a sequence having at least 65% identity, at least 70% identity, at least 75% identity, at least 80% identity, at least 85% identity, at least 90% identity and at least 95% identity to the polynucleotide sequence disclosed in any one of FIGS. 1A–1C (SEQ ID NO:1–3), as long as the enzyme encoded by the polynucleotide is capable of catalysing the hydrolysis of phytate and releasing inorganic phosphate. In a preferred embodiment, the polynucleotide encoding the phytate hydrolyzing enzyme has the polynucleotide sequence as shown in any one of FIGS. 1A–1C (SEQ ID NO:1–3), or is capable of hybridizing to the polynucleotide sequence as shown in any one of FIGS. 1A–1C (SEQ ID NO:1–3), or is complementary thereto. As will be understood by the skilled artisan, due to the degeneracy of the genetic code, a variety of polynucleotides can encode the phytate hydrolyzing enzyme disclosed in FIG. 2 (SEQ ID NO:4). The present invention encompasses all such polynucleotides.

III. Obtaining Polynucleotides Encoding a Phytate Hydrolyzing Enzyme

The nucleic acid encoding a phytate hydrolyzing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a fungal species (See, for example, Sambrook et al., 1989, Molecular Cloning, A Laboratory Manual, 2d Ed., Cold Spring Harbor Laboratory Press, Cold Spring Harbor, N.Y.; Glover, D M and Hames, B D (Eds.), DNA Cloning: A Practical Approach, Vols 1 and 2, Second Edition). Nucleic acid sequences derived from genomic DNA may contain regulatory regions in addition to coding regions.

In the molecular cloning of the gene from genomic DNA, DNA fragments are generated, some of which will comprise at least a portion of the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, PCR and column chromatography.

Once nucleic acid fragments are generated, identification of the specific DNA fragment encoding a phytate hydrolyzing enzyme may be accomplished in a number of ways. For example, a phytate hydrolyzing enzyme encoding gene of the present invention or its specific RNA, or a fragment thereof, such as a probe or primer, may be isolated and labeled and then used in hybridization assays to detect a generated gene. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under medium to high stringency.

The present invention encompasses phytate hydrolyzing enzymes derived from fungal species (esp., Penicillium species) which are identified through nucleic acid hybridization techniques using SEQ ID NO:1, SEQ ID NO:2, or SEQ ID NO:3, or a suitable portion or fragment thereof (e.g., at least about 10–15 contiguous nucleotides), as a probe or primer and screening nucleic acid of either genomic of cDNA origin. Nucleic acid encoding phytate hydrolyzing enzymes derived from Penicillium species and having at least 65% identity to SEQ ID NO:1, SEQ ID NO:2, or SEQ ID NO:3 or a portion or fragment thereof can be detected by DNA-DNA or DNA-RNA hybridization or amplification using probes, portions or fragments of SEQ ID NO:1, SEQ ID NO:2, or SEQ ID NO:3. Accordingly, the present invention provides a method for the detection of nucleic acid encoding a phytate hydrolyzing enzyme encompassed by the present invention which comprises hybridizing part or all of a nucleic acid sequence of SEQ ID NO:1, SEQ ID NO:2, or SEQ ID NO:3 with Penicillium nucleic acid of either genomic or cDNA origin.

Also included within the scope of the present invention are polynucleotide sequences that are capable of hybridizing to the nucleotide sequence disclosed in SEQ ID NO:1, SEQ ID NO:2, or SEQ ID NO:3 under conditions of medium to high stringency. In one embodiment, hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.) incorporated herein by reference, and confer a defined stringency. In this embodiment, "maximum stringency" typically occurs at about Tm-5° C. (5° C. below the Tm of the probe); "high stringency" at about 5° C. to 10° C. below Tm; "medium" or "intermediate stringency" at about 10° C. to 20° C. below Tm; and "low stringency" at about 20° C. to 25° C. below Tm. A maximum stringency hybridization can be used to identify or detect identical or near-identical polynucleotide sequences, while an intermediate or low stringency hybridization can be used to identify or detect polynucleotide sequence homologs.

In another embodiment, the stringency is determined by the washing conditions employed after hybridization. "Low-stringency" conditions, for purposes of this embodiment, comprise washing with a solution of 0.2×SSC/0.1% SDS at 20° C. for 15 minutes. "Standard-stringency" conditions comprise a further washing step comprising washing with a solution of 0.2×SSC/0.1% SDS at 37° C. for 30 minutes.

The process of amplification as carried out in polymerase chain reaction (PCR) technologies is described in Dieffenbach C W and G S Dveksler (1995, PCR Primer, a Laboratory Manual, Cold Spring Harbor Press, Plainview N.Y.). A nucleic acid sequence of at least about 10 nucleotides and as many as about 60 nucleotides from SEQ ID NO:1, SEQ ID NO:2, or SEQ ID NO:3, preferably about 12 to 30 nucleotides, and more preferably about 25 nucleotides can be used as a probe or PCR primer.

A preferred method of isolating a nucleic acid construct of the invention from a cDNA or genomic library is by use of polymerase chain reaction (PCR) using degenerate oligonucleotide probes prepared on the basis of the amino acid sequence of the protein having the amino acid sequence as shown in SEQ ID NO:4. For instance, the PCR may be carried out using the techniques described in U.S. Pat. No. 4,683,202.

In view of the above, it will be appreciated that the polynucleotide sequences provided in FIGS. 1A–1C (SEQ ID NO:1–3) are useful for obtaining identical or homologous fragments of polynucleotides from other species, and particularly from fungi (e.g., the grain-spoilage fungi, or the Ectomycorrhizae) which encode enzymes having phytase activity.

IV. Expression and Recovery of Phytate Hydrolyzing Enzymes

The polynucleotide sequences of the present invention may be expressed by operatively linking them to an expression control sequence in an appropriate expression vector and employed in that expression vector to transform an appropriate host according to techniques well established in the art. The polypeptides produced on expression of the DNA sequences of this invention can be isolated from the fermentation of cell cultures and purified in a variety of ways according to well established techniques in the art. One of skill in the art is capable of selecting the most appropriate isolation and purification techniques.

More particularly, the present invention provides host cells, expression methods and systems for the production of phytate hydrolyzing enzymes derived from microorganisms, such as Penicillium species. Once nucleic acid encoding a phytate hydrolyzing enzyme of the present invention is obtained, recombinant host cells containing the nucleic acid may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989).

In one embodiment, nucleic acid encoding phytate hydrolyzing enzymes derived from Penicillium species and having at least 65%, at least 70%, at least 75%, at least 80%, at least 85%, at least 90% and at least 95% identity to the nucleic acid of any one of FIGS. 1A–1C (SEQ ID NO:1–3) or a functional derivative thereof, or which is capable of hybridizing under conditions of intermediate to high stringency to the nucleic acid of any one of FIGS. 1A–1C (SEQ ID NO:1–3), or which is complementary to the nucleic acid of any one of FIGS. 1A–1C (SEQ ID NO:1–3) is obtained and transformed into a host cell using appropriate vectors.

The nucleic acid encoding phytate hydrolyzing enzymes can include a leader sequence capable of providing for the secretion of the encoded phytase. Depending on whether the phytase is to be expressed intracellularly or is secreted, a DNA sequence or expression vector of the invention can be engineered such that the mature form of the phytase is expressed with or without a natural phytase signal sequence or a signal sequence which functions in a fungus (e.g., *Aspergillus niger*), other prokaryotes or eukaryotes. Expression can also be achieved by either removing or partially removing said signal sequence.

A variety of vectors and transformation and expression cassettes suitable for the cloning, transformation and expression in fungus, yeast, bacteria, insect and plant cells are known by those of skill in the art. Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phytate hydrolyzing enzymes in a host cell are known to those skilled in the art. Nucleic acid encoding the phytate hydrolyzing enzyme is linked operably through initiation codons to selected expression control regions for effective expression of such enzyme. Once suitable cassettes are constructed, they are used to transform the host cell.

In cases where plant expression vectors are used, the expression of a sequence encoding phytase may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E (1992) in McGraw Hill Yearbook of Science and Technology, McGraw Hill, New York, N.Y., pp 191–196; orWeissbach and Weissbach (1988) Methods for Plant Molecular Biology, Academic Press, New York, N.Y., pp 421–463.

General transformation procedures are taught in Current Protocols In Molecular Biology (vol. 1, edited by Ausubel et al., John Wiley & Sons, Inc. 1987, Chapter 9) and include calcium phosphate methods, transformation using PEG and electroporation. For Aspergillus and Trichoderma, PEG and Calcium mediated protoplast transformation can be used (Finkelstein, D B 1992 Transformation. In Biotechnology of Filamentous Fungi. Technology and Products (eds by Finkelstein & Bill) 113–156. Electroporation of protoplast is disclosed in Finkelestein, D B 1992 Transformation. In Biotechnology of Filamentous Fungi. Technology and Products (eds by Finkelstein & Bill) 113–156. Microprojection bombardment on conidia is described in Fungaro et al. (1995) Transformation of *Aspergillus nidulans* by microprojection bombardment on intact conidia, FEMS Microbiology Letters 125 293–298. Agrobacterium mediated transformation is disclosed in Groot et al. (1998) *Agrobacterium tumefaciens*-mediated transformation of filamentous fungi, Nature Biotechnology 16 839–842. For transformation of Saccharomyces, lithium acetate mediated transformation and PEG and calcium mediated protoplast transformation as well as electroporation techniques are known by those of skill in the art.

Host cells which contain the coding sequence for a phytate hydrolyzing enzyme of the present invention and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

It should also be noted that the invention contemplates in vitro expression of the phytase enzymes described herein.

In one embodiment of the present invention, a polynucleotide sequence encoding a phytate hydrolyzing enzyme derived from *Penicillium hordei* (ATCC No. 22053) is isolated and expressed in *Aspergillus niger*, and in another embodiment is expressed in *Aspergillus nidulans*. The expressed phytase can then be recovered, e.g., as described next.

The phytase of the invention can be recovered from culture medium or from host cell lysates. If membrane-bound, it can be released from the membrane using a suitable detergent solution (e.g. Triton-X 100) or by enzymatic cleavage. Cells employed in expression of phytase can be disrupted by various physical or chemical means, such as freeze-thaw cycling, sonication, mechanical disruption, or cell lysing agents. It may be desired to purify the phytase from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants; and metal chelating columns to bind epitope-tagged forms of the phytase. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular form of phytase produced.

V. Applications of Phytate Hydrolyzing Enzymes

The phytase and derivatives thereof as taught herein can be used in a variety of applications where it is desirable to separate phosphorous from phytate. Several exemplary applications are set forth below.

For example, the invention provides for the use of bacterial cells or spores capable of producing phytase according to the invention as a probiotic or direct fed microbial product. Preferred embodiments for said uses are phytase-producing Aspergillus sp. of the invention.

In addition, the invention contemplates the use of phytase as described herein in food or animal feed.

The present invention provides food or animal feed including phytase as described herein. Preferably, said food or animal feed comprises phytase as an additive which is active in the digestive tract, preferably the crop and/or small intestine, of livestock, such as poultry and swine, and aquatic farm animals including fish and shrimp. Said additive is also preferably active in food or feed processing.

The invention additionally provides food or animal feed comprising cells or spores capable of expressing phytase as described herein.

Still further, the present invention contemplates a method for the production of a food or animal feed, characterised in that phytase according to the invention is mixed with said food or animal feed. Said phytase is added as a dry product before processing or as a liquid before or after processing. According to one embodiment, wherein a dry powder is used, the enzyme is diluted as a liquid onto a dry carrier such as milled grain.

The present invention also provides a method for the production of a food or animal feed, characterised in that cells and/or spores capable of expressing phytase according to the inveniton are added to said food or animal feed.

Further, the present invention provides for the use of the phytase described herein with or without accessory phosphatases in the production of inositol and inorganic phosphate, and phytate intermediates.

Also provided is a method for the reduction of levels of phosphorous in animal manure, characterised in that an animal is fed an animal feed according to the invention in an amount effective in converting phytate contained in said animal feed.

The phytase and phytate-derived intermediates of the invention can also be used in grain wet milling, in cleaning and personal care products, and in textile processing.

The following examples are offered for illustrative purposes only, and are not intended to limit the scope of the present invention in any way. All patent and literature references cited in the present specification are hereby incorporated by reference in their entirety.

EXAMPLES

Example 1

Evidence of Phytate Hydrolysing Activity in Liquid Culture

*P. piceum* (ATCC No. 10519) and *P. hordei* (ATCC No. 22053) were grown in defined media containing various concentrations of inorganic phosphate, and growth characteristics and phytase production were assayed and compared. Spore suspensions were used ($2\times10^6$ spores/ml final con) to inoculate a minimal media (Vogels) where the phosphate concentration was altered to see how this would affect growth and phytase production. Cultures were grown in 50 ml of medium in shake flask culture at 25° C. (*P.hordei*) or 30° C. (*P.piceum*). Cultures were harvested at 24, 48, 72 and 96 hours. Cultures supernatants were assayed for phytase activity using the method of Fiske and SubbaRow. Growth was determined by dry weight (*P.hordei*) or OD readings (*P.piceum*).

1A. Effect of Different Media Conditions on Growth and Morphology

The series of Penicillium growth curves that were produced, such as the *P. piceum* growth curve of FIG. 3 and the *P. hordei* growth curve of FIG. 4, looked at the effect of available P in the medium on growth and phytase production. With particular regard to *P. piceum*, when the P level was reduced to 0.57 mM (1/64 P from growth curve [FIG. 3]), morphological changes in the growth of the fungus were observed which are associated with a stressed condition (e.g., mycelial fragmentation, pelleting, heterogeneous growth and an overall appearance of a pale yellow color). This physiological strain was related to the appearance of phytase activity at a point in the growth curve approaching late exponential phase (48 hours; See Table 1, below). Morphological evidence of phytic acid utilisation was observed in identical cultures of low P (0.57 mM) supplemented after 24 hours growth with 1 mM phytate as a phosphorus source. The morphological changes seen without added phytate were not apparent, indeed the supplemented samples resembled cultures in media of higher P which were not limiting. This clearly indicates that a phytic acid specific hydrolysing activity was being produced so that P could be supplied to the growing fungus. However, when 5 mM phytate was supplemented the cultures did not grow, suggesting that this level of phytate in the medium chelates essential minerals resulting in a medium that cannot support fungal growth and nutrition.

In an exemplary *P.hordei* study, the fungus was grown in media containing

High phosphate (1.14 mM)

Low phosphate (0.57 mM)

Low phosphate plus 1 mM supplemented phytate.

Growth was monitored over 0, 24, 48, 72 and 96 hours by dry weight measurements, and the morphological characteristics in response to the different media conditions was also observed. The major observations and conclusions are as follows:

1. Expected good growth in high phosphate, consistent fungal morphology indicative of healthy culture.
2. Growth was markedly poorer in low phosphate condition, fungal morphology was heterogenous with evidence of clumping and mycelial fragmentation. Culture had a sickly yellow appearance.

3. Similar cultures as for (2) when supplemented with phytate (the substrate) no longer looked under the same physiological stress. Biomass growth was similar to condition (1) and the fungal morphology was the same as for the high phosphate condition.
4. Growth curves and photographic evidence of these cultures back these observations up, and the overall major conclusion is that we are seeing a phytate hydrolysing activity in condition (3) which allows the fungus to access phosphate from phytate, and so circumvent the phosphate starvation stresses that the culture is otherwise experiencing.

1B. Phytase Activity in Culture Supernatants

Table 1, below, shows phytase activity in the culture supernatants of *P. piceum*. Also shown in Table 1, is data for cultures of *A.niger*, grown under the same conditions in the Vogels 1/64 P (0.57 mM) medium as a control for phytase activity. As can be seen, the *A. niger* cultures showed similar levels to the *P. piceum* cultures.

TABLE 1

Phytase activity in culture supernatants of fungi growing on media with variable levels of inorganic P.

| Fungal species | Medium type | P content (mM) | Phytase activity ($\mu$molesPmin$^{-1}$ml$^{-1}$) |
|---|---|---|---|
| *P. piceum* | 1/2 × MEB | 8–12 | 0± |
| *P. piceum* | Vogels (full P) | 37.0 | 0± |
| *P. piceum* | Vogels (1/4 P) | 9.20 | 0± |
| *P. piceum** | Vogels (1/64 P) | 0.57 | 0.121 ± 0.077 |
| *P. piceum*** | Vogels (1/64 P) | 0.57 | 0.0281 ± 0.027 |
| *A. niger* | Vogels (1/64 P) | 0.57 | 0.036 ± 0.027 |

These samples compare activites that were detected at 48 hours post inoculation. Phytase activity is expressed as the number of $\mu$moles P released per minute per ml culture supernatant. Sample activities are calculated from triplicate culture flasks where supernatants were assayed for phytase in duplicate. Activities are shown as mean ± SD, n = 6. *P. piceum** and *P. piceum*** refer to data from two separate time course experiments.

Thus, a clear physiological stress was associated with cultures where phosphate was limited, which adversely affected growth, and was linked to the appearance of phytase activity.

1C. Concentration of Culture Supernatants

Additional evidence of phytase activity can be expected from concentrated supernatant (concentrated protein). For example, concentrated protein samples can be obtained from:

1. Cultures of Penicillium from conditions of stress and low phosphate (where phytase is expected to be expressed),
2. Cultures of Penicillium of high phosphate and no stress, where phytase is not expected to be produced, and
3. Cultures supplemented with low phosphate and supplemental phytate.

Silverstained SDS-PAGE gels of these concentrated protein samples are expected to show a protein profile demonstrating the appearance of a protein band (putative phytase band) in concentrated protein from condition 1 (above) which is not present in condition 2. A similar appearance of this band is also expected in condition 3, albeit at a lower level. Based on the amino acid sequence of the *P.hordei* phytase, and on the fact that it appears to be an extracelleular enzyme, the expected size of the protein is 50 kDa approximately. It should be noted, however, that glycosylation modification on the extracellular enzyme may increase the MW to 60–90 kDa.

Example 2

PCR Amplification of Phytase Gene Fragments

2A. Degenerate Primer Design

Based on alignments of published phytase amino acid sequences, a range of degenerate primers were designed against conserved structural and catalytic regions. Such regions included those that were highly conserved among the phytases, as well as those known to be important for enzyme structure and function.

In one study, amino acid sequences for 4 published phytases were aligned. The sequences were of phytases from: (i) *A.niger* (DEFINITION: *A.niger* phyA gene.; ACCESSION: Z16414; van Hartingsveldt, W., et al, 1992); (ii) *A.fumigatus* (DEFINITION: Aspergillus fumigatus phytase gene, complete cds.; ACCESSION: U59804; Pasamontes, L., et al, 1997); (iii) *A.terreus* (DEFINITION: Aspergillus terreus 9A1 phytase gene, complete cds.; ACCESSION: U59805; Mitchell, D. B., et al, 1997); and (iv) *Myceliophtora thermophilus* (DEFINITION: *Myceliophthora thermophila* phytase gene, complete cds.; ACCESSION: U59806; Mitchell, D. B., et al, 1997). It should be noted that all of these sequences are publicly available from GENbank, and each is incorporated herein by reference.

Five particular regions were chosen to meet the criteria above, and a range of forward and reverse primers designed from the amino acid sequences. The specific amino acid regions used to design the primers are highlighted in black border in the protein sequence alignment of FIG. 5. Using the genetic code for codon usage, degenerate nucleotide PCR primers were synthesised by MWG-Biotech Ltd.

In another study, a pair of primers denoted as CS1 (SEQ ID NO:25) and CS2 (SEQ ID NO:26) were designed from the published amino acid sequence for phyA and phyB phytases from *A.niger* alone. These primers were designed as follows:

Primer CS1: Forward (5'–3') primer from the region RHGARYPT (See FIG. 5, a.a. 110–120 approx) which is the phosphate binding domain of a phyA phytase and essential for catalytic activity.

Primer CS2: Reverse primer from the region FT(H/Q) DEW(I/V) (See FIG. 5, a.a. 335–345 approx) which was a central phytase region which seemed to be conserved relatively well.

The primer sequences are as follows:

CS1:5' CGI CAT/C GGI GCI CGI TAT/C CC 3' (SEQ ID NO:25)

CS2:3' AAA/G TGI GTI CTA/G CTT/C ACC T/CAI 5'

CS2:5' AC/TC CAC/T TCG/A TCI TGI GTG/A AA 3' (SEQ ID NO:26)

As all primers were synthesised in the 5'–3' direction, the reverse primer was made as outlined in bold for CS2. The standard genetic code was used to change from amino acid to triplet codon, and standard IUB code for mixed base sites was used (e.g. to designate I for A/C/T/G).

Additional details concerning the design of primers CS1 and CS2 will now be described with reference to FIG. 6. FIG. 6 shows the published amino acid sequence for phyA and phyB phytases from *A.niger* (SEQ ID NO:11–14) from which primers CS1 and CS2 were designed. Particularly, the sequences aligned are from 1; Piddington et al, 1993 (Phy a and Phy b from *A. niger* var. awamori), 2; van Hartingsveldt et al., 1993 (Phy a from *A. niger*), 3: Erlich et al., 1993 (Phy B from *A. niger*). The alignment of FIG. 1 was performed using CLUSTAL V (Higgins D. G., et al, 1992) from the PHYLIP version 3.5 package. Conserved sequences used to design degenerate primers CS1, CS2 are shown.

As can be seen from the alignment of FIG. 6, the phosphate-binding domain of PhyA and PhyB is well conserved with only a single amino acid difference between PhyA (RHGARYP; van Hartingsveldt et al., 1993) and PhyB (RHGERYP; Piddington et al., 1993). Degenerate primer CS1 was designed complementary to this region in the phyA version of the sequence only, i.e. using RHGARYPT as the basis for primer design. This was so to bias the primer towards a phyA type phosphate binding domain in this instance. The second conserved region, which served as the base is for primer CS2, occurs in the middle of the PhyA and PhyB amino acid sequence. This conserved central phytase-specific domain in PhyA (FTHDEWI) corresponds to amino acids 285–291. In PhyB, the amino acid sequence (FTQDEWV) corresponds to amino acids 280–286.

Degenerate primers CS1 and CS2 successfully amplified a 650 bp region from *P.hordei* by PCR, as described next.

2B. PCR Amplification of Phytase Gene Fragments

Penicillium species genomic DNA was used as a template for PCR amplification of putative phytase gene fragments using combinations of the above-described primers. PCR was carried out using the PCR Ready-to-go Beads from Amersham Pharmacia. Conditions were determined by individual experiments, but typically thirty cycles were run in a Techne thermal cycler. Successful amplification was verified by electrophoresis of the PCR reaction on a 1% agarose gel. A PCR product that was amplified from *P.hordei* by the primers CS1 and CS2 and was of the correct expected size (650 bp) was purified by gel extraction using the Qiaquick Spin Gel Extraction kit from Qiagen. The purified PCR product was ligated into the commercial pGEM-T Easy vector System (Promega Corporation) to facilitate cloning. Ligation reactions were incubated at 4° C. overnight in a total volume of 10 $\mu$l containing 0.1 volumes of 10×ligase buffer and 1 $\mu$l (1 U.$\mu l^{-1}$) of T4 DNA ligase. Typically insert DNA was used in the reaction in a 1–4:1 molar ratio of insert to vector DNA. A 100 $\mu$l aliquot of $CaCl_2$ competent *E. coli* XL-1 Blue cells were removed from −80° C. storage and thawed on ice for transformation. 3 $\mu$l of ligation mix was added to the cells and the mixture incubated on ice for 20 min. The cells were then heat shocked at 42° C. for 1 min. and returned to ice for 5 min. The transformation mixture was added to 0.9 mL of L-broth, and the cells incubated with shaking and without selection to allow expression of the ampicillin resistance gene product before selection is applied (37° C., 1 h). Aliquots of 200, 300 and 400 $\mu$l of this culture were then spread directly on selective agar plates. Plates were incubated at 37° C. overnight. Colonies containing recombinant plasmids were visualised using blue/white selection. For rapid screening of recombinant transformants, plasmid DNA was prepared from cultures of putative positive (white) colonies. DNA was isolated by the method of Birnboim and Doly following the protocol in Sambrook et al (1989). The presence of the correct insert (650 bp) in the recombinant plasmid was confirmed by restriction analysis. DNA was digested with Not1-pPst1 restriction enzymes overnight at 37° C., and digest products visualized by agarose gel electrophoresis. A number of clones contained the correct sized insert and were selected for manual sequencing to see if the insert was a phytase gene fragment. Inserts were sequenced using the dideoxy chain termination method of Sanger et al (1977) with a modified form of T7 DNA polymerase (Sequenase version 2.0). The reactions were carried out using reagents supplied in the Sequenase version 2.0 kit (Amersham Life Science-United States Biochemical Corporation), following the manufacturer's protocol. Partial sequence from the ends of two clones (designated 3D and 3G) indicated that a phytase gene fragment had been cloned. Plasmid DNA from both of these clones were sent off to MWG-Biotech Ltd. for full sequencing of the double-stranded inserts.

2C. Sequence Analysis

The sequences were analysed by BLAST and protein translation sequence tools. BLAST comparison at the nucleotide level showed various levels of homology to published phyA phytase sequences. Initially, nucleotide sequences were submitted to BLAST (Basic BLAST version 2.0) by accessing the BLAST database on the world wide web. The web site used was at http://ncbi.nlm.nih.gov/cgi-bin/BLAST. The program chosen was blastn, and the database chosen was nr. Standard/default parameter values were employed. Sequence data for putative *P.hordei* gene fragments were entered as sequence in FASTA format and the query submitted to BLAST to compare the sequences of the present invention to those already in the database. The results returned for the 650 bp fragment and the EcoRI gene fragment from the first library screen, discussed below, showed a high number of hits for phytase genes from *A.niger, E.nidulans, A.fumigatus* and *T.thermophilus.*

The sequences were then subjected to a DNA-to-protein translation tool called Protein machine. This tool is also available on the web at http://medkem.gu.se/edu/translat.html. Another suitable translation tool is known as Translation Machine, available on the web at http://www2.ebi.ac.uk/translate/. The DNA sequences of putative phytase gene fragments from *P.hordei* were inserted into the analysis block, and the standard genetic code was used as the basis for the translation. Translations were carried out in all three frames and on forward and reverse strands. The translated amino acid sequence was delivered on the screen by the analysis tool as amino acid sequence in one letter code. When translated to amino acid sequence, the clones were shown to contain 212 amino acids (636 bp was actual size of gene fragment) with no stop codons. Analysis of the amino acid sequence showed that the fragment contained both correct ends (as used to design primers CS1 and CS2), contained the essential P binding motif (RHGARYP) and three cysteines which are also present in published phyA phytase sequences. It was concluded that the 636 bp fragment cloned was a phyA phytase gene fragment from *P.hordei.*

Sequence alignments and analysis of those alignments was carried out at the nucleotide and amino acid level using the ALIGN program (Alignment Editor Version 4/97; Dominick Hepperle, Fontanestr. 9c, D016775, Neuglobsow, Germany). In performing the analysis, subject sequences were pasted in, and the PHYLIP Interleaved format employed. The homology analysis was carried out using the "Analyse" section of the program, and specifically the option entitled "Distance Analysis." This calculates % homologies and the number of different sites between species, using a minimum of two amino acid sequences (i.e., two "species"). Minimal and maximal homologies are calculated as %. The basis for homology analysis is done as % identity, on the calculation of "number of identical amino acids (or bases) divided by the total number of amino acids (or bases) multiplied by 100" to give a percentage value. *P.hordei* amino acid sequences were placed into the ALIGN program along with published phytase sequences and a manual alignment at the amino acid level carried out. Exemplary results are shown in FIG. 7. In FIG. 7, the sequence denoted as "*P.hordei*3D" (SEQ ID NO:16) represents the deduced translation for the PCR product obtained using degenerate primers CS1 and CS2.

Example 3

Southern Analysis for Library Production

Genomic DNA from *P.hordei, P.piceum* and *A.niger* were digested with a range of restriction enzymes overnight at 37°

C. Successfully digested DNA was run out on a 1% agarose gel in preparation for transfer to the nylon membrane. After completion of electrophoresis, the agarose gel was soaked for 10 min. in 0.2M HCl to depurinate the DNA and then rinsed briefly in $ddH_2O$. The DNA was transferred to the Hybond™-N+ membrane (Amersham International PLC) by alkali capillary blotting. The blot was set up so that the nylon filter was sandwiched between the gel and a stack of absorbent paper towels. A wick of Whatman 3MM paper (Schleicher and Schuell, Dassel, Germany) was prepared on a glass plate over a reservoir of transfer buffer (0.4M NaOH). The gel was inverted on the wick, taking care to avoid the formation of air bubbles, and surrounded by strips of Nescofilm to prevent the blotting action of the paper towels from by-passing the gel at its edges. The gel was covered with an equal sized piece of Hybond™-N+ membrane which had been cut in the corner to match the gel and pre-wetted in 3×SSC. Next, 3–5 pieces of 3MM paper were placed on top of the filter and the blot completed by adding a 10 cm stack of blotting paper followed by a 0.5 kg weight. The blot was left for 8–24 h to transfer the DNA. The membrane was then washed briefly in 2×SSC at RT and baked in a vacuum oven at 80° C. to fix the DNA to the membrane. The 636 bp fragment from *P.hordei* was used to probe the Southern blot. It was firstly labelled with $^{32}p$ isotope by use of the High Prime DNA Labelling Kit (Boehringer Mannheim). Denatured fragment was added into a random primed labelling reaction which incorporates radio-labelled adenine. The Southern blot was prehybridised for 1 hour at 42° C. in 12 mL of Easy-Hyb buffer (Boehringer Mannheim) in a hybridisation tube. Radiolabelled probe was denatured and added to 5 mL of Easy-Hyb hybridisation buffer and left to hybridise overnight at 42° C. Following hybridisation, the blot was washed by incubation in 40 mL 3×SSC, 0.1% SDS for 15 min at 42° C. This low stringency wash was repeated with fresh wash solution. After stringency washing, the lot was rinsed in 3×SSC, sealed in clear plastic and exposed to x-ray film. This was left for 2 hours and the film developed.

As shown in FIG. 8, strong hybridising bands were observed for *P.hordei* digests. In particular, FIG. 8 illustrates a Southern blot gel showing hybridization between a probe comprising the PCR product obtained using degenerate primers CS1 and CS2 and various digests of fungal genomic DNA; with: Lane 1—Size marker; Lane 2—*Aspergillus niger*—EcoRI; Lane 3—*Penicillium piceum*—EcoRI; Lane 4—*Penicillium hordei*—EcoRI; Lane 5— *Penicillium hordei*—BamHl; Lane 6—*Penicillium hordei*—Sall; Lane 7—*Penicillium hordei*—Kpnl; and, Lane 8—*Penicillium hordei*—Sacl. These results indicate that the 636 bp fragment can be used as a probe for library screening.

Example 4

Isolation of a Polynucleotide Sequence from the Genome of *P. hordei* Encoding a Phytase 4A. *P.hordei* Genomic Library Generation and Screening Following the Southern hybridisation analysis, it was decided to make a partial enomic library of *P.hordei* in order to try and clone the full-length phytase gene. A size restricted plasmid library targeting the 4.4 Kb EcoRI fragment (as estimated from Southern analysis) was generated. EcoRI digested *P.hordei* genomic DNA was run out on a 1.25% agarose gel. The digested fragments at approximately 4.4 Kb were extracted from the gel, and purified by Glass-Max (Gibco-BRL, Scotland). Purified genomic fragments were used in a shotgun ligation reaction with EcoRI linearised pSK II Bluescript vector (Stratagene). The vector was firstly dephosphorylated before ligation, and the ligation reaction was carried out at 14° C. overnight. The library was produced by transformation of *E.coli* XL-10 Gold ultracompetent cells (Stratagene). 100 μl aliquots cells were removed from −80° C. storage and thawed on ice for transformation. 4 μL of β-mercaptoethanol was added to the cells on ice. 3 μl of ligation mix was added to the mixture and the mixture incubated on ice for 20 min. The cells were then heat shocked at 42° C. for 30 sec and returned to ice for 2 min. The transformation mixture was added to 0.9 mL of NZY-broth, and the cells incubated with shaking and without selection to allow expression of the ampicillin resistance gene. The transformed cells were plated out on blue/white selection LB-agar plates, and left to incubate overnight at 37° C. A total of 728 colonies were seen on the plates, 450 of which were white. The colonies were lifted onto nitrocellulose filters by the method of Maniatis (10% SDS—lysis, 3 min; 1.5M NaOH-denaturation, 5 min; 1.5M TricHCl—neutralisation, 5 min; 3×SSC—rinse, 5 min). The filters were then baked for 2 hours at 80° C. under vacuum to fix the DNA. The library was screened with $^{32}p$ radiolabelled 636 bp probe in the same manner as for Southern hybridisation. After hybridisation the filters were washed twice in 3×SSC, 0.1% SDS, 42° C., 15 min. The filters were then rinsed in 3×SSC, sealed in plastic and exposed to X-ray film overnight at −80° C. Five positive hybridising spots were seen on the film. These were aligned to the agar plates containing the transformants. The hybridising spots matched up to more than one single colony on the agar plates. All colonies in the radius of the hybridising spot were picked up using sterile loops and used to inoculate 2 mL of Luria broth. The cultures were grown at 37° C. for 2 hours. Dilutions of the cultures were made from $10^{-1}$ to $10^{-5}$ and 100 μL of each sample was plated out on LB-amp agar plates and incubated overnight at 37° C. The plates which had between 10 and 150 colonies on them were chosen to go forward for a secondary screen. Colony lifts were done as before, and filters were processed using the same procedures. Fresh $^{32}P$ labelled probe was prepared, and the filters screened in the same way as outlined previously. Stringency washes were carried out using 2×SSC, 0.1% SDS at 42° C. for 15 min. Filters were then rinsed in 2×SSC, sealed in plastic and exposed to X-ray film for 2 hours. The developed film showed a very high number of strong hybridising spots, consistent with amplification of the positive colonies from the primary screen. The film was then aligned to the plates, and the spots then coordinated to see if they corresponded to single isolated colonies. The best 12 positives that matched up to single colonies were picked and used to inoculate Luria broth for plasmid DNA preparations. Plasmid DNA was purified by Qiaspin Mini-Prep kit (Qiagen) and restriction analysis carried out to estimate the size of the inserts. All twelve clones gave the same restriction profile which suggested an insert size between 3–4 Kb. Six of the clones were sent away to MWG-Biotech Ltd. for partial sequencing to determine if they were the correct gene/gene fragment. Sequence analysis showed that three of the clones contained a gene fragment from a phyA phytase, but only at one end. These three clones were then sent off to get full sequencing done on the inserts.

Sequence analysis on the full sequence for these clones indicated that all three clones were the same thing, and that they encoded 355 amino acids corresponding to approx. 80% of the phyA phytase gene (see FIG. 7, line 1, denoted "*P hordei*"). It was apparent that there was an internal EcoRI site in the gene at a position approximately 300–400 bp downstream of the start of the gene.

4B. Percentage Identity Comparison Between Fungal Phytases

The deduced polypeptide product of the cloned phytase gene fragment was used for homology analysis with the published phytases. The analysis showed identities of from about 42–56% (See Table 2, below) and, together with analysis of the translated sequence, provided evidence that the gene fragment cloned was a phyA phytase.

TABLE 2

Percentage Identity Comparison Between Fungal Phytases (ALIGN editor)

| Species | *P. hordei* | *A. niger* | *A. fumigatus* | *A. terreus* | *M. thermo-philus* |
|---|---|---|---|---|---|
| *P. hordei* | | 55.6 | 56.2 | 52.5 | 42.4 |
| *A. niger* | | | 67.4 | 62.1 | 44.9 |
| *A. fumigatus* | | | | 61.7 | 47.6 |
| *A. terreus* | | | | | 43.7 |
| *M. thermo-philus* | | | | | |

Note: Comparison based upon approx. 80% of the deduced *P. hordei* phytase amino acid sequence (i.e., N-terminal portion [~140 a.a.] missing).

4C. Generation and Screening of SalI-based Size-restricted Genomic Library to Isolate Remainder of Phytase Gene In order to isolate the estimated remaining 20% of the *P. hordei* phytase gene, it was decided to use a second restriction enzyme to generate a second partial genomic library to isolate the 5' end of the gene, and attempt to then subclone the two fragments together. The restriction endonuclease recognition sites present within the cloned phytase sequence were identified using Webcutter. Of particular interest were sites for enzymes that were used in the Southern analysis illustrated in FIG. 8. It was found that these enzymes (KpnI, SacI, BamHI and SalI) all cut within the phytase sequence at 48 bp, 75 bp, 486 bp and 660 bp respectively from the 5' end of the cloned fragment. Southern analysis of digests of *P. hordei* genomic DNA (FIG. 8) shows that the BamHI fragment is very large (approximately 8 Kb), and would be difficult to clone in a plasmid-based library. The degree of hybridisation with the KpnI band is not strong enough for a library screen, and the presence of two bands on the SacI lane is likely to complicate the screening process. It was decided to generate a SalI-based size-restricted library in the same manner as before, to isolate the 1.8 Kb SalI band. With the presence of one known SalI site at a position approximately 120 bp downstream of the end of the probe sequence, it is likely that there is another SalI site at a position upstream of the start of the phytase gene. The library was made as before in pBluecript SKII, and screened using the same 636 bp probe. A selection of positive hybridising colonies were chosen and aligned to colonies on the plates. All 12 matched up to single isolated colonies, and were picked for plasmid DNA preparations. Restriction analysis showed that only three clones had inserts, all of which were approximately 1.8 Kb. These two clones (CS112, CS114) were then sent away to MWG-Biotech for full sequencing. Deduced amino acid sequence showed that the clones contained sequence that had motifs belonging to phyA phytase, but CS112 had a high number of sequencing errors. Analysis of clone CS114 showed there was a 450 bp overlap between the genomic fragments of the phytase gene. A proposed start codon was identified, as well as a 5' intron, and upstream regulatory elements were also identified on CS114.

4D. Amplification of Contiguous Phytase Gene for Heterologous Expression

A composite phytase sequence was produced from the two genomic clones CS114 and CS101 (FIG. 9), and used to design a number of upstream and downstream primers which could be used to amplify a contiguous phytase gene sequence. PCR amplification was also designed to facilitate cloning and expression of the complete phytase gene in to the heterologous expression vector pGAPT-PG, a 5.1 Kb construct provided by Genencor International, Inc. (See FIG. 11). There are two restriction enzyme sites (EcoRV and AgeI) within the multiple cloning site of pGAPT-PG which are not present within the phytase gene sequence. A number of 5' and 3' flanking primers were designed using the phytase gene sequence, and modified to include the restriction enzyme recognition sites for these enzymes (Table 3).

TABLE 3

Sequences of phytase-specific primers as designed from composite phyA gene sequence from clones CS101 and CS114

| Primer | Region | Sequence |
|---|---|---|
| CS201 (F) | 5' upstream flanking region including EcoRV site | 5' CGG C**GA TAT C**AG TAT CCC TGC GGT 3' (SEQ ID NO:23) |
| CS202 (F) | 5' upstream flanking region including EcoRV site | 5' CGG C**GA TAT C**CC GGT GAC GTC GGG T 3' (SEQ ID NO:20) |
| CS203 (R) | 3' downstream flanking region incuding AgeI site | 5' CGG C**AC CGG T**GG AAG AGG ACC AAC C 3' (SEQ ID NO:20) |
| CS204 (R) | 3' downstream flanking region including AgeI site | 5' CGG C**AC CGG T**GC ATT ATT ATT GGC C 3' (SEQ ID NO:23) |

F indicates a forward primer (5'→3') on the positive strand; R indicates a reverse primer on the negative strand. The restriction enzyme recognition sites that are designed into the primer sequences to facilitate cloning into the expression vector pGAPT-PG are underlined and highlighted in bold. The upstream and downstream flanking regions used to design the primers were arbitrarily chosen at approximately 100 bp upstream from the ATG (start) codon and downstream from the TAG (stop) codon respectively. The gene sequence used was also chosen to contain as equal balance of bases as possible.

Amplification of the phytase gene by PCR was attempted using genomic DNA from the *P. hordei*, and combinations of these primers. PCR should amplify a region of approximately 1.7 Kb, corresponding to the full-length phytase gene. FIG. 12 shows the results of PCR performed using primers CS201 or CS202 and CS203. A band of the correct size can be seen for the combination CS201–CS203, but the presence of multiple bands of lower molecular weight can also be seen. No amplification using CS202–CS203 can be seen for these conditions, although very faint bands at approximately 1.7 Kb could be seen at annealing temperature of 50° C. (not shown). A strong band was produced for CS201/CS202 and CS204 at approximately 700 bp (not shown). The desired product seen in FIG. 12 produced by amplification with the primers CS201–CS203, was cloned into the vector pTT and several clones which contained the correct size of insert were selected for sequencing (CS158 and CS167).

FIG. 10 illustrates the 5'/N-terminal nucleic acid sequence and 3'/C-terminal sequence (SEQ ID NO:20) of clone CS158 (SEQ ID NO:20). Preliminary deduced amino acid sequence for phytase is shown in bold (SEQ ID NO:19).

The sequence of clone CS167 was analysed and was not recognised as phytase. Analysis of clone CS158 revealed some interesting features. The deduced amino acid sequence for CS158 from the 3' end of the clone demonstrated high homology with CS101 phytase. However, the sequence generated from the 5' end differed substantially from CS114. This was particularly so for sequence that ran upstream from the phosphate binding domain motif (RHGARY). It was noticed that the sequence from CS158 at the 5' end was more similar to published phytase sequences, and contained a number of key structural motifs and conserved amino acids which were not present in the N-terminal CS114 amino acid sequence. It was concluded that clones CS101 and CS114 originated from 2 different genes, and that CS158 was the proper full-length phytase.

There were a number of sequencing errors apparent in the CS158 sequence. This is probably due to the fact the Taq polymerase was used in the amplification of the 1.7 Kb band shown in FIG. 12 Two new 5' primers were designed from the new sequence to re-amplify the phytase gene for expression. Two regions upstream of the putative start codons in the new phytase sequence from CS158 were selected, and modified to include EcoRV recognition sites to facilitate cloning into pGAPT-PG (Table 4).

TABLE 4

Sequences of phytase-specific primers as designed from the Taq polymerase amplified phyA gene sequence from clone CS158

| Primer | Region | Sequence |
|---|---|---|
| CS22 (F) | 5' upstream flanking region including EcoRV site | 5' GTT **GAT ATC** ACT TGT CGT GAT ACC C 3' (SEQ ID NO:31) |
| CS23 (F) | 5' upstream flanking region including EcoRV site | 5' TCT **GAT ATC** TCG ATA TCC TTG CAG G 3' (SEQ ID NO:32) |

F indicates a forward primer (5'→3') on the positive strand. The restriction enzyme recognition sites that are designed into the primer sequences to facilitate cloning into the expression vector PGAPT-PG are underlined and highlighted in bold. The upstream flanking regions used to design the primers were arbitrarily chosen at approximately 50–70 bp upstream from a proposed ATG (start). The gene sequence used was also chosen to contain as equal balance of bases as possible.

PCR amplification of *P. hordei* genomic DNA was carried out using a combination of these 5' primers and the 3' primers designed from CS101 (Table 3), and using a high fidelity DNA polymerase, Pfu, to minimise error for expression of the phytase gene (FIG. 13). This polymerase was Pfu DNA polymerase (Stratagene) and came as part of the Pfu DNA polymerase kit for PCR. For these reactions, reaction buffer, dNTPs, target DNA and primers were mixed together, and 2.5 units of Pfu polymerase added in a final reaction volume of 50 $\mu$L. After amplification, a 5 $\mu$L aliquot of the reaction mixture was analysed by gel electrophoresis. The primers designed from the new sequence in combination with primer CS204 produces a single intense product at the expected size (1.7 Kb). This fragment was cloned directly into the vector pCR-Blunt II TOPO (Invitrogen), and a select number of clones analysed to confirm the presence of the correct insert. (Blunt-ended PCR products that were generated by Pfu DNA polymerase were cloned into the Zero Blunt™ TOPO™PCR cloning kit (Invitrogen). This vector contains a MCS site and a kanamycin gene for anitbiotic resisistance, but also allows selectioon based on disruption of the lethal *E.coli* gene ccdb, as opposed to blue-white slection. Purified PCR product (50–200 ng) was added to 1 $\mu$L of pCR-BluntII-TOPO vector and the reaction volume made up to 5 $\mu$L with sterile water. This was mixed gently at left to incubate for 5 min at room temperature. 1 $\mu$L of 6×TOPO Cloning Stop Solution was added, and the reaction left on ice or frozen at −20° C. for up to 24 hours for transformation.) The integrity of the engineered EcoRV and AgeI sites was also confirmed by this analysis. A number of clones, CS212 and CS213 were prepared and sequenced. Sequence analysis confirmed the presence of a full-length phyA phytase gene. This gene was taken forward for expression in a heterologous system, and subsequent biochemical characterisation of the enzyme.

4E. Analysis of Sequence of *P. hordei* Phytase

CS213 represents the full-length phytase sequence from *P. hordei*. The genomic sequence for this clone can be seen in FIG. 1A (SEQ ID NO:1). The deduced amino acid sequence for the *P. hordei* phytase can be seen in FIG. 2 (SEQ ID NO:4).

An alignment was made of the *P. hordei* sequence and published phytases and homology analysis done, on a % identity basis. The results of this can be see in Table 4 below.

TABLE 4

% identity comparison between the phytases

| | *P. hordei* | AnigphyA | AfumphyA | AterrA-1 | *M. thermo* |
|---|---|---|---|---|---|
| *P. hordei* | — | 59.1 | 58.9 | 55.4 | 44.0 |
| *A. niger* | 212/518 | — | 68.3 | 63.7 | 46.3 |
| Afumigatus | 213/518 | 164/518 | — | 62.2 | 49.2 |
| Aterr9A-1 | 231/518 | 188/518 | 196/518 | — | 44.6 |
| *M. thermo* | 290/518 | 278/518 | 263/518 | 287/518 | |

The numbers in the left/bottom region indicate number of different sites between two species. Minimal Homology: 44.0% Maximal Homology: 68.3%

Example 5

Cloning, Expression and Characterisation of the Phytase from *P. hordei*

It was decided to attempt to over-express the phytase gene in a heterologous host to produce enough protein to carry out characetisation of the enzyme.

5A. Cloning of Phytase Gene into Expression Vector and Transformation in to *A. nidulans*

The full-length phytase gene that was amplified with a high-fidelity DNA polymerase, was produced using primers that were engineered to contain two restriction enzyme sites (EcoRV, AgeI). These sites were used to facilitate cloning into the expression vector pGAPT-PG (FIG. 11). The phytase clones CS212 and CS213 were digested with these enzymes and produced a single insert fragment of 1.7 Kb. pGAPT-PG was also digested with these enzymes and linearised. The phytase gene fragment was ligated to the expression vector, and a number of transformants produced. A selection of these clones was analysed to confirm the presence of the insert. The phytase clones were then used to transform swollen spores of A. nidulans by electroporation.

The transformation of *A. niger* strain FGSC A767 and *A. nidulans* FGSC A1032 by electroporation was adapted from the protocol of O. Sanchez and J. Aguirre developed for A. nidulans. 50 mL of YG medium (0.5% yeast extract, 2% glucose, supplemented with 10 mM uridine and 10 mM uracil) was inoculated at $10^7$ spores/mL with appropriate spore suspension. The cultures were grown for 4 hr at 25° C. at 300 rpm on rotary shaker. Swollen spores were collected by centrifugation at 400 rpm for 5 min at 4° C. Spores were resuspended in 200 mL ice-cold sterile water and centrifuged at 4000 rpm for 5 min at 4° C. The supernatant was poured off and the spores were resuspended in 12.5 ml YED media pH 8.0 (1% yeast extract, 1% glucose, 20 mM HEPES) and incubated for 60 min at 30° C. at 100 rpm on rotary shaker. The spores were collected by centrifugation at 400 rpm for 5 min, then resuspended in 1 mL of ice-cold EB buffer (10 mM tris-HCl, pH 7.5, 270 mM sucrose, 1 mM Lithium acetate) at a concentration of $10^9$ conidia.$mL^{-1}$ and kept on ice. 50 μL of the swollen spore suspension was mixed with 1 to 2 μg DNA in a total volume of 60 μL in sterile eppendorfs and kept on ice for 15 min. The suspension was transferred to 0.2 cm electroporation cuvette. Electroporation was carried out in a BioRad electroporation device (settings 1 kV, 400 W, 25 μF). 1 mL of ice-cold YED was added to the suspension after electroporation, and the combined mix was transfered to a pre-chilled sterile 15 mL Falcon tube and kept on ice for 15 min. This was then incubate at 30° C. for 90 min at 100 rpm on rotary shaker, with the tubes in a horizontal position. The spores were plated out and transformants were observed after 36–48 hours.

Circular plasmid DNA was used in each case, and 15 transformants were produced for the clones originating from CS213, while only 2 were produced from those originating from CS212. *A. niger* strain FGSC A767 and *A. nidulans* strain FGSC A1032 were obtained from the Fungal Genetics Stock Center, University of Kansas Medical Center, 3901 Rainbow Boulevard, Kansas City, Kans., USA.

5B. Preliminary Characterisation of *A. nidulans* Transformants

In total, 10 *A. nidulans* transformants were selected for further analysis (CS212-1, CS213-1 to 9). Spores from each of these transformants were used to inoculate selective media, and spore supensions of each clone were made. These were used to inoculate liquid cultures of the transformants which were screened for phytase activity. Cultures were grown over 72 hours, and the supernatants collected. Samples were desalted in PD-10 columns, and the protein samples eluted in 0.25 M sodium acetate. Phytase assays were carried out in the standard conditions (pH 5.5, 37° C. for 30 min). Two of the clones (CS213-2, CS213-4) demonstrated phytase activity in the culture supernatant. CS213-2 had a phytase activity recorded at 0.12 mmoles Pi released per mim per mL of culture supernatant, while transformant CS213-4 had an activity of 0.08 mmoles Pi released per min per mL. These were taken forward for further analysis.

5C. Time of Maximal Expression of Phytase in Liquid Culture

In order to assess when the level of phytase production was at its highest for subsequent biochemical characterisation, a series of liquid cultures of CS213-2 and CS213-4 were generated over a 2-day to 7-day period. Cultures were inoculated with spore suspension of the appropriate transformants, and harvested at each day over this period. Culture supernatants were processed as standard, and the desalted culture supernatant was assayed under standard phytase conditions. Table 5 summarises the results of these assays. Phytase activity is seen over the entire period, but expression is at its highest at the three day period.

TABLE 5

Phytase activity in culture supernatants of transformants over time

| Time point (days) | Activity of CS213-2 | Activity of CS213-4 |
|---|---|---|
| 2 | 35 | 36 |
| 3 | 76 | 75 |
| 4 | 36 | 33 |
| 5 | 35 | 35 |
| 6 | 34 | 33 |
| 7 | 33 | 32 |

Liquid cultures were harvested at each time point, desalted and eluted in 0.25 mM sodium acetate pH 5.5. Phytase assays were carried out under standard conditions (pH 5.5, 37° C., 30 min) in duplicate. Activity is expressed in phytase units per mL of culture supernatant (μmoles of Pi released min−1 mL−1).

Untransformed A. nidulans was also assayed across these time-points as a control. No phytase activity was detected. Protein samples from selected supernatant samples (day 4 and day 6), both before and after desalting were analysed by SDS-PAGE. Coomasie stained gels showed no bands for any samples used. This inferred that the total level of protein secreted into the medium was low. Silver stained gels also showed no evidence of any protein bands.

5D. Southern Analysis of Transformants

Although there was evidence that the *P. hordei* phytase gene had been successully cloned into the expression vector, pGAPT-PG, and that expression of an active enzyme had been achieved, molecular evidence was so far lacking. Genomic DNA preparations were made from the transformed A. nidulans CS213-2, and CS213-4, and from the original untransformed host. The DNA was digested with EcoRV, as there is no internal EcoRV site within the *P. hordei* phytase gene, and Southern hybridisation analysis of the transformants was carried out. The Southern blots were analysed with the 650 bp phytase probe from *P. hordei* (FIG. 14). Single strong hybridising bands can be seen for both of the transformants CS213-2 and CS213-4, under conditions of medium to high stringency (3×SSC). There is no evidence of any other hybridising bands, as it can be concluded that this shows a single-copy of the phytase gene in the transformed A. nidulans. No hybridising bands can be seen in the untransformed sample, indicating that there is no homology between the *P. hordei* phytase and any phytases present in the *A. nidulans* genome.

5E. Biochemical Characterisation of *P. hordei* Phytase

To prove that the cloned gene represents a specific phytase activity, and to characterise that activity, a range of biochemical analyses were carried out on the over-expressed enzyme. Preliminary characterisation had indicated that the gene was producing a phytic-acid hydrolysing activity. This analysis was extended to examine activity at different pHs, temperatures and against different substrates.

Transformant CS213-4 was taken forward for these analyses, and cultures were harvested at 3-days. With phytic acid as the substrate, the enzyme showed activity between pH 3.0 and 7.0 (FIG. 15). The purified enzyme sample was desalted from culture supernatant, and eluted in 0.025 mM sodium acetate pH 5.0. This was then added to substrate which was made in solutions of the following buffers: pH 3.0: 0.4M glycine-HCl, pH 4.0: 0.4M Sodium acetate, pH 5.0: 0.4M Sodium acetate, pH 6.0: 0.4M imidazole-HCl, pH 7.0: 0.4M Tris-HCl, pH 8.0: 0.4M Tris-HCl pH 9.0: 0.4M Tris-HCl. There was a clear optimum at pH 5.0 (240 units per mL of supernatant), with a broad shoulder of activity from 5.0 down to 6.0. When 4-nitrophenyl-phosphate was used as the substrate, there was very little activity seen, indicating a high level of specificity for the phytic-acid substrate. The highest activity against this substrate appears to be at pH 3.0, but even this is 25% of the activity against phytic acid at this pH. The temperature profile of the enzyme was characterised using pH 5.0 buffer, over a range of temperatures, this time only using phytic acid as the substrate (FIG. 16). The *P. hordei* phytase showed activity from 30° C. to 85° C., but had a clear temperature optimum at 44° C. The enzyme had much higher activity at more ambient temperatures, and only lost 22% of relative activity between 44° C. and 37° C. As the total level of protein produced was very low, and the assays were performed on total supernatant protein, it was difficult to determine the specific activity of this phytase. The average total protein for these samples was 8 μgmL-1, which would give a projected specific activity of 240000 units per mg of protein.

Preliminary stability studies were also carried out on the phytase. Samples of the 3-day protein were left at −20° C., 4° C., and 37° C. overnight, and then assayed under standard conditions. No residual activity was determined. Samples were also exposed to 85° C. for 20 minutes, and 100° C. for 10 minutes to determine the thermostability of the phytase activity. When assayed after exposure to these temperatures at 37° C., pH 5.0, there is a substantial decrease in residual enzyme activity (Table 6).

TABLE 6

| Stability condition | Residual activity (%) |
|---|---|
| 85° C. for 20 min | 20% |
| 100° C. for 10 min | 21% |
| −20° C. for 24 hours | ND |
| 4° C. for 24 hours | ND |
| 37° C. for 24 hours | ND |

Residual activity is based on comparison to phytase activity determinations taken from the samples before exposure to each condition (100% activity corresponded to 112 units per mL of culture supernatant). These were standard phytase assay conditions of pH 5.0, 37° C. for 30 min, although samples were only assayed in duplicate. Samples were assayed afterwards in the same assay conditions.

Example 6

Cloning and Analysis of Phytase Gene Fragments from *Penicillium piceum*

Two primers were designed to amplify phytase gene fragments from this fungal target (Table 7). CS11 was designed from the DNA sequence of cloned phytase genes (*A. niger, A. fumigatus, E. nidulans* and *T. thermophilus*), the gene sequence of the cloned phytase from *P.hordei*, and the sequences of the designed primers CS1 and N1. The first two bases in each codon for this primer are well conserved. The third base was chosen based on the bias shown in the published DNA sequences, and in particular the base in the third position in the sequence of *P. hordei*. CS12 was designed from the conserved amino acid motif YADFISHDN from published phytase sequences, and from the deduced amino acid sequence of the *P. hordei* phytase gene.

TABLE 7

Sequences of degenerate primers designed from sequences conserved among fungal phytases

| Primer | Region | Sequence |
|---|---|---|
| CS11 (F) | 5' redesigned CS1 primer from phytase motif RHGARYP | 5' CG(T/G/C) CA(C/T) GG(A/G/C) GC(G/T) CG(G/C) TA(C/T) CC(A/G/T) (A/T)C 3' (SEQ ID NO:33) |
| CS12 (R) | 3' reverse primer designed from phytase motif YADFTHDN | 5' (A/G)TT (A/G)TC (A/G)TG (A/G/C/T)(G/C)(A/G) (A/G)AA (A/G)TC (A/C/G/T)(A/G)C (A/G)TA 3' (SEQ ID NO:34) |

F indicates a forward primer (5' → 3') on the positive strand. R indicates a reverse primer on the negative strand.

PCR was carried out on genomic samples of *P. piceum* DNA, and amplified a fragment of approximately 800 bp, which was the expected size. This fragment was cloned into pTT-vector, and standard transformation in *E. coli* XLI-blue cell was done. A selection of transformants were selected, and plasmid DNA isolated. A selection of clones with the correct sized insert were sent off for sequencing to MWG-Biotech. One clone, CS142 contained sequence that had high homology to phytases. The deduced amino acid sequence showed that the fragment cloned (853 bp) was from a phytase gene. The genomic and deduced amino acid sequences from the *P. piceum* fragment are illustrated in FIG. 17. It had the expected number of Cys residues for that region (3), and contained all the crucial motifs for phytase structure and function, notably:

RHGARYP

3×Cys

HD (within the YADFTHDN)

There are a number of other well conserved regions present here (see alignment FIG. 5) and % identity analysis using this alignment showed the *P. piceum* had a approximate 51% identity to *P. hordei* phytase. This fragment of *P. piceum* phytase (283 amino acid) represents approximately 65% of the full phytase.

Southern analysis of the *P.piceum* fragment against digests of *A. niger, P. hordei, P.piceum* and *P. brevicompactum* under conditions of medium stringency (3×SSC), showed hybridisation against the *P. piceum* digests only.

Of course, it should be understood that a wide range of changes and modifications can be made to the preferred embodiment described above. It is therefore intended that the foregoing detailed description be understood in the context of the following claims, including all equivalents, which are intended to define the scope of this invention.

It is claimed:

1. An isolated polynucleotide encoding an enzyme having phytase activity, wherein said enzyme comprises an amino acid sequence having at least 70% identity to the amino acid sequence disclosed in SEQ ID NO:4.

2. An isolated polynucleotide comprising a nucleotide sequence complementary to the nucleotide sequence disclosed in SEQ ID NO:1, SEQ ID NO:2, or SEQ ID NO:3.

3. An isolated polynucleotide encoding an enzyme having phytase activity comprising a nucleotide sequence having at least 75% identity to the nucleotide sequence disclosed in SEQ ID NO: 1, SEQ ID NO:2, or SEQ ID NO:3, and wherein said enzyme comprises an amino acid sequence having at least 80% identity to the amino acid sequence disclosed in SEQ ID NO: 4.

4. The isolated polynucleotide of claim 1, wherein said enzyme comprises an amino acid sequence having at least 80% identity with the sequence disclosed in SEQ ID NO: 4.

5. The isolated polynucleotide of claim 1, wherein said enzyme comprises an amino acid sequence having at least 90% identity with the sequence disclosed in SEQ ID NO: 4.

6. The isolated polynucleotide of claim 1, wherein said enzyme comprises the amino acid sequence disclosed in SEQ ID NO: 4.

7. The isolated polynucleotide of claim 1, wherein the polynucleotide is SEQ ID NO: 1.

8. The isolated polynucleotide of claim 1, wherein the polynucleotide is SEQ ID NO: 2.

9. The isolated polynucleotide of claim 1, wherein the polynucleotide is SEQ ID NO: 3.

10. The isolated polynucleotide of claim 3, wherein the pqlynucleotide sequence has at least 85% sequence identity to SEQ ID NO: 1, SEQ ID NO: 2 or SEQ ID NO: 3.

11. The isolated polynucleotide of claim 10, wherein the polynucleotide sequence has at least 90% sequence identity to SEQ ID NO: 1, SEQ ID NO: 2 or SEQ ID NO: 3.

12. The isolated polynucleotide of claim 11, wherein the polynucleotide sequence has at least 95% sequence identity to SEQ ID NO: 1, SEQ ID NO: 2 or SEQ ID NO: 3.

13. An isolated polynucleotide encoding an enzyme having phytase activity comprising a nucleotide sequence having at least 90% identity to the nucleotide sequence disclosed in SEQ ID NO: 1, SEQ ID NO: 2, or SEQ ID NO: 3, wherein said enzyme comprises an amino acid sequence having at least 90% identity to the amino acid sequence disclosed in SEQ ID NO: 4.

14. The isolated polynucleotide of claim 1, wherein said polynucleotide is obtained from a Penicillium sp.

15. The isolated polynucleotide of claim 14, wherein Penicillium sp. is *Penicillium piceum.*

16. The isolated polynucleotide of claim 3, wherein said polynucleotide is obtained from a Penicillium sp.

17. The isolated polynucleotide of claim 14, wherein Penicillium sp. is *Penicillium piceum.*

18. A vector comprising the polynucleotide of claim 1.

19. A vector comprising the polynucleotide of claim 3.

20. A host cell transformed with the vector of claim 18.

21. A host cell transformed with the vector of claim 19.

22. The host cell of claim 20, wherein said host cell is an Aspergillus cell.

23. The host cell of claim 21, wherein said host cell is an Aspergillus cell.

24. A host cell transformed with the polynucleotide of claim 11.

25. A host cell transformed with the polynucleotide of claim 13.

26. A method of producing an enzyme having phytase activity, comprising:

(a) providing a host cell transformed with an expression vector comprising a polynucleotide as defined in claim 1;

(b) cultivating said transformed host cell under conditions suitable for said host cell to produce said phytase; and (c) recovering said phytase.

27. The method of claim 26, wherein said host cell is an Aspergillus species.

28. A method of producing an enzyme having phytase activity, comprising:

(a) providing a host cell transformed with an expression vector comprising a polynucleotide as defined in claim 3;

(b) cultivating said transformed host cell under conditions suitable for said host cell to produce said phytase; and (c) recovering said phytase.

29. The method according to claim 28, wherein the host cell is an Aspergillus cell.

30. A probe comprising the polynucleotide of claim 1, wherein said probe is used to detect a nucleic acid sequence coding for an enzyme having phytase activity, and wherein said nucleic acid sequence is obtained from a microbial source.

31. The probe of claim 30, wherein said microbial source is a fungal source.

32. The probe of claim 31, wherein said fungal source is a Penicillium species.

33. The probe of claim 30, wherein said probe comprises the polynucleotide shown in SEQ ID NO: 1.

34. The probe of claim 30, wherein said probe comprises the polynucleotide shown in SEQ ID NO: 2.

35. The probe of claim 30, wherein said probe comprises the polynucteotide shown in SEQ ID NO: 3.

* * * * *

```
                         SEQUENCE LISTING

<160> NUMBER OF SEQ ID NOS: 34

<210> SEQ ID NO 1
<211> LENGTH: 1922
<212> TYPE: DNA
<213> ORGANISM: Penicillium hordei

<400> SEQUENCE: 1

gctatgcatc aagcttggta ccgagctcgg atccactagt aacggccgcc agtgtgctgg      60

aattcgccct ttctgatatc tcgatatcct tgcaggttcc acgtacttgt cgtgataccc     120

tctactcatt cactaggtgc aatggcagcg ttctccaaag aaaagcatgg ggaggaagag     180

ggcctacttg gcgagagcca agatcaaggc cggaagcagc aacgccagcg atcggcccaa     240

aaatggcgta caattaccct agtatccctg ctgggcgctt tcgccctgtt tgtgtacttc     300

gcgaaggggt cccagtgcaa ccgccccccc tcgcatgtca caacccagcc cgacctacct     360

gtggcttttc ccctgaacaa gtcgaagcga tcatcgcatc acgaacatgc ctgcaatact     420

gttgatggcg gttatcaatg caactcctcg ctctcgcaca agtggggcca atattcgccc     480

tatttctctc tttctgacga atcggccatc tcagatgagg tacctcacgg ttgtcagatc     540

acttttgctc aggtgatctc ccgtcatggt gctcgattcc cgtcggcgaa aaagagcaag     600

gcatatgccg cgctcgttaa aagcatccaa gcgaacgcga cttcatacaa gggcaacacg     660

gaattcatcc gctcatacaa ctacaccatg ggcggtgatg atttggtacc ctttggagtg     720

aaccagatgg tgagctcggg aaccaagttc taccagcgct atgcggcgtt agctaaaaag     780

gccgtgcctt tcattcgcat atctgactcg gagcgggttg tggcttcagg agtgaacttc     840

atcaagggct ttcagaagga aaagttgaat gacaagcatg ccaatcaccg tcaatcaagc     900

cctaaggtca atgtcctcat ctcggaagag tctggcacca acaacactct gaaccacagt     960

gagatctgtg ccaagttcga agaaagtgaa ctaggcgacg aggtcgaaga aaaatacatg    1020

gcaatctttg tgccgcccat ccgagcccgt cttgaggcta acctccctgg catcaaactt    1080

gaagacatcg atgtgatcaa tctgatggat atttgcccct tcgagacagt gtccctgact    1140

agcgatggat ccaagctatc tccattctgc aacctcttca cccaggccga atgggaccaa    1200

tacgactacc tccagtcact gagcaagtac tacggttatg gcgcaggcaa cccgctcggc    1260

ccaacccagg gtgtcggttt cgtgaacgaa ctcattgccc gtctcactca cgccccagtg    1320

gtcgacaaca caagcacaaa ccgtacactc gatgcccccg gcgctgcgac attccccctc    1380

aactacacca tgtacgcaga cttcacgcac gacaatggaa tgattccgtt cttctttgct    1440

ttgggactgt acaacggcac ttctccactc tccctcacca aggcccagtc aactaacgaa    1500

acggacggat tttcagccgc ctggacggtg cctttcggtg ctcgtgctta tgtcgagatg    1560

atgcaatgtc gccgcgaccc ggagccgctc gtgcgagtcc tcgttaacga ccgtgttgtt    1620

ccgctgcatg gttgccccgt cgataagctt ggccgttgtc gccgtcgcga tttcgtcaag    1680

ggactcactt ttgcgcgctc tggcggtgat tggccccagt gctatgaata ggagattttg    1740

aaaataattg gtgcagggtt ggtcctcttc caacgtactt ttgtctagcg ataccccaaa    1800

gattgcatcc ttacatacat atccttcttt cttttggcca atattaatgc accggtgccg    1860
```

-continued aagggcgaat tctgcagata tccatcacac tggcggccgt cgagcatgca tctagaggcc 1920
ca 1922

<210> SEQ ID NO 2
<211> LENGTH: 1584
<212> TYPE: DNA
<213> ORGANISM: Penicillium hordei

<400> SEQUENCE: 2
gcagcgttct ccaaagaaaa gcatggggag gaagagggcc tacttggcga gagccaagat 60
caaggccgga agcagcaacg ccagcgatcg gcccaaaaat ggcgtacaat taccctagta 120
tccctgctgg gcgctttcgc cctgtttgtg tacttcgcga aggggtccca gtgcaaccgc 180 ccccctcgc atgtcacaac ccagcccgac ctacctgtgg cttttcccct gaacaagtcg 240
aagcgatcat cgcatcacga acatgcctgc aatactgttg atggcggtta tcaatgcaac 300
tcctcgctct cgcacaagtg gggccaatat tcgccctatt tctctctttc tgacgaatcg 360
gccatctcag atgaggtacc tcacggttgt cagatcactt ttgctcaggt gatctcccgt 420
catggtgctc gattcccgtc ggcgaaaaag agcaaggcat atgccgcgct cgttaaaagc 480
atccaagcga acgcgacttc atacaagggc aacacggaat tcatccgctc atacaactac 540
accatgggcg gtgatgattt ggtacccttt ggagtgaacc agatggtgag ctcgggaacc 600
aagttctacc agcgctatgc ggcgttagct aaaaaggccg tgcctttcat tcgcatatct 660
gactcggagc gggttgtggc ttcaggagtg aacttcatca agggctttca gaaggaaaag 720
ttgaatgaca agcatgccaa tcaccgtcaa tcaagcccta aggtcaatgt cctcatctcg 780
gaagagtctg gcaccaacaa cactctgaac cacagtgaga tctgtgccaa gttcgaagaa 840
agtgaactag gcgacgaggt cgaagaaaaa tacatggcaa tctttgtgcc gcccatccga 900
gcccgtcttg aggctaacct ccctggcatc aaacttgaag acatcgatgt gatcaatctg 960
atggatattt gccccttcga gacagtgtcc ctgactagcg atggatccaa gctatctcca 1020
ttctgcaacc tcttcaccca ggccgaatgg gaccaatacg actacctcca gtcactgagc 1080
aagtactacg gttatggcgc aggcaacccg ctcggcccaa cccagggtgt cggtttcgtg 1140
aacgaactca ttgcccgtct cactcacgcc ccagtggtcg acaacacaag cacaaaccgt 1200
acactcgatg cccccggcgc tgcgacattc cccctcaact acaccatgta cgcagacttc 1260
acgcacgaca atggaatgat tccgttcttc tttgctttgg gactgtacaa cggcacttct 1320
ccactctccc tcaccaaggc ccagtcaact aacgaaacgg acggattttc agccgcctgg 1380
acggtgcctt tcggtgctcg tgcttatgtc gagatgatgc aatgtcgccg cgacccggag 1440
ccgctcgtgc gagtcctcgt taacgaccgt gttgttccgc tgcatggttg ccccgtcgat 1500
aagcttggcc gttgtcgccg tcgcgatttc gtcaagggac tcacttttgc gcgctctggc 1560
ggtgattggc cccagtgcta tgaa 1584

<210> SEQ ID NO 3
<211> LENGTH: 1464
<212> TYPE: DNA
<213> ORGANISM: Penicillium hordei

<400> SEQUENCE: 3
gcagcgttct ccaaagaaaa gcatggggag gaagagggcc tacttggcga gagccaagat 60
caaggccgga agcagcaacg ccagcgatcg gcccaaaaat ggcgtacaat taccctatcg 120
aagcgatcat cgcatcacga acatgcctgc aatactgttg atggcggtta tcaatgcaac 180

-continued

```
tcctcgctct cgcacaagtg gggccaatat tcgccctatt tctctctttc tgacgaatcg    240

gccatctcag atgaggtacc tcacggttgt cagatcactt ttgctcaggt gatctcccgt    300

catggtgctc gattcccgtc ggcgaaaaag agcaaggcat atgccgcgct cgttaaaagc    360

atccaagcga acgcgacttc atacaagggc aacacggaat tcatccgctc atacaactac    420

accatgggcg gtgatgattt ggtacccttt ggagtgaacc agatggtgag ctcgggaacc    480

aagttctacc agcgctatgc ggcgttagct aaaaaggccg tgcctttcat tcgcatatct    540

gactcggagc gggttgtggc ttcaggagtg aacttcatca agggctttca gaaggaaaag    600

ttgaatgaca agcatgccaa tcaccgtcaa tcaagcccta aggtcaatgt cctcatctcg    660

gaagagtctg gcaccaacaa cactctgaac cacagtgaga tctgtgccaa gttcgaagaa    720

agtgaactag gcgacgaggt cgaagaaaaa tacatggcaa tctttgtgcc gcccatccga    780

gcccgtcttg aggctaacct ccctggcatc aaacttgaag acatcgatgt gatcaatctg    840

atggatattt gccccttcga gacagtgtcc ctgactagcg atggatccaa gctatctcca    900

ttctgcaacc tcttcaccca ggccgaatgg gaccaatacg actacctcca gtcactgagc    960

aagtactacg gttatggcgc aggcaacccg ctcggcccaa cccagggtgt cggtttcgtg   1020

aacgaactca ttgcccgtct cactcacgcc ccagtggtcg acaacacaag cacaaaccgt   1080

acactcgatg cccccggcgc tgcgacattc cccctcaact acaccatgta cgcagacttc   1140

acgcacgaca atggaatgat tccgttcttc tttgctttgg gactgtacaa cggcacttct   1200

ccactctccc tcaccaaggc ccagtcaact aacgaaacgg acggattttc agccgcctgg   1260

acggtgcctt tcggtgctcg tgcttatgtc gagatgatgc aatgtcgccg cgacccggag   1320

ccgctcgtgc gagtcctcgt taacgaccgt gttgttccgc tgcatggttg ccccgtcgat   1380

aagcttggcc gttgtcgccg tcgcgatttc gtcaagggac tcacttttgc gcgctctggc   1440

ggtgattggc cccagtgcta tgaa                                          1464
```

```
<210> SEQ ID NO 4
<211> LENGTH: 489
<212> TYPE: PRT
<213> ORGANISM: Penicillium hordei

<400> SEQUENCE: 4

Met Ala Ala Phe Ser Lys Glu Lys His Gly Glu Glu Glu Gly Leu Leu
 1               5                  10                  15

Gly Glu Ser Gln Asp Gln Gly Arg Lys Gln Gln Arg Gln Arg Ser Ala
            20                  25                  30

Gln Lys Trp Arg Thr Ile Thr Leu Ser Lys Arg Ser Ser His His Glu
        35                  40                  45

His Ala Cys Asn Thr Val Asp Gly Gly Tyr Gln Cys Asn Ser Ser Leu
    50                  55                  60

Ser His Lys Trp Gly Gln Tyr Ser Pro Tyr Phe Ser Leu Ser Asp Glu
65                  70                  75                  80

Ser Ala Ile Ser Asp Glu Val Pro His Gly Cys Gln Ile Thr Phe Ala
                85                  90                  95

Gln Val Ile Ser Arg His Gly Ala Arg Phe Pro Ser Ala Lys Lys Ser
            100                 105                 110

Lys Ala Tyr Ala Ala Leu Val Lys Ser Ile Gln Ala Asn Ala Thr Ser
        115                 120                 125

Tyr Lys Gly Asn Thr Glu Phe Ile Arg Ser Tyr Asn Tyr Thr Met Gly
    130                 135                 140
```

-continued

Gly Asp Asp Leu Val Pro Phe Gly Val Asn Gln Met Val Ser Ser Gly
145 150 155 160

Thr Lys Phe Tyr Gln Arg Tyr Ala Ala Leu Ala Lys Lys Ala Val Pro
165 170 175

Phe Ile Arg Ile Ser Asp Ser Glu Arg Val Val Ala Ser Gly Val Asn
180 185 190

Phe Ile Lys Gly Phe Gln Lys Glu Lys Leu Asn Asp Lys His Ala Asn
195 200 205

His Arg Gln Ser Ser Pro Lys Val Asn Val Leu Ile Ser Glu Glu Ser
210 215 220

Gly Thr Asn Asn Thr Leu Asn His Ser Glu Ile Cys Ala Lys Phe Glu
225 230 235 240

Glu Ser Glu Leu Gly Asp Glu Val Glu Glu Lys Tyr Met Ala Ile Phe
245 250 255

Val Pro Pro Ile Arg Ala Arg Leu Glu Ala Asn Leu Pro Gly Ile Lys
260 265 270

Leu Glu Asp Ile Asp Val Ile Asn Leu Met Asp Ile Cys Pro Phe Glu
275 280 285

Thr Val Ser Leu Thr Ser Asp Gly Ser Lys Leu Ser Pro Phe Cys Asn
290 295 300

Leu Phe Thr Gln Ala Glu Trp Asp Gln Tyr Asp Tyr Leu Gln Ser Leu
305 310 315 320

Ser Lys Tyr Tyr Gly Tyr Gly Ala Gly Asn Pro Leu Gly Pro Thr Gln
325 330 335

Gly Val Gly Phe Val Asn Glu Leu Ile Ala Arg Leu Thr His Ala Pro
340 345 350

Val Val Asp Asn Thr Ser Thr Asn Arg Thr Leu Asp Ala Pro Gly Ala
355 360 365

Ala Thr Phe Pro Leu Asn Tyr Thr Met Tyr Ala Asp Phe Thr His Asp
370 375 380

Asn Gly Met Ile Pro Phe Phe Phe Ala Leu Gly Leu Tyr Asn Gly Thr
385 390 395 400

Ser Pro Leu Ser Leu Thr Lys Ala Gln Ser Thr Asn Glu Thr Asp Gly
405 410 415

Phe Ser Ala Ala Trp Thr Val Pro Phe Gly Ala Arg Ala Tyr Val Glu
420 425 430

Met Met Gln Cys Arg Arg Asp Pro Glu Pro Leu Val Arg Val Leu Val
435 440 445

Asn Asp Arg Val Val Pro Leu His Gly Cys Pro Val Asp Lys Leu Gly
450 455 460

Arg Cys Arg Arg Arg Asp Phe Val Lys Gly Leu Thr Phe Ala Arg Ser
465 470 475 480

Gly Gly Asp Trp Pro Gln Cys Tyr Glu
485

<210> SEQ ID NO 5
<211> LENGTH: 467
<212> TYPE: PRT
<213> ORGANISM: Aspergillus niger

<400> SEQUENCE: 5

Met Gly Val Ser Ala Val Leu Leu Pro Leu Tyr Leu Leu Ser Gly Val
1 5 10 15

Thr Ser Gly Leu Ala Val Pro Ala Ser Arg Asn Gln Ser Ser Cys Asp

-continued

```
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
        435                 440                 445
```

-continued

```
Phe Val Arg Gly Leu Ser Phe Ala Arg Ser Gly Gly Asp Trp Ala Glu
    450                 455                 460

Cys Phe Ala
465


<210> SEQ ID NO 6
<211> LENGTH: 465
<212> TYPE: PRT
<213> ORGANISM: Aspergillus fumigatus

<400> SEQUENCE: 6

Met Val Thr Leu Thr Phe Leu Leu Ser Ala Ala Tyr Leu Leu Ser Gly
 1               5                  10                  15

Arg Val Ser Ala Ala Pro Ser Ser Ala Gly Ser Lys Ser Cys Asp Thr
            20                  25                  30

Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
        195                 200                 205

Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
```

-continued

```
            340                 345                 350

Met Tyr Val Asp Phe Ser His Asp Asn Ser Met Val Ser Ile Phe Phe
        355                 360                 365

Ala Leu Gly Leu Tyr Asn Gly Thr Glu Pro Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
        435                 440                 445

Lys Gly Leu Ser Trp Ala Arg Ser Gly Gly Asn Trp Gly Glu Cys Phe
    450                 455                 460

Ser
465


<210> SEQ ID NO 7
<211> LENGTH: 466
<212> TYPE: PRT
<213> ORGANISM: Aspergillus terreus

<400> SEQUENCE: 7

Met Gly Phe Leu Ala Ile Val Leu Ser Val Ala Leu Leu Phe Arg Ser
 1               5                  10                  15

Thr Ser Gly Thr Pro Leu Gly Pro Arg Gly Lys His Ser Asp Cys Asn
            20                  25                  30

Ser Val Asp His Gly Tyr Gln Cys Phe Pro Glu Leu Ser His Lys Trp
        35                  40                  45

Gly Leu Tyr Ala Pro Tyr Phe Ser Leu Gln Asp Glu Ser Pro Phe Pro
    50                  55                  60

Leu Asp Val Pro Glu Asp Cys His Ile Thr Phe Val Gln Val Leu Ala
65                  70                  75                  80

Arg His Gly Ala Arg Ser Pro Thr His Ser Lys Thr Lys Ala Tyr Ala
                85                  90                  95

Ala Thr Ile Ala Ala Ile Gln Lys Ser Ala Thr Ala Phe Pro Gly Lys
            100                 105                 110

Tyr Ala Phe Leu Gln Ser Tyr Asn Tyr Ser Leu Asp Ser Glu Glu Leu
        115                 120                 125

Thr Pro Phe Gly Arg Asn Gln Leu Arg Asp Leu Gly Ala Gln Phe Tyr
    130                 135                 140

Glu Arg Tyr Asn Ala Leu Thr Arg His Ile Asn Pro Phe Val Arg Ala
145                 150                 155                 160

Thr Asp Ala Ser Arg Val His Glu Ser Ala Glu Lys Phe Val Glu Gly
                165                 170                 175

Phe Gln Thr Ala Arg Gln Asp Asp His His Ala Asn Pro His Gln Pro
            180                 185                 190

Ser Pro Arg Val Asp Val Ala Ile Pro Glu Gly Ser Ala Tyr Asn Asn
        195                 200                 205

Thr Leu Glu His Ser Leu Cys Thr Ala Phe Glu Ser Ser Thr Val Gly
    210                 215                 220

Asp Asp Ala Val Ala Asn Phe Thr Ala Val Phe Ala Pro Ala Ile Ala
225                 230                 235                 240
```

-continued

```
Gln Arg Leu Glu Ala Asp Leu Pro Gly Val Gln Leu Ser Thr Asp Asp
                245                 250                 255

Val Val Asn Leu Met Ala Met Cys Pro Phe Glu Thr Val Ser Leu Thr
            260                 265                 270

Asp Asp Ala His Thr Leu Ser Pro Phe Cys Asp Leu Phe Thr Ala Thr
        275                 280                 285

Glu Trp Thr Gln Tyr Asn Tyr Leu Leu Ser Leu Asp Lys Tyr Tyr Gly
    290                 295                 300

Tyr Gly Gly Gly Asn Pro Leu Gly Pro Val Gln Gly Val Gly Trp Ala
305                 310                 315                 320

Asn Glu Leu Met Ala Arg Leu Thr Arg Ala Pro Val His Asp His Thr
                325                 330                 335

Cys Val Asn Asn Thr Leu Asp Ala Ser Pro Ala Thr Phe Pro Leu Asn
            340                 345                 350

Ala Thr Leu Tyr Ala Asp Phe Ser His Asp Ser Asn Leu Val Ser Ile
        355                 360                 365

Phe Trp Ala Leu Gly Leu Tyr Asn Gly Thr Ala Pro Leu Ser Gln Thr
    370                 375                 380

Ser Val Glu Ser Val Ser Gln Thr Asp Gly Tyr Ala Ala Ala Trp Thr
385                 390                 395                 400

Val Pro Phe Ala Ala Arg Ala Tyr Val Glu Met Met Gln Cys Arg Ala
                405                 410                 415

Glu Lys Glu Pro Leu Val Arg Val Leu Val Asn Asp Arg Val Met Pro
            420                 425                 430

Leu His Gly Cys Pro Thr Asp Lys Leu Gly Arg Cys Lys Arg Asp Ala
        435                 440                 445

Phe Val Ala Gly Leu Ser Phe Ala Gln Ala Gly Gly Asn Trp Ala Asp
    450                 455                 460

Cys Phe
465


<210> SEQ ID NO 8
<211> LENGTH: 487
<212> TYPE: PRT
<213> ORGANISM: Myceliophthora thermophila

<400> SEQUENCE: 8

Met Thr Gly Leu Gly Val Met Val Val Met Val Gly Phe Leu Ala Ile
 1               5                  10                  15

Ala Ser Leu Gln Ser Glu Ser Arg Pro Cys Asp Thr Pro Asp Leu Gly
            20                  25                  30

Phe Gln Cys Gly Thr Ala Ile Ser His Phe Trp Gly Gln Tyr Ser Pro
        35                  40                  45

Tyr Phe Ser Val Pro Ser Glu Leu Asp Ala Ser Ile Pro Asp Asp Cys
    50                  55                  60

Glu Val Thr Phe Ala Gln Val Leu Ser Arg His Gly Ala Arg Ala Pro
65                  70                  75                  80

Thr Leu Lys Arg Ala Ala Ser Tyr Val Asp Leu Ile Asp Arg Ile His
                85                  90                  95

His Gly Ala Ile Ser Tyr Gly Pro Gly Tyr Glu Phe Leu Arg Thr Tyr
            100                 105                 110

Asp Tyr Thr Leu Gly Ala Asp Glu Leu Thr Arg Thr Gly Gln Gln Gln
        115                 120                 125

Met Val Asn Ser Gly Ile Lys Phe Tyr Arg Arg Tyr Arg Ala Leu Ala
    130                 135                 140
```

-continued

```
Arg Lys Ser Ile Pro Phe Val Arg Thr Ala Gly Gln Asp Arg Val Val
145                 150                 155                 160

His Ser Ala Glu Asn Phe Thr Gln Gly Phe His Ser Ala Leu Leu Ala
                165                 170                 175

Asp Arg Gly Ser Thr Val Arg Pro Thr Leu Pro Tyr Asp Met Val Val
            180                 185                 190

Ile Pro Glu Thr Ala Gly Ala Asn Asn Thr Leu His Asn Asp Leu Cys
        195                 200                 205

Thr Ala Phe Glu Glu Gly Pro Tyr Ser Thr Ile Gly Asp Asp Ala Gln
    210                 215                 220

Asp Thr Tyr Leu Ser Thr Phe Ala Gly Pro Ile Thr Ala Arg Val Asn
225                 230                 235                 240

Ala Asn Leu Pro Gly Ala Asn Leu Thr Asp Ala Asp Thr Val Ala Leu
                245                 250                 255

Met Asp Leu Cys Pro Phe Glu Thr Val Ala Ser Ser Ser Ser Asp Pro
            260                 265                 270

Ala Thr Ala Asp Ala Gly Gly Gly Asn Gly Arg Pro Leu Ser Pro Phe
        275                 280                 285

Cys Arg Leu Phe Ser Glu Ser Glu Trp Arg Ala Tyr Asp Tyr Leu Gln
    290                 295                 300

Ser Val Gly Lys Trp Tyr Gly Tyr Gly Pro Gly Asn Pro Leu Gly Pro
305                 310                 315                 320

Thr Gln Gly Val Gly Phe Val Asn Glu Leu Leu Ala Arg Leu Ala Gly
                325                 330                 335

Val Pro Val Arg Asp Gly Thr Ser Thr Asn Arg Thr Leu Asp Gly Asp
            340                 345                 350

Pro Arg Thr Phe Pro Leu Gly Arg Pro Leu Tyr Ala Asp Phe Ser His
        355                 360                 365

Asp Asn Asp Met Met Gly Val Leu Gly Ala Leu Gly Ala Tyr Asp Gly
    370                 375                 380

Val Pro Pro Leu Asp Lys Thr Ala Arg Arg Asp Pro Glu Glu Leu Gly
385                 390                 395                 400

Gly Tyr Ala Ala Ser Trp Ala Val Pro Phe Ala Ala Arg Ile Tyr Val
                405                 410                 415

Glu Lys Met Arg Cys Ser Gly Gly Gly Gly Gly Gly Gly Gly Gly Glu
            420                 425                 430

Gly Arg Gln Glu Lys Asp Glu Glu Met Val Arg Val Leu Val Asn Asp
        435                 440                 445

Arg Val Met Thr Leu Lys Gly Cys Gly Ala Asp Glu Arg Gly Met Cys
    450                 455                 460

Thr Leu Glu Arg Phe Ile Glu Ser Met Ala Phe Ala Arg Gly Asn Gly
465                 470                 475                 480

Lys Trp Asp Leu Cys Phe Ala
                485


<210> SEQ ID NO 9
<211> LENGTH: 283
<212> TYPE: PRT
<213> ORGANISM: Penicillium piceum

<400> SEQUENCE: 9

Arg His Gly Ala Arg Tyr Pro Thr Ser Tyr Lys Asp Glu Lys Tyr Ala
 1               5                  10                  15

Glu Leu Val Asp Asn Ile His Lys Thr Ala Thr Ala Tyr Met Gly Asp
```

-continued

```
            20                  25                  30

Phe Ser Val Leu Lys Asp Tyr Lys Tyr Gln Leu Gly Ala Asn Asn Leu
        35                  40                  45

Thr Glu Leu Gly Gln Gln Gln Leu Ile Val Ser Gly Met Arg Phe Tyr
    50                  55                  60

Glu Arg Tyr Arg Ser Leu Ala Arg Asp Asn Val Pro Phe Val Arg Ser
65                  70                  75                  80

Ala Gly Ser Thr Arg Val Val Ala Ser Gly Asp Phe Phe Asn Gln Gly
                85                  90                  95

Phe Gln Ala Ala Lys Asp Arg Asp Pro Val Ser Asn Lys Thr Gln Gln
            100                 105                 110

Pro Pro Val Ile Asn Val Ile Ile Pro Glu Gly Ser Gln Trp Asn Asn
        115                 120                 125

Thr Leu Asp Val Thr Thr Cys Pro Ser Phe Gln Asn Asp Thr Ser Ala
    130                 135                 140

Asp Thr Ala Gln Glu Lys Phe Leu Asn Val Phe Ala Pro Ser Ile Leu
145                 150                 155                 160

Gln Lys Ile Thr Ala Gly Leu Pro Gly Thr Gln Leu Lys Val Glu Asp
                165                 170                 175

Val Pro Leu Ile Met Asp Leu Cys Pro Phe Glu Thr Val Ala Asn Pro
            180                 185                 190

Asn Thr Ser Thr Gln Leu Ser Pro Leu Cys Asp Leu Phe Thr Leu Ser
        195                 200                 205

Glu Trp Gln Ser Tyr Asp Tyr Tyr Asn Thr Leu Gly Lys Tyr Tyr Gly
    210                 215                 220

His Gly Gln Gly Asn Pro Leu Gly Pro Thr Gln Gly Val Gly Phe Val
225                 230                 235                 240

Asn Glu Val Ile Ala Arg Met Thr Gln Ser Pro Val Lys Asp His Thr
                245                 250                 255

Ser Val Asn Asn Thr Leu Asp Ser Asp Ala Thr Thr Phe Pro Leu Gly
            260                 265                 270

Pro Ala Leu Tyr Ala Asp Phe Pro His Asp Asn
        275                 280


<210> SEQ ID NO 10
<211> LENGTH: 489
<212> TYPE: PRT
<213> ORGANISM: Penicillium hordei

<400> SEQUENCE: 10

Met Ala Ala Phe Ser Lys Glu Lys His Gly Glu Glu Glu Gly Leu Leu
 1               5                  10                  15

Gly Glu Ser Gln Asp Gln Gly Arg Lys Gln Gln Arg Gln Arg Ser Ala
            20                  25                  30

Gln Lys Trp Arg Thr Ile Thr Leu Ser Lys Arg Ser Ser His His Glu
        35                  40                  45

His Ala Cys Asn Thr Val Asp Gly Gly Tyr Gln Cys Asn Ser Ser Leu
    50                  55                  60

Ser His Lys Trp Gly Gln Tyr Ser Pro Tyr Phe Ser Leu Ser Asp Glu
65                  70                  75                  80

Ser Ala Ile Ser Asp Glu Val Pro His Gly Cys Gln Ile Thr Phe Ala
                85                  90                  95

Gln Val Ile Ser Arg His Gly Ala Arg Phe Pro Ser Ala Lys Lys Ser
            100                 105                 110
```

-continued

Lys Ala Tyr Ala Ala Leu Val Lys Ser Ile Gln Ala Asn Ala Thr Ser
115 120 125

Tyr Lys Gly Asn Thr Glu Phe Ile Arg Ser Tyr Asn Tyr Thr Met Gly
130 135 140

Gly Asp Asp Leu Val Pro Phe Gly Val Asn Gln Met Val Ser Ser Gly
145 150 155 160

Thr Lys Phe Tyr Gln Arg Tyr Ala Ala Leu Ala Lys Lys Ala Val Pro
165 170 175

Phe Ile Arg Ile Ser Asp Ser Glu Arg Val Val Ala Ser Gly Val Asn
180 185 190

Phe Ile Lys Gly Phe Gln Lys Glu Lys Leu Asn Asp Lys His Ala Asn
195 200 205

His Arg Gln Ser Ser Pro Lys Val Asn Val Leu Ile Ser Glu Glu Ser
210 215 220

Gly Thr Asn Asn Thr Leu Asn His Ser Glu Ile Cys Ala Lys Phe Glu
225 230 235 240

Glu Ser Glu Leu Gly Asp Glu Val Glu Glu Lys Tyr Met Ala Ile Phe
245 250 255

Val Pro Pro Ile Arg Ala Arg Leu Glu Ala Asn Leu Pro Gly Ile Lys
260 265 270

Leu Glu Asp Ile Asp Val Ile Asn Leu Met Asp Ile Cys Pro Phe Glu
275 280 285

Thr Val Ser Leu Thr Ser Asp Gly Ser Lys Leu Ser Pro Phe Cys Asn
290 295 300

Leu Phe Thr Gln Ala Glu Trp Asp Gln Tyr Asp Tyr Leu Gln Ser Leu
305 310 315 320

Ser Lys Tyr Tyr Gly Tyr Gly Ala Gly Asn Pro Leu Gly Pro Thr Gln
325 330 335

Gly Val Gly Phe Val Asn Glu Leu Ile Ala Arg Leu Thr His Ala Pro
340 345 350

Val Val Asp Asn Thr Ser Thr Asn Arg Thr Leu Asp Ala Pro Gly Ala
355 360 365

Ala Thr Phe Pro Leu Asn Tyr Thr Met Tyr Ala Asp Phe Thr His Asp
370 375 380

Asn Gly Met Ile Pro Phe Phe Phe Ala Leu Gly Leu Tyr Asn Gly Thr
385 390 395 400

Ser Pro Leu Ser Leu Thr Lys Ala Gln Ser Thr Asn Glu Thr Asp Gly
405 410 415

Phe Ser Ala Ala Trp Thr Val Pro Phe Gly Ala Arg Ala Tyr Val Glu
420 425 430

Met Met Gln Cys Arg Arg Asp Pro Glu Pro Leu Val Arg Val Leu Val
435 440 445

Asn Asp Arg Val Val Pro Leu His Gly Cys Pro Val Asp Lys Leu Gly
450 455 460

Arg Cys Arg Arg Arg Asp Phe Val Lys Gly Leu Thr Phe Ala Arg Ser
465 470 475 480

Gly Gly Asp Trp Pro Gln Cys Tyr Glu
485

<210> SEQ ID NO 11
<211> LENGTH: 410
<212> TYPE: PRT
<213> ORGANISM: Aspergillus niger

<400> SEQUENCE: 11

-continued

```
Met Gly Val Ser Ala Val Leu Leu Pro Leu Tyr Leu Leu Ala Gly Val
 1               5                  10                  15

Thr Ser Gly Leu Ala Val Pro Ala Ser Arg Asn Gln Ser Thr Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Ala Ile Ser
    50                  55                  60

Pro Asp Val Pro Ala Gly Cys Arg Val Thr Phe Ala Gln Val Leu Ser
65                  70                  75                  80

Arg His Gly Ala Arg Tyr Pro Thr Glu Ser Lys Gly Lys Lys Tyr Ser
                85                  90                  95

Ala Leu Ile Glu Glu Ile Gln Gln Asn Val Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Ile Pro Phe Ile Arg Ser
145                 150                 155                 160

Ser Gly Ser Ser Arg Val Ile Ala Ser Gly Glu Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Ser Phe Asp Thr Ile Ser Thr Ser Thr Val Asp Thr
    210                 215                 220

Lys Leu Ser Pro Phe Cys Asp Leu Phe Thr His Asp Glu Trp Ile His
225                 230                 235                 240

Tyr Asp Tyr Leu Gln Ser Leu Lys Lys Tyr Tyr Gly His Gly Ala Gly
                245                 250                 255

Asn Pro Leu Gly Pro Thr Gln Gly Val Gly Tyr Ala Asn Glu Leu Ile
            260                 265                 270

Ala Arg Leu Thr His Ser Pro Val His Asp Asp Thr Ser Ser Asn His
        275                 280                 285

Thr Leu Asp Ser Asn Pro Ala Thr Phe Pro Leu Asn Ser Thr Leu Tyr
    290                 295                 300

Ala Asp Phe Ser His Asp Asn Gly Ile Ile Ser Ile Leu Phe Ala Leu
305                 310                 315                 320

Gly Leu Tyr Asn Gly Thr Lys Pro Leu Ser Thr Thr Thr Val Glu Asn
                325                 330                 335

Ile Thr Gln Thr Asp Gly Phe Ser Ser Ala Trp Thr Val Pro Phe Ala
            340                 345                 350

Ser Arg Leu Tyr Val Glu Met Met Gln Cys Gln Ala Glu Gln Glu Pro
        355                 360                 365

Leu Val Arg Val Leu Val Asn Asp Arg Val Val Pro Leu His Gly Cys
    370                 375                 380

Pro Ile Asp Ala Leu Gly Arg Cys Thr Arg Asp Ser Phe Val Arg Gly
385                 390                 395                 400

Leu Ser Phe Ala Arg Ser Gly Gly Asp Trp
                405                 410
```

-continued

<210> SEQ ID NO 12
<211> LENGTH: 462
<212> TYPE: PRT
<213> ORGANISM: Aspergillus niger

<400> SEQUENCE: 12

```
Met Gly Val Ser Ala Val Leu Leu Pro Leu Tyr Leu Leu Ser Gly Val
 1               5                  10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Ala Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365

Leu Phe Ala Leu Gly Leu Tyr Asn Gly Thr Lys Pro Leu Ser Thr Thr
    370                 375                 380
```

-continued

Thr Val Glu Asn Ile Thr Gln Thr Asp Gly Phe Ser Ser Ala Trp Thr
385 390 395 400

Val Pro Phe Ala Ser Arg Leu Tyr Val Glu Met Met Gln Cys Gln Ala
405 410 415

Glu Gln Glu Pro Leu Val Arg Val Leu Val Asn Asp Arg Val Val Pro
420 425 430

Leu His Gly Cys Pro Val Asp Ala Leu Gly Arg Cys Thr Arg Asp Ser
435 440 445

Phe Val Arg Gly Leu Ser Phe Ala Arg Ser Gly Gly Asp Trp
450 455 460

<210> SEQ ID NO 13
<211> LENGTH: 455
<212> TYPE: PRT
<213> ORGANISM: Aspergillus niger

<400> SEQUENCE: 13

Met Pro Arg Thr Ser Leu Leu Thr Leu Ala Cys Ala Leu Ala Thr Gly
1 5 10 15

Ala Ser Ala Phe Ser Tyr Gly Ala Ala Ile Pro Gln Ser Thr Gln Glu
20 25 30

Lys Gln Phe Ser Gln Glu Phe Arg Asp Gly Tyr Ser Ile Leu Lys His
35 40 45

Tyr Gly Gly Asn Gly Pro Tyr Ser Glu Arg Val Ser Tyr Gly Ile Ala
50 55 60

Arg Asp Pro Pro Thr Ser Cys Glu Val Asp Gln Val Ile Met Val Lys
65 70 75 80

Arg His Gly Glu Arg Tyr Pro Ser Pro Ser Ala Gly Lys Asp Ile Glu
85 90 95

Glu Ala Leu Ala Lys Val Tyr Ser Ile Asn Thr Thr Glu Tyr Lys Gly
100 105 110

Asp Leu Ala Phe Leu Asn Asp Trp Thr Tyr Tyr Val Pro Asn Glu Cys
115 120 125

Tyr Tyr Asn Ala Glu Thr Thr Ser Gly Pro Tyr Ala Gly Leu Leu Asp
130 135 140

Ala Tyr Asn His Gly Asn Asp Tyr Lys Ala Arg Tyr Gly His Leu Trp
145 150 155 160

Asn Gly Glu Thr Val Val Pro Phe Phe Ser Ser Gly Tyr Gly Arg Val
165 170 175

Ile Glu Thr Ala Arg Lys Phe Gly Glu Gly Phe Phe Gly Tyr Asn Tyr
180 185 190

Ser Thr Asn Ala Ala Leu Asn Ile Ile Ser Glu Ser Glu Val Met Gly
195 200 205

Ala Asp Ser Leu Thr Pro Thr Cys Asp Thr Asp Asn Asp Gln Thr Thr
210 215 220

Cys Asp Asn Leu Thr Tyr Gln Leu Pro Gln Phe Lys Val Ala Ala Ala
225 230 235 240

Arg Leu Asn Ser Gln Asn Pro Gly Met Asn Leu Thr Ala Ser Asp Val
245 250 255

Tyr Asn Leu Met Val Met Ala Ser Phe Glu Leu Asn Ala Arg Pro Phe
260 265 270

Ser Asn Trp Ile Asn Ala Phe Thr Gln Asp Glu Trp Val Ser Phe Gly
275 280 285

Tyr Val Glu Asp Leu Asn Tyr Tyr Tyr Cys Ala Gly Pro Gly Asp Lys

-continued

```
    290                 295                 300

Asn Met Ala Ala Val Gly Ala Val Tyr Ala Asn Ala Ser Leu Thr Leu
305                 310                 315                 320

Leu Asn Gln Gly Pro Lys Glu Ala Gly Ser Leu Phe Phe Asn Phe Ala
                325                 330                 335

His Asp Thr Asn Ile Thr Pro Ile Leu Ala Ala Leu Gly Val Leu Ile
            340                 345                 350

Pro Asn Glu Asp Leu Pro Leu Asp Arg Val Ala Phe Gly Asn Pro Tyr
        355                 360                 365

Ser Ile Gly Asn Ile Val Pro Met Gly Gly His Leu Thr Ile Glu Arg
    370                 375                 380

Leu Ser Cys Gln Ala Thr Ala Leu Ser Asp Glu Gly Thr Tyr Val Arg
385                 390                 395                 400

Leu Val Leu Asn Glu Ala Val Leu Pro Phe Asn Asp Cys Thr Ser Gly
                405                 410                 415

Pro Gly Tyr Ser Cys Pro Leu Ala Asn Tyr Thr Ser Ile Leu Asn Lys
            420                 425                 430

Asn Leu Pro Asp Tyr Thr Thr Thr Cys Asn Val Ser Ala Ser Tyr Pro
        435                 440                 445

Gln Tyr Leu Ser Phe Trp Trp
    450                 455


<210> SEQ ID NO 14
<211> LENGTH: 455
<212> TYPE: PRT
<213> ORGANISM: Aspergillus niger

<400> SEQUENCE: 14

Met Pro Arg Thr Ser Leu Leu Thr Leu Ala Cys Ala Leu Ala Thr Gly
 1               5                  10                  15

Ala Ser Ala Phe Ser Tyr Gly Ala Ala Ile Pro Gln Ser Thr Gln Glu
            20                  25                  30

Lys Gln Phe Ser Gln Glu Phe Arg Asp Gly Tyr Ser Ile Leu Lys His
        35                  40                  45

Tyr Gly Gly Asn Gly Pro Tyr Ser Glu Arg Val Ser Tyr Gly Ile Ala
    50                  55                  60

Arg Asp Pro Pro Thr Gly Cys Glu Val Asp Gln Val Ile Met Val Lys
65                  70                  75                  80

Arg His Gly Glu Arg Tyr Pro Ser Pro Ser Ala Gly Lys Ser Ile Glu
                85                  90                  95

Glu Ala Leu Ala Lys Val Tyr Ser Ile Asn Thr Thr Glu Tyr Lys Gly
            100                 105                 110

Asp Leu Ala Phe Leu Asn Asp Trp Thr Tyr Tyr Val Pro Asn Glu Cys
        115                 120                 125

Tyr Tyr Asn Ala Glu Thr Thr Ser Gly Pro Tyr Ala Gly Leu Leu Asp
    130                 135                 140

Ala Tyr Asn His Gly Asn Asp Tyr Lys Ala Arg Tyr Gly His Leu Trp
145                 150                 155                 160

Asn Gly Glu Thr Val Val Pro Phe Phe Ser Ser Gly Tyr Gly Arg Val
                165                 170                 175

Ile Glu Thr Ala Arg Lys Phe Gly Glu Gly Phe Phe Gly Tyr Asn Tyr
            180                 185                 190

Ser Thr Asn Ala Ala Leu Asn Ile Ile Ser Glu Ser Glu Val Met Gly
        195                 200                 205
```

-continued

```
Ala Asp Ser Leu Thr Pro Thr Cys Asp Thr Asp Asn Asp Gln Thr Thr
    210                 215                 220

Cys Asp Asn Leu Thr Tyr Gln Leu Pro Gln Phe Lys Val Ala Ala Ala
225                 230                 235                 240

Arg Leu Asn Ser Gln Asn Pro Gly Met Asn Leu Thr Ala Ser Asp Val
                245                 250                 255

Tyr Asn Leu Ile Val Met Ala Ser Phe Glu Leu Asn Ala Arg Pro Phe
            260                 265                 270

Ser Asn Trp Ile Asn Ala Phe Thr Gln Asp Glu Trp Val Ser Phe Gly
        275                 280                 285

Tyr Val Glu Asp Leu Asn Tyr Tyr Tyr Cys Ala Gly Pro Gly Asp Lys
    290                 295                 300

Asn Met Ala Ala Val Gly Ala Val Tyr Ala Asn Ala Ser Leu Thr Leu
305                 310                 315                 320

Leu Asn Gln Gly Pro Lys Glu Ala Gly Pro Leu Phe Phe Asn Phe Ala
                325                 330                 335

His Asp Thr Asn Ile Thr Pro Ile Leu Ala Ala Leu Gly Val Leu Ile
            340                 345                 350

Pro Asn Glu Asp Leu Pro Leu Asp Arg Val Ala Phe Gly Asn Pro Tyr
        355                 360                 365

Ser Ile Gly Asn Ile Val Pro Met Gly Gly His Leu Thr Ile Glu Arg
    370                 375                 380

Leu Ser Cys Gln Ala Thr Ala Leu Ser Asp Lys Gly Thr Tyr Val Arg
385                 390                 395                 400

Leu Val Leu Asn Glu Ala Val Leu Pro Phe Asn Asp Cys Thr Ser Gly
                405                 410                 415

Pro Gly Tyr Ser Cys Pro Leu Ala Asn Tyr Thr Ser Ile Leu Asn Lys
            420                 425                 430

Asn Leu Pro Asp Tyr Thr Thr Thr Cys Asn Val Ser Ala Ser Tyr Pro
        435                 440                 445

Gln Tyr Leu Ser Phe Trp Trp
    450                 455
```

<210> SEQ ID NO 15
<211> LENGTH: 355
<212> TYPE: PRT
<213> ORGANISM: Penicillium hordei

<400> SEQUENCE: 15

```
Phe Ile Arg Ser Tyr Asn Tyr Thr Met Gly Gly Asp Asp Leu Val Pro
 1               5                  10                  15

Phe Gly Val Asn Gln Met Val Ser Ser Gly Thr Lys Phe Tyr Gln Arg
            20                  25                  30

Tyr Ala Ala Leu Ala Lys Lys Ala Val Pro Phe Ile Arg Ile Ser Asp
        35                  40                  45

Ser Glu Arg Val Val Ala Ser Gly Val Asn Phe Ile Lys Gly Phe Gln
    50                  55                  60

Lys Glu Lys Leu Asn Asp Lys His Ala Asn His Arg Gln Ser Ser Pro
65                  70                  75                  80

Lys Val Asn Val Leu Ile Ser Glu Glu Ser Gly Thr Asn Asn Thr Leu
                85                  90                  95

Asn His Ser Glu Ile Cys Ala Lys Phe Glu Glu Ser Glu Leu Gly Asp
            100                 105                 110

Glu Val Glu Glu Lys Tyr Met Ala Ile Phe Val Pro Pro Ile Arg Ala
        115                 120                 125
```

-continued

```
Arg Leu Glu Ala Asn Leu Pro Gly Ile Lys Leu Glu Asp Ile Asp Val
    130                 135                 140

Ile Asn Leu Met Asp Ile Cys Pro Phe Glu Thr Val Ser Leu Thr Ser
145                 150                 155                 160

Asp Gly Ser Lys Leu Ser Pro Phe Cys Asn Leu Phe Thr Gln Ala Glu
                165                 170                 175

Trp Asp Gln Tyr Asp Tyr Leu Gln Ser Leu Ser Lys Tyr Tyr Gly Tyr
            180                 185                 190

Gly Ala Gly Asn Pro Leu Gly Pro Thr Gln Gly Val Gly Phe Val Asn
        195                 200                 205

Glu Leu Ile Ala Arg Leu Thr His Ala Pro Val Val Asp Asn Thr Ser
    210                 215                 220

Thr Asn Arg Thr Leu Asp Ala Pro Gly Ala Ala Thr Phe Pro Leu Asn
225                 230                 235                 240

Tyr Thr Met Tyr Ala Asp Phe Thr His Asp Asn Gly Met Ile Pro Phe
                245                 250                 255

Phe Phe Ala Leu Gly Leu Tyr Asn Gly Thr Ser Pro Leu Ser Leu Thr
            260                 265                 270

Lys Ala Gln Ser Thr Asn Glu Thr Asp Gly Phe Ser Ala Ala Trp Thr
        275                 280                 285

Val Pro Phe Gly Ala Arg Ala Tyr Val Glu Met Met Gln Cys Arg Arg
    290                 295                 300

Asp Pro Glu Pro Leu Val Arg Val Leu Val Asn Asp Arg Val Val Pro
305                 310                 315                 320

Leu His Gly Cys Pro Val Asp Lys Leu Gly Arg Cys Arg Arg Arg Asp
                325                 330                 335

Phe Val Lys Gly Leu Thr Phe Ala Arg Ser Gly Gly Asp Trp Pro Gln
            340                 345                 350

Cys Tyr Glu
        355


<210> SEQ ID NO 16
<211> LENGTH: 212
<212> TYPE: PRT
<213> ORGANISM: Penicillium hordei

<400> SEQUENCE: 16

Arg His Gly Ala Arg Tyr Pro Ser Ala Lys Lys Ser Lys Ala Tyr Ala
 1               5                  10                  15

Ala Leu Val Lys Ser Ile Gln Ala Asn Ala Thr Ser Tyr Lys Gly Asn
            20                  25                  30

Thr Glu Phe Ile Arg Ser Tyr Asn Tyr Thr Met Gly Gly Asp Asp Leu
        35                  40                  45

Val Pro Phe Gly Val Asn Gln Met Val Ser Ser Gly Thr Lys Phe Tyr
    50                  55                  60

Gln Arg Tyr Ala Ala Leu Ala Lys Lys Ala Val Pro Phe Ile Arg Ile
65                  70                  75                  80

Ser Asp Ser Glu Arg Val Val Ala Ser Gly Val Asn Phe Ile Lys Gly
                85                  90                  95

Phe Gln Lys Glu Lys Leu Asn Asp Lys His Ala Asn His Arg Gln Ser
            100                 105                 110

Ser Pro Lys Val Asn Val Leu Ile Ser Glu Glu Ser Gly Thr Asn Asn
        115                 120                 125

Thr Leu Asn His Ser Glu Ile Cys Ala Lys Phe Glu Glu Ser Glu Leu
```

-continued

```
    130                 135                 140

Gly Asp Glu Val Glu Glu Lys Tyr Met Ala Ile Phe Val Pro Pro Ile
145                 150                 155                 160

Arg Ala Arg Leu Glu Ala Asn Leu Pro Gly Ile Lys Leu Glu Asp Ile
                165                 170                 175

Asp Val Ile Asn Leu Met Asp Ile Cys Pro Phe Glu Thr Val Ser Leu
            180                 185                 190

Thr Ser Asp Gly Ser Lys Leu Ser Pro Phe Cys Asn Leu Phe Thr His
        195                 200                 205

Asp Glu Trp Val
    210


<210> SEQ ID NO 17
<211> LENGTH: 4898
<212> TYPE: DNA
<213> ORGANISM: Penicillium hordei
<220> FEATURE:
<221> NAME/KEY: misc_feature
<222> LOCATION: (1)...(4898)
<223> OTHER INFORMATION: n = A,T,C or G

<400> SEQUENCE: 17

gaattcatcc gctcatacaa ctacaccatg ggcggtgatg atttggtacc ctttggagtg     60

aaccagatgg tgagctcggg aaccaagttc taccagcgct atgcggcgtt agctaaaaag    120

gccgtgcctt tcattcgcat atctgactcg gagcgggttg tggcttcagg agtgaacttc    180

atcaagggct ttcagaagga aaagttgaat gacaagcatg ccaatcaccg tcaatcaagc    240

cctaaggtca atgtcctcat ctcggaagag tctggcacca acaacactct gaaccacagt    300

gagatctgtg ccaagttcga agaaagtgaa ctaggcgacg aggtcgaaga aaaatacatg    360

gcaatctttg tgccgcccat ccgagcccgt cttgaggcta acctccctgg catcaaactt    420

gaagacatcg atgtgatcaa tctgatggat atttgcccct tcgagacagt gtccctgact    480

agcgatggat ccaagctatc tccattctgc aacctcttca cccaggccga atgggaccaa    540

tacgactacc tccagtcact gagcaagtac tacggttatg gcgcaggcaa cccgctcggc    600

ccaacccagg gtgtcggttt cgtgaacgaa ctcattgccc gtctcactca cgccccagtg    660

gtcgacaaca caagcacaaa ccgtacactc gatgccccgg gcgctgcgac attccccctc    720

aactacacca tgtacgcaga cttcacgcac gacaatggaa tgattccgtt cttctttgct    780

ttgggactgt acaacggcac ttctccactc tccctcacca aggcccagtc aactaacgaa    840

acggacggat tttcagccgc ctggacggtg cctttcggtg ctcgtgctta tgtcgagatg    900

atgcaatgtc gccgcgaccc ggagccgctc gtgcgagtcc tcgttaacga ccgtgttgtt    960

ccgctgcatg gttgccccgt cgataagctt ggccgttgtc gccgtcgcga tttcgtcaag   1020

ggactcactt ttgcgcgctc tggcggtgat tggccccagt gctatgaata ggagattttg   1080

aaaataattg gtgcagggtt ggtcctcttc caacgtactt ttgtctagcg ataccccaaa   1140

gattgcatcc ttacatacat atccttcttt cttttggcca atattaatgc actacacgtt   1200

attacgaaat ctgcttgaaa acaatataat tgcatccaaa tatataatca aaaggctcta   1260

acacatgcaa gtcatcaaaa aggtaatcca aacagccccc aactccaaac aaagaaaagt   1320

ccaaataata atcagcacgt tttaggcatc tctctacctc tctcactttt acatactcca   1380

atgtggctga ccattccttt tcacttgatg cggggcagaa ataacccacg cctcccaaag   1440

aggcatttgc tcatgcaaga catgtacacc atcatccccc aagtcctcac tagacaaagc   1500
```

-continued

```
acgcagtttt tcaagcgaag tccgcctcaa cggcaatcgc cttcccccta ataaagcagg   1560
gagtccatca gatgcgagcg gggcagcagt cggcgactga acagccgagg acgtaccagt   1620
cgcaacagta aaagaagatg gcacagggcc agtagggtaa ttatcgaaca cctcaacacc   1680
gtttgagaca gcaaccgaat caaagtgtgc agcgtaacca atatccttca gaaccaaccg   1740
ctccagctgc tccatttcct cgcgcaggac aaccaacaca tcgcgccact gcccgccagg   1800
tcggaggtag atgccgagta agcggaaatc acgcaattga ggactgtgac gacgtgcgag   1860
tgcgatgatc tcgtctgcgc tcagacgcca gccttggatg ctgagtttgc ggagggtttt   1920
ccagcggatg tggtggaaga gtagctcgag gtcaaggtct aagggtgttt tgctgaggaa   1980
gccgatgtgg atggcgatga ggttcttggc tgcgacgaag aaccggtgga agacttctga   2040
gagatcggcc attgttgcgg tgatgtcggt tgttgagtgg aagtttatgt cgaggcttgt   2100
gaggcgtccg cccatggcgg cgagagttgt tgatggagcg cggaggagct ggagggttgc   2160
ttcggggctg atttggggcc ctgtgaaacg gatggagctg cattttgagt cgaggagggc   2220
gatgctgagg cttgttacgg cgcgcgaaca ggcggtttcc cagtcgaagc ggacgcttgt   2280
tgcggtcctg ccggttccta gtgagcggtc gcgtataaag tcgatgaggt gctcgtctgc   2340
ttcgtcttgc agtcttagga gttttatttc ctgtagagcc gagaacgatg agattgcacg   2400
gcggaggcgg gtttggtcgt tgttggtttc agttagattg gtttgttcac gtagtcggcg   2460
actgtgtagt tgggatattt cgggattttc tgaccccaaa gttcgtagtg tccgggccca   2520
tcctgtattt tgctattagt ttaatttgct cggttgtgca tgagagattg aagagctggt   2580
accgcttcct tgataaaagg gtcgcaccat gtatgtgatg gttttcacat aataggccaa   2640
ctgcatgtct accagctcat ctaatcgccg gaagccatga tcagaaaagc gtagagtgaa   2700
tcgactgaac ttgtaagggg tgccgattcg catgaagcgc ttgcagacga gccgaaagtg   2760
atcaagatcg gacacttcat gttcgtggtt gctaggcctg gaagtatgtc catttccatt   2820
gaatctgcca tttagggctc gaggtgcggg ttcgagaaga aatgacaaga tctcgctcag   2880
tagctcgtca gcaagatcat aaatgtgacg tggctgggcc atgatcggcg cgcgcagccg   2940
aagcatcggc tgcttgttga agtagcagca acatggaaat atggaggaat tgagggaaaa   3000
tcgatgttct taacctgtcc ccaagaccgg agagacaaat cacggaggga attggggaaa   3060
gggggagaga ataagaaata aaaataaaat aaaacaaaaa aaccatgtcg aatactcgac   3120
tcgtcgttct cctgcagaca ctagtaggac agttgacttg tctcacyatg cataacgaga   3180
gctctcgccc taacgattga tttcgcgacc ggggatgatc gtcaagtgcc tgatttagcg   3240
ccctctgcac tgacaagccg ggctctctga cacgatccgc ttaatttcat tggtgacgct   3300
gccacaccag aatcacatga ttgattgact ctgcggccag ccagcgcgcg aacctgcagg   3360
aaaggccatt gaatgagagc gagtagtgtt ggaggggcca atgtcgaccc cgccgggaag   3420
tcgtcacatc atgcagagtg atggaccatg cgtgtggatt atgtgtctgc ccaagaggta   3480
ggcaactatt gattgggggt taatggccga aaccaagatg aactaatgta tgtacaagtg   3540
tttgagagat tatctactag ctgttggatc ttccatatca ttacgtgccg tgtgtaccta   3600
tcagaccttc gcgagangga ctcggcgccg tctgatatct gtgctgctga tcttggactc   3660
gaagccttca agatcagtgg ccgtggctgc ttctccagat tggagtacat ccacctcgaa   3720
tacagcaagg ccgttccatc ccttcttcaa ccgctcttcg ttgacggccg cccctccgga   3780
gtgtgtctcc tttgaaacaa caattgctcc aaggttctcc tcggtaatcg taggcccaaa   3840
aggatcggag atctccacaa attcaaaagc caagttgggt tggatcctta caaggacagt   3900
```

-continued

```
cttcccattg ggtcctggcg caaaaacacg ctcgatctgc ggtgatttct tttcaggaga   3960
gaaatccata atggccgtca gaaaatctgc agtactctgc caacgttcct cccaactctc   4020
aagaaattcg gcatattttt tattgaccaa cagcgcatcc ccggtcactc cgatggtcag   4080
gcggccctcc tgctcccggt ccagcggttc caggaccaat gcaactgccg tgagcaagag   4140
cttgtgacca acatgaaggt gatcaaatgt gccaccaacg accacggaat agtatggagt   4200
ggatggatgt tggtcgtcag gaattaacag gcggtcagag atctcccagt caggctggct   4260
ggtaatggct tgcatgcttg ccgccgtgcc gtcccgagtc tgactgctaa cactgttggt   4320
gaaggaatta gccaaatttt ggccatttgt gttggacata tagaaaacat gatcccaacg   4380
gcgccttgaa tttgctagtg attggatgtc cagaatgggc ccaaagcgag gactatcaga   4440
agcctggatg gtcgaggtgc tctcacttgc attgataaat accacccggg tatcaatgcc   4500
acccggagaa tccaattcaa tgttctgtgt tgcacagaca acaccaacca gggtgtagac   4560
gctgctcaga taatgttgga gttgtgcaaa cactctggcc cgaggttggc aggctgggga   4620
aagaagatct ggaatggcca aagcaatatc cagcatagcc gtacggttgg atccaatcaa   4680
ggcatttgag agcttagtgt agacatccac caaggatggc tggaaggcat ctttgacttg   4740
gacaaaagaa aaggctggag gcgggggaag tagtagtaaa gccgtgggtg aattggtatg   4800
atcggaagcc atggtgttaa gaatatataa ctacagtaac aatcactggg gttcacggat   4860
atcaagccaa caaagaattc ctgcagcccg ggggatcc                           4898
```

<210> SEQ ID NO 18
<211> LENGTH: 860
<212> TYPE: DNA
<213> ORGANISM: Artificial Sequence
<220> FEATURE:
<223> OTHER INFORMATION: clone CS158
<221> NAME/KEY: misc_feature
<222> LOCATION: (1)...(860)
<223> OTHER INFORMATION: 3' to 5'

<400> SEQUENCE: 18

```
tagggcgagt tggagctcca ccgcggtggc ggccgctcta gaactagtgg atcccccggg     60
ctgcaggaat tcgattcggc accggtggaa gaggaccaac cctgcaccaa ttattttcaa    120
aatctcctat tcatagcact ggggccaatc accgccagag cgcgcaaaag tgagtcccta    180
gacgaaatcg cgacggcgac aacggccaag cttatcgacg gggcaaccat gcagcggaac    240
aacacggtcg ttaacgagga ctcgcacgag cggctccggg tcgcggcgac attgcatcat    300
cttgacataa gcacgagcac cgaaaggcac cgtccaggcg gctgaaaatc cgtccgtttc    360
gttagttgac tgggccttgg tgagggagag tggagaagtg ccgttgtaca gtcccaaagc    420
aaagaagaac ggaatcattc cattgtcgtg cgtgaagtct gcgtacatgg tgtagttgag    480
ggggaatgtc gcagcgccgg gggcatcgag tgtacggttt gtgcttgtgt tgtcgaccac    540
tggggcgtga gtgagacggg caatgagttc gttcacgaaa ccgacaccct gggttgggcc    600
gagcgggttg cctgcgccat aaccgtagta cttgctcagt gactggaggt agtcgtattg    660
gtcccattcg gcctgggtga agaggttgca gaatggagat agcttggatc catcgctagt    720
cagggacact gtctcgaagg ggcaaatatc catcagattg atcacatcga tgtcttcaag    780
tttgatgcca gggaggttag cctcaagacg ggactcggat gggcggcaca aagattgcca    840
tgtatttttt cttcgacctc                                                860
```

-continued

```
<210> SEQ ID NO 19
<211> LENGTH: 284
<212> TYPE: PRT
<213> ORGANISM: Artificial Sequence
<220> FEATURE:
<223> OTHER INFORMATION: clone CS158

<400> SEQUENCE: 19

Gly Arg Arg Lys Asn Thr Trp Gln Ser Leu Cys Arg Pro Ser Glu Ser
 1               5                  10                  15

Arg Leu Glu Ala Asn Leu Pro Gly Ile Lys Leu Glu Asp Ile Asp Val
            20                  25                  30

Ile Asn Leu Met Asp Ile Cys Pro Phe Glu Thr Val Ser Leu Thr Ser
        35                  40                  45

Asp Gly Ser Lys Leu Ser Pro Phe Cys Asn Leu Phe Thr Gln Ala Glu
    50                  55                  60

Trp Asp Gln Tyr Asp Tyr Leu Gln Ser Leu Ser Lys Tyr Tyr Gly Tyr
65                  70                  75                  80

Gly Ala Gly Asn Pro Leu Gly Pro Thr Gln Gly Val Gly Phe Val Asn
                85                  90                  95

Glu Leu Ile Ala Arg Leu Thr His Ala Pro Val Val Asp Asn Thr Ser
            100                 105                 110

Thr Asn Arg Thr Leu Asp Ala Pro Gly Ala Ala Thr Phe Pro Leu Asn
        115                 120                 125

Tyr Thr Met Tyr Ala Asp Phe Thr His Asp Asn Gly Met Ile Pro Phe
    130                 135                 140

Phe Phe Ala Leu Gly Leu Tyr Asn Gly Thr Ser Pro Leu Ser Leu Thr
145                 150                 155                 160

Lys Ala Gln Ser Thr Asn Glu Thr Asp Gly Phe Ser Ala Ala Trp Thr
                165                 170                 175

Val Pro Phe Gly Ala Arg Ala Tyr Val Lys Met Met Gln Cys Arg Arg
            180                 185                 190

Asp Pro Glu Pro Leu Val Arg Val Leu Val Asn Asp Arg Val Val Pro
        195                 200                 205

Leu His Gly Cys Pro Val Asp Lys Leu Gly Arg Cys Arg Arg Arg Asp
    210                 215                 220

Phe Val Gly Leu Thr Phe Ala Arg Ser Gly Gly Asp Trp Pro Gln Cys
225                 230                 235                 240

Tyr Glu Glu Ile Leu Lys Ile Ile Gly Ala Gly Leu Val Leu Phe His
                245                 250                 255

Arg Cys Arg Ile Glu Phe Leu Gln Pro Gly Gly Ser Thr Ser Ser Arg
            260                 265                 270

Ala Ala Ala Thr Ala Val Glu Leu Gln Leu Ala Leu
        275                 280


<210> SEQ ID NO 20
<211> LENGTH: 950
<212> TYPE: DNA
<213> ORGANISM: Artificial Sequence
<220> FEATURE:
<223> OTHER INFORMATION: clone CS158
<221> NAME/KEY: misc_feature
<222> LOCATION: (1)...(950)
<223> OTHER INFORMATION: n = A,T,C or G

<400> SEQUENCE: 20

cccatcacts aagggaaaaa aagctgggta ccgggccccc cctcgaggtc gacggtatcg     60
```

-continued

```
ataagcttga ttcggcaccg gtggaagagg accaaccagc gggatcaaaa cactcacgag    120

cacaacctcc gcaaggggtt aacccaaatg ctttagagcc aggtcgaaat ttaaaaatgn    180

actgatttcc ccctcttcgc attcgatatc cttgcaggtt ccacgtactt gtcgtgatac    240

cctctactca ttcactaggt gcaatggcag cgttctccaa agaaaagcat ggggaggaag    300

agggcctact tggcgagagc caagatcaag gccggaagca gcaacgccag cgatcggccc    360

aaaaatggcg tacaattacc ctagtatccc tgctgggcgc tttcgccctg tttgtgtact    420

tcgcgaaggg gtcccagtgc aaccgccccc cctcgcatgt cacaacccag cccgacctac    480

ctgtggcttt tcccctgaac aagtcgaagc gatcatcgca tcacgaacat gcctgcaata    540

ctgttgatgg cggttatcaa tgcaactcct cgctctcaca caagtggggc caatattcgc    600

cctatttctc tctttctgac gaatcggcca tctcagatga ggtacctcac ggttgtcaga    660

tcacttttgc tcaggtgatc tcccgtcatg gtgctcgatt cccgtcggcg aaaaagagca    720

aggcatatgc cgcgctcgtt aaaagcatcc aagcgaacgc gacttcatac aagggcaaca    780

cggaattcat ccgctcatac aactacacca tgggcggtga tgatttggta cctttggagt    840

gaaccagatg gtgagctcgg gaacaagttc taccagcgct atgcggcgtt asstaaaaag    900

gccgtgcttt cattcgcata tctgactcgg agcgggttgt ggcttcagga               950
```

<210> SEQ ID NO 21
<211> LENGTH: 312
<212> TYPE: PRT
<213> ORGANISM: Artificial Sequence
<220> FEATURE:
<223> OTHER INFORMATION: clone CS158
<221> NAME/KEY: VARIANT
<222> LOCATION: (1)...(312)
<223> OTHER INFORMATION: Xaa = Any Amino Acid

<400> SEQUENCE: 21

```
His His Xaa Arg Glu Lys Lys Leu Gly Thr Gly Pro Pro Leu Glu Val
 1               5                  10                  15

Asp Gly Ile Asp Lys Leu Asp Ser Ala Pro Val Glu Glu Asp Gln Pro
            20                  25                  30

Ala Gly Ser Lys His Ser Arg Ala Gln Pro Pro Gln Gly Val Asn Pro
        35                  40                  45

Asn Ala Leu Glu Pro Gly Arg Asn Leu Lys Met Xaa Phe Pro Pro Leu
    50                  55                  60

Arg Ile Arg Tyr Pro Cys Arg Phe His Val Leu Val Val Ile Pro Ser
65                  70                  75                  80

Thr His Ser Leu Gly Ala Met Ala Ala Phe Ser Lys Glu Lys His Gly
                85                  90                  95

Glu Glu Glu Gly Leu Leu Gly Glu Ser Gln Asp Gln Gly Arg Lys Gln
            100                 105                 110

Gln Arg Gln Arg Ser Ala Gln Lys Trp Arg Thr Ile Thr Leu Val Ser
        115                 120                 125

Leu Leu Gly Ala Phe Ala Leu Phe Val Tyr Phe Ala Lys Gly Ser Gln
    130                 135                 140

Cys Asn Arg Pro Pro Ser His Val Thr Thr Gln Pro Asp Leu Pro Val
145                 150                 155                 160

Ala Phe Pro Leu Asn Lys Ser Lys Arg Ser Ser His His Glu His Ala
                165                 170                 175

Cys Asn Thr Val Asp Gly Gly Tyr Gln Cys Asn Ser Ser Leu Ser His
            180                 185                 190
```

-continued

```
Lys Trp Gly Gln Tyr Ser Pro Tyr Phe Ser Leu Ser Asp Glu Ser Ala
        195                 200                 205

Ile Ser Asp Glu Val Pro His Gly Cys Gln Ile Thr Phe Ala Gln Val
    210                 215                 220

Ile Ser Arg His Gly Ala Arg Phe Pro Ser Ala Lys Lys Ser Lys Ala
225                 230                 235                 240

Tyr Ala Ala Leu Val Lys Ser Ile Gln Ala Asn Ala Thr Ser Tyr Lys
                245                 250                 255

Gly Asn Thr Glu Phe Ile Arg Ser Tyr Asn Tyr Thr Met Gly Gly Asp
            260                 265                 270

Asp Leu Val Pro Leu Glu Thr Arg Trp Ala Arg Glu Gln Val Leu Pro
        275                 280                 285

Ala Leu Cys Gly Val Xaa Lys Gly Arg Ala Phe Ile Arg Ile Ser Asp
    290                 295                 300

Ser Glu Arg Val Val Ala Ser Gly
305                 310


<210> SEQ ID NO 22
<211> LENGTH: 96
<212> TYPE: DNA
<213> ORGANISM: Artificial Sequence
<220> FEATURE:
<223> OTHER INFORMATION: vector

<400> SEQUENCE: 22

agatcttcga atgcatcgcg cgcaccgtac gtctcgagga attcctgcag gatatctgga     60

tccacgaagc ttccctggtg acgtcaccgg ttctag                               96


<210> SEQ ID NO 23
<211> LENGTH: 853
<212> TYPE: DNA
<213> ORGANISM: Penicillium piceum

<400> SEQUENCE: 23

attcggcatg gcgcgcggta tccgacttcg tacaaggatg agaaatatgc agaacttgtt     60

gataacatcc acaagactgc aacagcgtat atgggcgact tttctgtttt gaaggactac    120

aagtaccaac taggagccaa taacctgacg gagctcggcc aacagcagtt aattgtctct    180

ggaatgaggt tctatgagcg atacaggagc cttgctcgcg ataacgtgcc atttgttcgt    240

tccgcgggct ccacccgggt tgttgcgtct ggcgactttt tcaatcaggg atttcaagct    300

gcaaaggatc gtgatccagt atcgaataag actcaacagc caccggttat caacgttatc    360

ataccagagg gtagccagtg gaataatacg ctggacgtca ctacttgtcc gtcttttcaa    420

aatgacacat cggcagacac agcacaagag aagtttctca atgttttcgc tccttcaatc    480

ctccagaaaa tcacggctgg tcttcccggt acacaactga aggttgaaga tgtccctctg    540

atcatggatc tgtgtccatt tgaaaccgtg gcgaatccca ataccagcac ccagttgtct    600

cccctgtgcg acttattcac actgtccgaa tggcaatcgt acgattacta caacactctc    660

gggaaatatt acggacatgg tcagggtaac cctttgggtc cgacacaggg agtcggattt    720

gtgaatgaag tgattgctcg catgacccag tccccagtca aggaccacac cagtgtcaac    780

aacacactcg attccgatgc gacaactttc cctctggggc cagcgctata cgcagatttc    840

ccacatgaca aca                                                       853


<210> SEQ ID NO 24
<211> LENGTH: 283
```

-continued

```
<212> TYPE: PRT
<213> ORGANISM: Penicillium piceum

<400> SEQUENCE: 24

Arg His Gly Ala Arg Tyr Pro Thr Ser Tyr Lys Asp Glu Lys Tyr Ala
 1               5                  10                  15

Glu Leu Val Asp Asn Ile His Lys Thr Ala Thr Ala Tyr Met Gly Asp
            20                  25                  30

Phe Ser Val Leu Lys Asp Tyr Lys Tyr Gln Leu Gly Ala Asn Asn Leu
        35                  40                  45

Thr Glu Leu Gly Gln Gln Gln Leu Ile Val Ser Gly Met Arg Phe Tyr
    50                  55                  60

Glu Arg Tyr Arg Ser Leu Ala Arg Asp Asn Val Pro Phe Val Arg Ser
65                  70                  75                  80

Ala Gly Ser Thr Arg Val Val Ala Ser Gly Asp Phe Phe Asn Gln Gly
                85                  90                  95

Phe Gln Ala Ala Lys Asp Arg Asp Pro Val Ser Asn Lys Thr Gln Gln
            100                 105                 110

Pro Pro Val Ile Asn Val Ile Ile Pro Glu Gly Ser Gln Trp Asn Asn
        115                 120                 125

Thr Leu Asp Val Thr Thr Cys Pro Ser Phe Gln Asn Asp Thr Ser Ala
    130                 135                 140

Asp Thr Ala Gln Glu Lys Phe Leu Asn Val Phe Ala Pro Ser Ile Leu
145                 150                 155                 160

Gln Lys Ile Thr Ala Gly Leu Pro Gly Thr Gln Leu Lys Val Glu Asp
                165                 170                 175

Val Pro Leu Ile Met Asp Leu Cys Pro Phe Glu Thr Val Ala Asn Pro
            180                 185                 190

Asn Thr Ser Thr Gln Leu Ser Pro Leu Cys Asp Leu Phe Thr Leu Ser
        195                 200                 205

Glu Trp Gln Ser Tyr Asp Tyr Tyr Asn Thr Leu Gly Lys Tyr Tyr Gly
    210                 215                 220

His Gly Gln Gly Asn Pro Leu Gly Pro Thr Gln Gly Val Gly Phe Val
225                 230                 235                 240

Asn Glu Val Ile Ala Arg Met Thr Gln Ser Pro Val Lys Asp His Thr
                245                 250                 255

Ser Val Asn Asn Thr Leu Asp Ser Asp Ala Thr Thr Phe Pro Leu Gly
            260                 265                 270

Pro Ala Leu Tyr Ala Asp Phe Pro His Asp Asn
        275                 280


<210> SEQ ID NO 25
<211> LENGTH: 20
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(20)
<223> OTHER INFORMATION: n = A,T,C or G

<400> SEQUENCE: 25

cgncayggng cncgntaycc                                              20


<210> SEQ ID NO 26
<211> LENGTH: 20
<212> TYPE: DNA
<213> ORGANISM: Artificial Sequence
```

-continued

<220> FEATURE:
<223> OTHER INFORMATION: primer
<221> NAME/KEY: misc_feature
<222> LOCATION: (1)...(20)
<223> OTHER INFORMATION: n = A,T,C or G

<400> SEQUENCE: 26
ayccaytcrt cntgngtraa 20

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
cggcgatatc agtatccctg cggtc 25

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
cggcgatatc ccggtgacgt cgggt 25

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
cggcaccggt ggaagaggac caacc 25

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
cggcaccggt gcattaatat tggcc 25

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
gttgatatca cttgtcgtga taccc 25

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32

-continued

```
tctgatatct cgatatcctt gcagg                                25


<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33

cgbcayggvg ckcgstaycc dwc                                  23


<210> SEQ ID NO 34
<211> LENGTH: 24
<212> TYPE: DNA
<213> ORGANISM: Artificial Sequence
<220> FEATURE:
<223> OTHER INFORMATION: primer
<221> NAME/KEY: misc_feature
<222> LOCATION: (1)...(24)
<223> OTHER INFORMATION: n = A,T,C or G

<400> SEQUENCE: 34

rttrtcrtgn srraartcnr crta                                 24
```